US009763980B2

(12) United States Patent
Zon et al.

(10) Patent No.: US 9,763,980 B2
(45) Date of Patent: Sep. 19, 2017

(54) COMBINED CHEMICAL MODIFICATION OF SPHINGOSINE-1-PHOSPHATE (S1P) AND CXCR4 SIGNALLING PATHWAYS FOR HEMATOPOIETIC STEM CELL (HSC) MOBILIZATION AND ENGRAFTMENT

(75) Inventors: Leonard I Zon, Wellesley, MA (US); Owen J. Tamplin, Cambridge, MA (US)

(73) Assignee: Children's Medical Center Corporation, Boston, MA (US)

( * ) Notice: Subject to any disclaimer, the term of this patent is extended or adjusted under 35 U.S.C. 154(b) by 328 days.

(21) Appl. No.: 14/126,768

(22) PCT Filed: Jun. 18, 2012

(86) PCT No.: PCT/US2012/042934
§ 371 (c)(1),
(2), (4) Date: Mar. 12, 2014

(87) PCT Pub. No.: WO2012/174522
PCT Pub. Date: Dec. 20, 2012

(65) Prior Publication Data
US 2014/0193376 A1    Jul. 10, 2014

Related U.S. Application Data

(60) Provisional application No. 61/497,694, filed on Jun. 16, 2011.

(51) Int. Cl.
| A61K 45/00 | (2006.01) |
| A61K 35/26 | (2015.01) |
| A01N 25/00 | (2006.01) |
| A61K 35/14 | (2015.01) |
| A61K 38/04 | (2006.01) |
| A61K 31/137 | (2006.01) |
| A61K 31/381 | (2006.01) |
| A61K 31/395 | (2006.01) |
| A61K 31/4245 | (2006.01) |
| A61K 31/662 | (2006.01) |
| A61K 45/06 | (2006.01) |
| A61K 35/28 | (2015.01) |
| A61K 31/138 | (2006.01) |

(52) U.S. Cl.
CPC ............ *A61K 35/14* (2013.01); *A61K 31/137* (2013.01); *A61K 31/138* (2013.01); *A61K 31/381* (2013.01); *A61K 31/395* (2013.01); *A61K 31/4245* (2013.01); *A61K 31/662* (2013.01); *A61K 35/28* (2013.01); *A61K 38/04* (2013.01); *A61K 45/06* (2013.01)

(58) Field of Classification Search
None
See application file for complete search history.

(56) References Cited

U.S. PATENT DOCUMENTS

2008/0234294 A1    9/2008  Kovarik et al.

2008/0300165 A1    12/2008  Poznansky et al.
2013/0108579 A1*   5/2013   Chen .................... A61K 31/137
                                                        424/85.1
2014/0094444 A1*   4/2014   Botchwey, III ........ A61K 45/06
                                                        514/183

FOREIGN PATENT DOCUMENTS

| JP | 2007267665 | 10/2007 |
| WO | 2005/105146 | 11/2005 |
| WO | 2007/036036 | 4/2007 |

(Continued)

OTHER PUBLICATIONS

Juarez et al. Blood, 119(3):707-716 (2012). "Sphingosine-1 phosphate facilitates trafficking of hematopoietic stem cells and their mobilization by CXCR4 antagonists in mice."
Kimura et al., Blood, 103(12):4478-4486 (2004). "The sphingosine 1-phosphate receptor agonist FTY270 supports CXCR4-dependent migration and bone marrow homing of human CD34+ progenitor cells."
Harun et al.: "S1P1 Agonists for Use as Adjunct Mobilizing Agents", Blood, ASH Annual Meeting Abstracts, 116 (21): Abstract (2010).
Ou et al.: "Role of sphingosine 1-phosphate receptor signaling in hematopoietic stem/progenitor cell transmigration", J. South. Med. Univ., 29(9):1862-1865 (2009).
Marsolais et al.: "Chemical modulators of sphigosine-1-phosphate receptors as barrier-oriented therapeutic molecules", Nature Reviews. 8(4):297-307 (2009).
Extended European Search Report for corresponding EP Application No. 12799926 dated Nov. 28, 2014.

(Continued)

*Primary Examiner* — Michail Belyavskyi
(74) *Attorney, Agent, or Firm* — Nixon Peabody LLP

(57) ABSTRACT

The present embodiments provide for combinations of modulators that increase hematopoietic stem cell engraftment or increase mobilization in vivo. Methods and compositions for modulating the mobilization of stem cells, particularly for promoting or increasing the mobilization of hematopoietic stem cells (HSCs) from the bone marrow to the peripheral blood are disclosed. One aspect of the invention relates to the use of a CXCR4 antagonist that act in concert with specific molar ratios of S1P receptor 1 (S1PR1) modulator agents to promote HSC mobilization. The invention also relates to methods of using these combinations of CXCR4 antagonists and S1PR1 modulator agents for enhancing the mobilization of hematopoietic stem cells when harvesting of the stem cells, for example for the treatment of diseases, disabilities or conditions whereby transplantation of such cells would be beneficial in ameliorating a symptom associated with such diseases, disabilities or conditions. Another aspect of the invention relates to the use of a CXCR4 antagonist that act in concert with different, but specific molar ratios of S1P receptor 1 (S1PR1) modulator agents to promote HSC engraftment and methods for promoting HSC engraftment in a subject in need thereof, e.g., a recipient subject of a bone marrow or HSC transplant. Methods of screening for novel agents and pharmaceutical compositions comprising these agents are also disclosed.

8 Claims, 43 Drawing Sheets

(56) References Cited

FOREIGN PATENT DOCUMENTS

| WO | 2008/017025 | 2/2008 |
| --- | --- | --- |
| WO | 2008/019371 | 2/2008 |
| WO | 2012/129073 | 9/2012 |

OTHER PUBLICATIONS

Bertrand et al., "Hematopoietic stem cells derive directly from aortic endothelium during development", Nature 464 (7285)108-111 (2010).

Boisset et al., "In vivo imaging of haematopoietic cells emerging from the mouse aortic endothelium", Nature 464:116-120 (2010).

Fonseca et al., "Polarization and Migration of Hematopoietic Stem and Progenitor Cells Rely on the RhoA/ROCK I Pathway and an Active Reorganization of the Microtubule Network", The Journal of Biological Chemistry 285 (41):31661-31671 (2010).

Glass et al., "Stromel cell-derived factor-1 and hematopoietic cell homing in an adult zebrafish model of hematopoietic cell transplantation", Blood 118(3):766-774 (2011).

Huang et al., "NXT2 is required for embryonic heart development in zebrafish", BMC Developmental Biology 5(7) (2005).

Iwasaki et al., "Endothelial protein C receptor-expressing hematopoietic stem cells reside in the perisinusoidal niche in fetal liver", Blood 116(4):544-553 (2010).

Jin et al., "Cellular and molecular analyses of vascular tube and lumen formation in zebrafish", Development 132 (23):5199-5209 (2005).

Jo et al., "S1P1-Selective In Vivo-Active Agonists from High-Throughput Screening: Off-the-Shelf Chemical Probes of Receptor Interactions, Signaling, and Fate", Chem Biol. 12:703-715 (2005).

Kai et al., "Sphingosine-1-phosphate receptors regulate individual cell behaviours underlying the directed migration of prechordal plate progenitor cells during zebrafish gastrulation", Development 135:3043-3051 (2008).

Kissa et al., "Blood stem cells emerge from aortic endothelium by a novel type of cell transition", Nature 464 (7285):112-115 (2010).

Kissa et al., "Live imaging of emerging hematopoietic stem cells and early thymus colonization", Blood 111 (3):1147-1156 (2008).

Koh et al., "Sphingosine-1-phosphate initiates rapid refraction of pseudopodia by localized RhoA activation", Cellular Signalling 19:1328-1338 (2007).

Kwan el al., "The Tol2kit: A Multisite Gateway-Based Construction Kit for Tol2 Transposon Transgenesis Constructs", Developmental Dynamics 236:3088-3099 (2007).

Lee et al., "Akt-Mediated Phosphorylation of the G Protein-Coupled Receptor EDG-1 Is Required for Endothelial Cell Chemotaxis", Molecular Cell 8:693-704 (2001).

Lin et al., "Analysis of thrombocyte development in CD41-GFP transgenic zebrafish", Blood 106(12):3803-3810 (2005).

Lo et al., "Cyclical modulation of sphingosine-1- phosphate receptor 1 surface expression during lymphocyte recirculation and relationship to lymphoid organ transit", JEM 201(2):291-301 (2005).

Ma et al., "The identification and characterization of zebrafish hematopoietic stem cells", Blood 118(2):289-297 (2011).

Mandala et al., "Alteration of Lymphocyte Trafficking by Sphingosine-1-Phosphate Receptor Agonists", Science 296:346-349 (2002).

Massberg et al., "Immunosurveillance by Hematopoietic Progenitor Cells Trafficking through Blood, Lymph, and Peripheral Tissues",Cell 131:994-1008 (2007).

Meijering et al., "Methods for Cell and Particle Tracking", Methods in Enzymology 504:183-200 (2012).

Mosimann et al., "Ubiquitous transgene expression and Cre-based recombination driven by the ubiquitin promoter in zebrafish", Development 138:169-177 (2011).

Motta et al., "The Three-Dimensional Microanatomy of the Liver", Arch Histol Jpn 47(1):1-30 (1984).

Murayama et al., "Tracing Hematopoietic Precursor Migration to Successive Hematopoietic Organs during Zebrafish Development", Immunity 25:963-975 (2006).

North et al., "Prostaglandin E2 regulates vertebrate haematopoietic stem cell homeostasis", Nature 447 (7147):1007-1011 (2007).

Nottingham et al., "Runx1-mediated hematopoietic stem-cell emergence is controlled by a Gata/Ets/SCL-regulated enhancer", Blood 110(13):4188-4197 (2007).

Pan et al., "A Monoselective Sphingosine-1-Phosphate Receptor-1 Agonist Prevents Allograft Rejection in a Stringent Rat Heart Transplantation Model", Chemistry & Biology 13:1227-1234 (2006).

Ratajczak et al., "Novel insight into stem cell mobilization-Plasma sphingosine-1-phosphate is a major chemoattractant that directs the egress of hematopoietic stem progenitor cells from the bone marrow and its level in peripheral blood increases during mobilization due to activation of complement cascade/membrane attack complex", Leukemia 24:976-985 (2010).

Rivera et al., "The Alliance of Sphingosine-1-Phosphate And Its Receptors in Immunity", Nat Rev Immunol. 8(10):753-763 (2008).

Ryser et al., "S1P1 overexpression stimulates S1P-dependent chemotaxis of human CD34+ hematopoietic progenitor cells but strongly inhibits SDF-1/CXCR4-dependent migration and in vivo homing", Mol Immunol. 46:166-171 (2008).

Sanchez et al., "Characterization of the First Definitive Hematopoietic Stem Cells in the AGM and Liver of the Mouse Embryo", Immunity 5:513-525 (1996).

Thisse et al., "High-resolution in situ hybridization to whole-mount zebrafish embryos", Nat Protoc 3(1):59-69 (2008).

Traver et al., "Transplantation and in vivo imaging of multilineage engraftment in zebrafish bloodless mutants", Nat Immunol 4(12):1238-1246 (2003).

Wan, "An Interactive Visualization Tool for Multi-channel Confocal Microscopy Data in Neurobiology Research", IEEE Trans Vis Comput Graph 15(6):1489-1496 (2009).

Worthylake et al., "RhoA and ROCK Promote Migration by Limiting Membrane Protrusions", J Biol Chem. 278 (15):13578-13584 (2003).

Worthylake et al., "RhoA is required for monocyte tail retraction during transendothelial migration", J Cell Biol. 154(1):147-160 (2001).

Yanai et al., "Sphingosine-1-phosphate and lysophosphatidic acid trigger invasion of primitive hematopoietic cells into stromal cell layers", Blood 96(1):139-144 (2000).

* cited by examiner

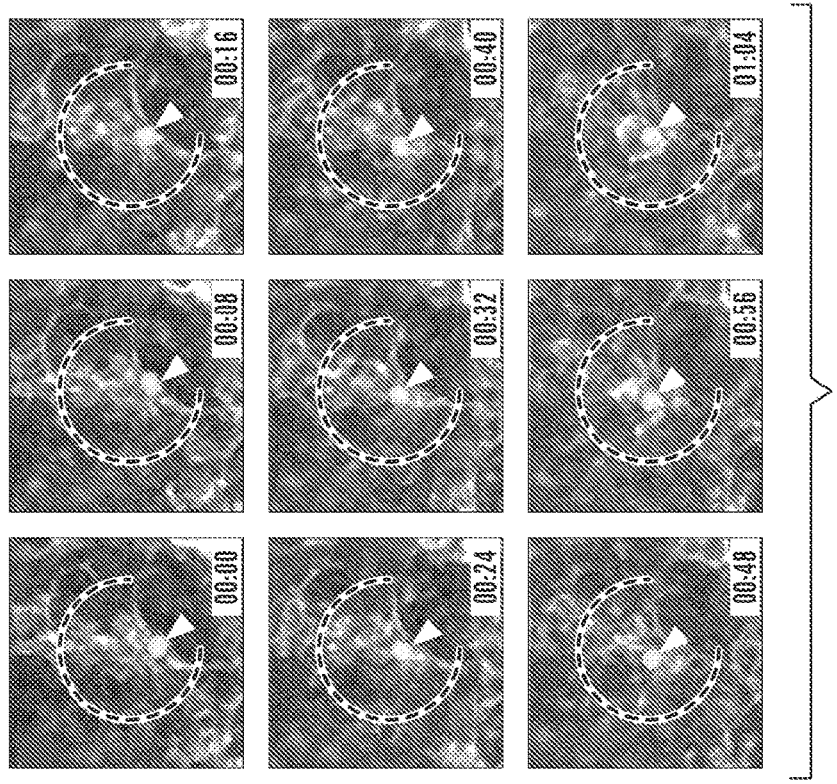
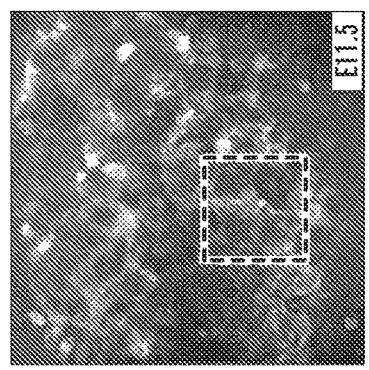
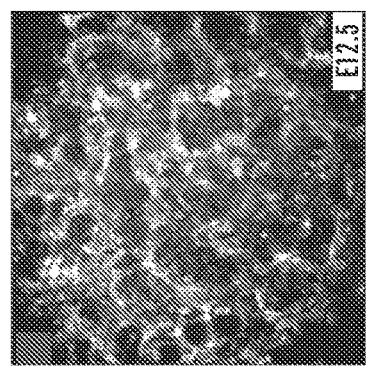

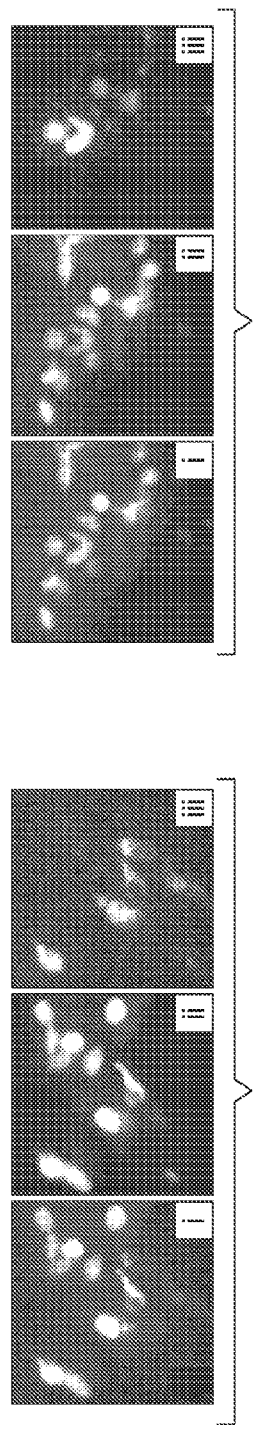
*FIG. 4A*
*FIG. 4B*
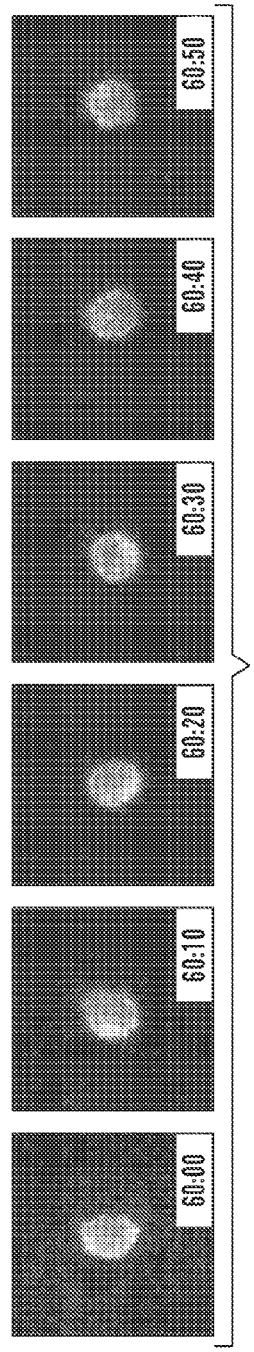
*FIG. 4C*
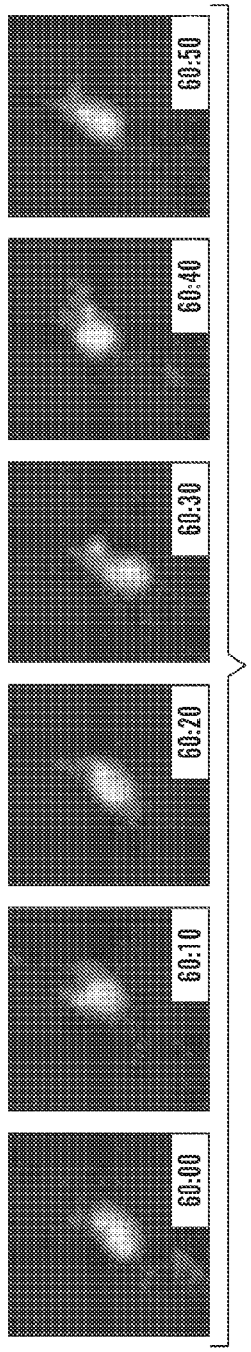
*FIG. 4D*

 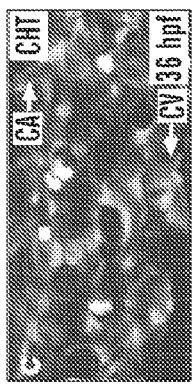 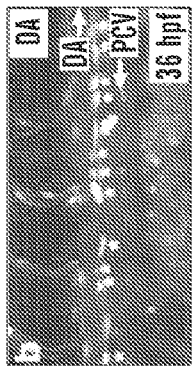 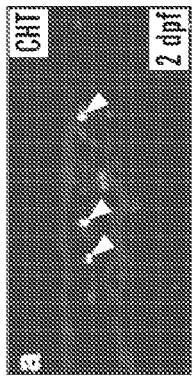 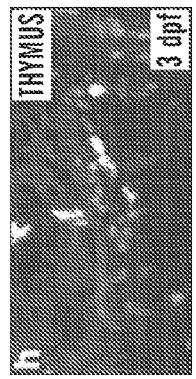 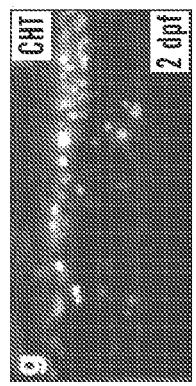 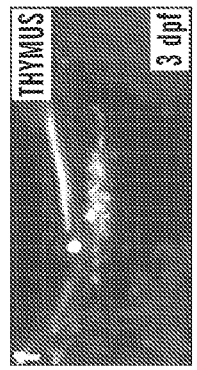 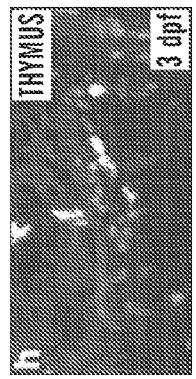
FIG. 5A  FIG. 5B  FIG. 5C  FIG. 5D
FIG. 5E  FIG. 5F  FIG. 5G  FIG. 5H

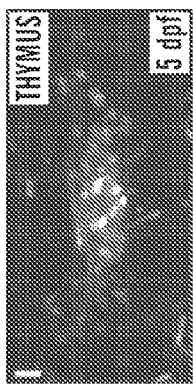
*FIG. 5J*
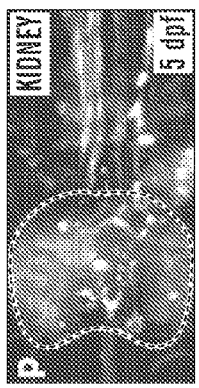
*FIG. 5N*
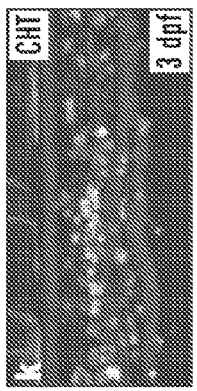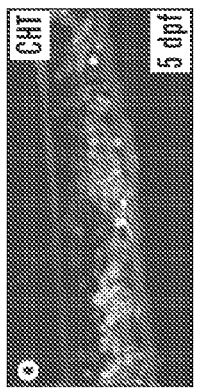
*FIG. 5K* *FIG. 5O*
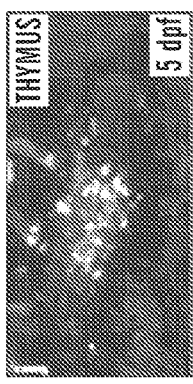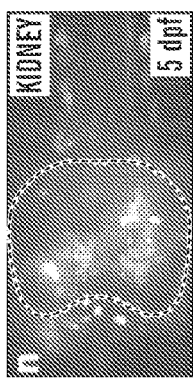
*FIG. 5L* *FIG. 5P*
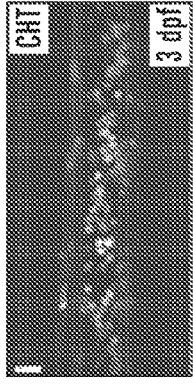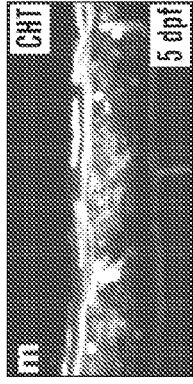
*FIG. 5I* *FIG. 5M*

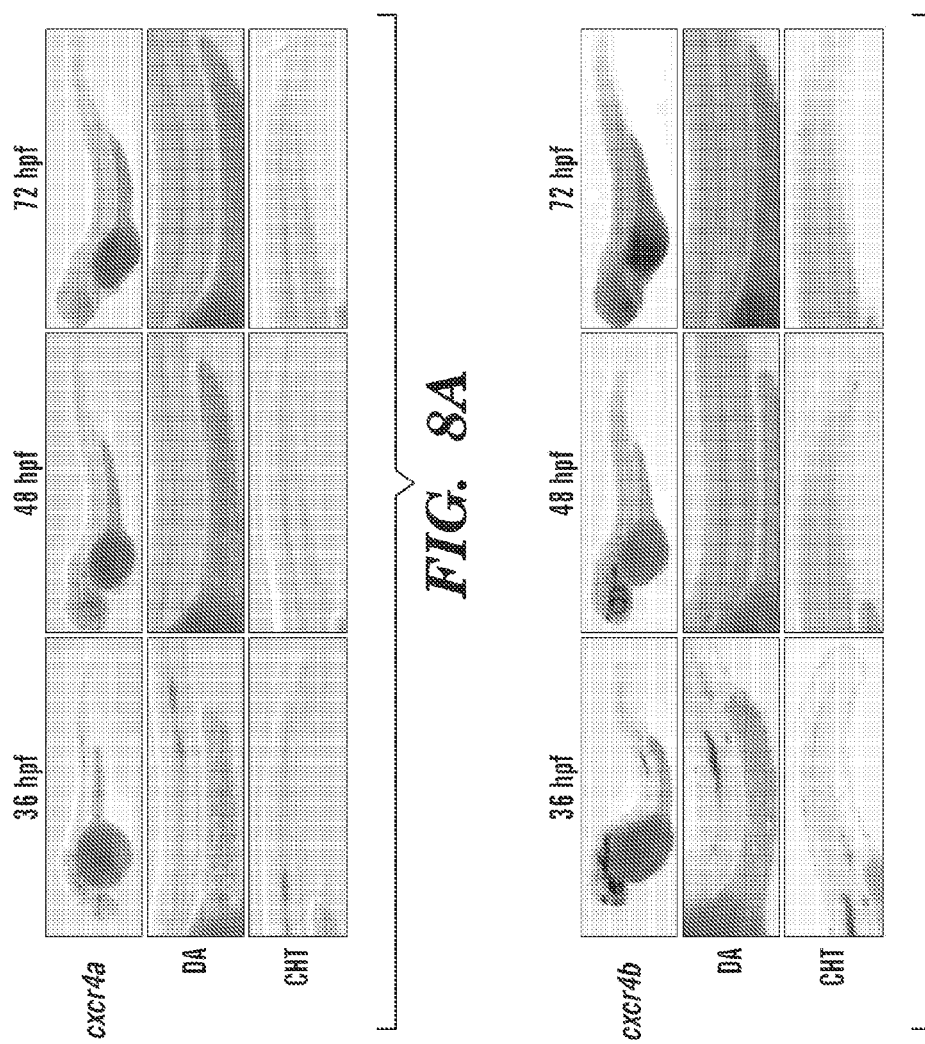

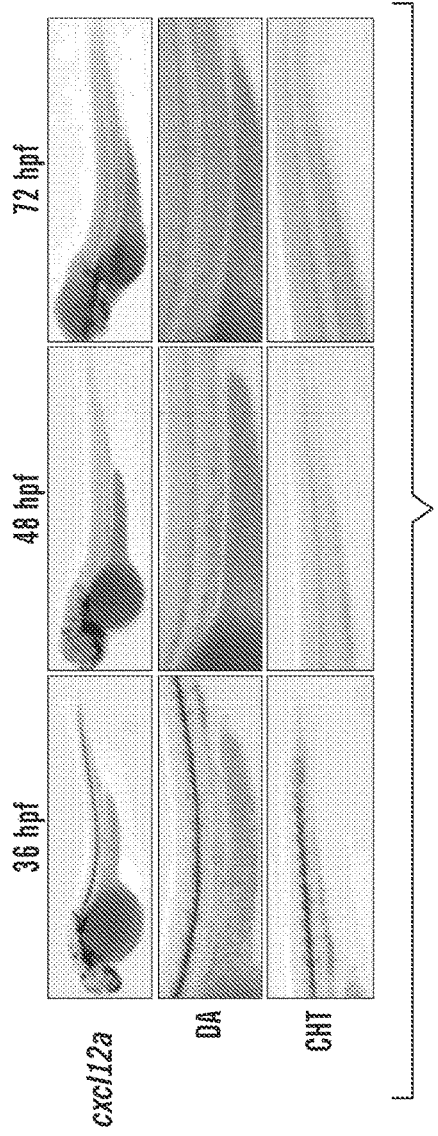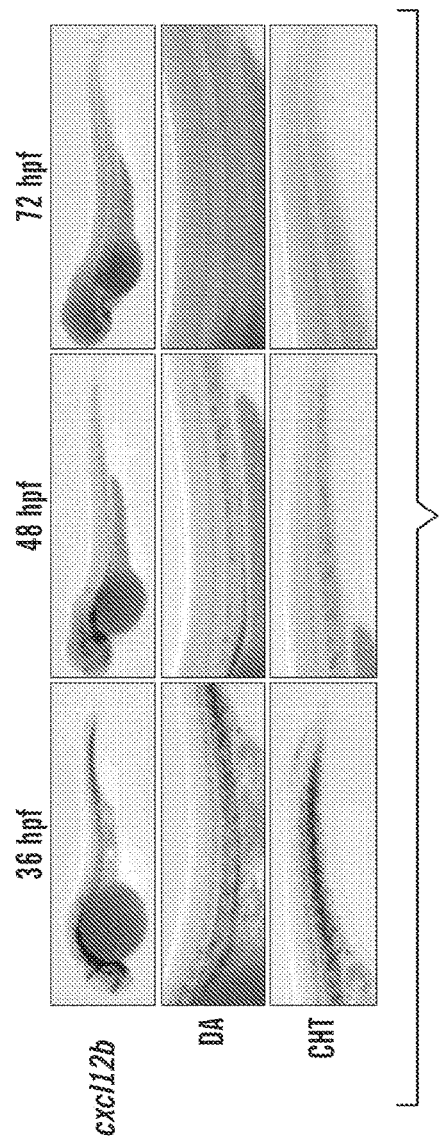
FIG. 8C
FIG. 8D

COMBINED CHEMICAL MODIFICATION OF SPHINGOSINE-1-PHOSPHATE (S1P) AND CXCR4 SIGNALLING PATHWAYS FOR HEMATOPOIETIC STEM CELL (HSC) MOBILIZATION AND ENGRAFTMENT

CROSS REFERENCE TO RELATED APPLICATIONS

This Application is a 35 U.S.C. §371 National Phase Entry Application of International Application No. PCT/US2012/042934 filed Jun. 18, 2012, which designates the U.S., and which claims benefit under 35 U.S.C. §119(e) of U.S. Provisional Application No. 61/497,694, filed Jun. 16, 2011, the contents of each of which are incorporated herein by reference in their entireties.

GOVERNMENT SUPPORT

This invention was supported by the National Institutes of Health—NIH Grant No. NIH R01 HL04880, R01 HL097794-02 and 5R01HL048801-18. The government of the United States has certain rights in this invention.

FIELD OF THE INVENTION

The present embodiments provide for combinations of modulators that increase hematopoietic stem cell engraftment or increase mobilization in vivo. Methods and compositions for modulating the mobilization of stem cells, particularly for promoting or increasing the mobilization of hematopoietic stem cells (HSCs) from the bone marrow to the peripheral blood are disclosed. One aspect of the invention relates to the use of a CXCR4 antagonist that act in concert with specific molar ratios of SIP receptor 1 (S1PR1) modulator agents to promote HSC mobilization. The invention also relates to methods of using these combinations of CXCR4 antagonists and S1PR1 modulator agents for enhancing the mobilization of hematopoietic stem cells when harvesting of the stem cells, for example for the treatment of diseases, disabilities or conditions whereby transplantation of such cells would be beneficial in ameliorating a symptom associated with such diseases, disabilities or conditions. Another aspect of the invention relates to the use of a CXCR4 antagonist that act in concert with different, but specific molar ratios of SIP receptor 1 (S1PR1) modulator agents to promote HSC engraftment and methods for promoting HSC engraftment in a subject in need thereof, e.g., a recipient subject of a bone marrow or HSC transplant. Methods of screening for novel agents and pharmaceutical compositions comprising these agents are also disclosed.

BACKGROUND

Stem cell research holds extraordinary potential for the development of therapies that may change the future for those suffering from diseases such as leukemia, diabetes, and anemia. Much research focuses on the exploration of stem cell biology as a key to treatments for diseases. Through an understanding of the role of stem cells in normal development, researchers seek to capture and direct the innate capabilities of stem cells to treat many conditions. Research is on-going in a number of areas simultaneously: examining the genetic and molecular triggers that drive embryonic stem cells to develop in various tissues; learning how to push those cells to divide and form specialized tissues; culturing embryonic stem cells and developing new lines to work with; searching for ways to eliminate or control Graft Vs. Host Disease by eliminating the need for donors; and generating a line of universally transplantable cells.

Hematopoietic stem cells (HSCs) are derived during embryogenesis in distinct regions where specific inductive events convert mesoderm to blood stem cells and progenitors. There remains a need to elucidate the relationships between particular biomolecules, chemical agents, and other factors in these inductive events. For example, there remains a need to identify which biomolecules or chemical agents show promise in manipulating the HSC population for a desired purpose, such as increasing mobilization of a HSC population for research or therapeutics, or enhancing engraftment after HSC transplantation.

There is accordingly a need for agents and methods that facilitate the mobilization of hematopoietic stem or precursor/progenitor cells to the peripheral blood. Furthermore, the development of such agents may aid in the collection of such hematopoietic stem cells or hematopoietic progenitor cells for use in ex vivo cell cultures, whereby such cells can further be used in engraftment or transplantation procedures. Accordingly, the current invention addresses these needs.

All publications, patent applications, patents and other reference material mentioned are incorporated by reference in their entirety. In addition, the materials, methods and examples are only illustrative and are not intended to be limiting. The citation of references herein shall not be construed as an admission that such is prior art to the present invention

SUMMARY

The compositions and methods of the present embodiments provide for combination of a CXCR4 antagonist with a S1P receptor 1 (S1PR1) modulator agent, where the S1PR1 modulator agent have a bimodal effect in that at some ratios, the combination of CXCR4 antagonist and S1PR1 modulator agent increases HSC mobilization from the bone marrow, and in other ratios, the combination increases HSC engraftment into the bone marrow.

In particular, the inventors have discovered that particular combinations of CXCR4 antagonists with particular combinations of S1P receptor 1 (S1PR1) modulator agents (e.g. agonist and antagonists), either promote migration of HSCs or promote engraftment. Accordingly, the inventors have discovered how to finely tune the relationship between the sphingosine-1-phosphate (S1P) and CXCR4 signaling pathways.

The relationship between the sphingosine-1-phosphate (S1P) and CXCR4 pathways of human CD34+ hematopoietic progenitor cells has been previously described (Ryser et al. Mol Immunol 2008 vol. 46 (1) pp. 166-71). However, Ryster et al., did not demonstrate that S1PR1 modulation could be finely tuned with CXCR4 inhibition to render either mobilization or engraftment of HSCs. Herein the inventors have demonstrated that the combination of CXCR4 antagonists with different ratios of S1PR1 modulator agents (e.g., S1PR1 agonists and antagonists) results in unexpectedly contradicting actions; in one instance CXCR4 antagonists, e.g., AMD3100 in combination with specific molar proportions of S1PR1 modulator agents results in mobilization of the HSCs from the bone marrow, and in another instance, CXCR4 antagonists, e.g., AMD3100 in combination with different molar proportions of S1PR1 modulator agents results in engraftment of the HSCs in the bone marrow and hematopoietic tissues.

In particular, the inventors created a novel zebrafish transgenic line to follow HSCs as they leave the dorsal aorta (DA) where HSCs are first born, to colonize the intermediate caudal hematopoietic tissue (CHT) tissue (e.g., the fish equivalent of the fetal liver (FL)) before colonizing in the bone marrow (BM). Using this transgenic line, the inventors performed a chemical genetic screen to identify the signaling pathways involved in CHT colonization, and demonstrate that S1P is involved in trafficking of HSCs between embryonic sites of hematopoiesis. The inventors also demonstrate that different concentrations of S1PR1 modulators as disclosed herein in combination with CXCR4 antagonists can either promote HSC migration or promote HSC engraftment. Herein the inventors have demonstrate that the combined modulation of S1PR1 and CXCR4 pathways had an unexpected result: positive or negative impact on hematopoietic stem cells (HSCs) using an embryonic zebrafish homing and engraftment assay.

Accordingly, the present invention relates to a unique combination of HSC modulator agents, specifically CXCR4 antagonists with different molar ratios of S1PR1 modulator agents (e.g., S1PR1 agonists and antagonists) which can be administered to a subject for HSC mobilization (e.g., for a bone marrow donor subject) or administered to a subject for HSC engraftment (e.g., for a bone marrow or HSC transplant recipient).

In particular, the inventors discovered that engraftment of HSCs was optimized when different ratios of S1PR1 modulator agents, e.g., a S1PR1 (S1P receptor 1) antagonist (W146) or S1PR1 agonist (FTY720, SEW2871, or AUY954) with a CXCR4 antagonist (e.g., AMD3100) were used. Conversely, the inventors discovered that mobilization of HSCs was enhanced when a different ratio of the same agents; antagonist (W146) or S1PR1 agonist (FTY720 or SEW2871) in combination with a CXCR4 antagonist (e.g., AMD3100) was used.

Accordingly, one aspect of the present invention provides for increasing the mobilization of stem cells, in particular, hematopoietic stem cells, from the bone marrow to the peripheral blood. The invention is further directed to compositions and methods of treating animal subjects, in particular, veterinary and human subjects, with a CXCR4 antagonist in combination with specific ratio of S1PR1 modulator agents to enhance the mobilization of hematopoietic stem cells or progenitor cells from the bone marrow to the peripheral blood. The stem cells or progenitor cells may be harvested by apheresis and used in cell transplantation. The methods and compositions of the invention employ a combination of a CXCR4 antagonist and at least one S1PR1 modulator agent at a specific ratio for mobilization of hematopoietic stem cells or progenitor cells. The CXCR4 antagonist S1PR1 modulator agent at a specific ratio for mobilization of stem cells may also be used as adjunct therapy with chemotherapy or irradiation therapy for treating a cancerous condition.

Without being limited to theory, exemplary CXCR4 antagonists and S1PR1 modulator agent combination concentrations or ratios to increase HSC mobilization are shown in Table 1. In particular, in some embodiments, for mobilization of HSCs, exemplary ratios are as follows: a ratio of AMD3100 to W146 between 1.25-2.0:1, or in some embodiments a ratio of AMD3100:W146 is a 2:1 ratio; a ratio of AMD3100 to FTY720 is 5:1, a ratio of AMD3100 to SEW2871 is between 1.25-5:1, or in some embodiments, a ratio of AMD3100:FTY720 of 5:3. In some embodiments, exemplary concentrations of CXCR4 antagonists and S1PR1 modulator agent useful in methods to increase HSC mobilization in a subject include: 10 µM AMD3100+5 µM W146; 25 µM AMD3100+5 µM FTY720; 25 µM AMD3100+15 µM SEW2871.

Alternatively, another aspect of the present invention provides for increasing the engraftment of stem cells, in particular, hematopoietic stem cells, from the peripheral blood to the bone marrow of a subject, e.g., a subject whom is a recipient of a HSC transplant. The invention is further directed to compositions and methods of treating animal subjects, in particular, veterinary and human subjects, with a CXCR4 antagonist in combination with specific ratio of S1PR1 modulator agents to enhance the engraftment of hematopoietic stem cells or progenitor cells from the peripheral blood to the bone marrow. The stem cells or progenitor cells can be allogenic or autologous. The methods and compositions of the invention employ a combination of a CXCR4 antagonist in combination with specific ratio of S1PR1 modulator agents to enhance the engraftment of hematopoietic stem cells or progenitor cells. The CXCR4 antagonist in combination with at least one S1PR1 modulator agent at a specific ratio for engraftment of stem cells may also be used as adjunct therapy with chemotherapy or irradiation therapy for treating a cancerous condition, e.g., preventing the cancerous cells from leaving the bone marrow, thus preventing or minimizing metastasis. Accordingly, in one embodiment, a CXCR4 antagonist in combination with specific ratio of S1PR1 modulator agents to enhance the engraftment of HSCs can be used for preventing the egress of a cancer stem cell from its niche in a microenvironment thus preventing migration and metastasis to a distant organ or tissue.

Without being limited to theory, exemplary CXCR4 antagonists and S1PR1 modulator agent combination concentrations or ratios to increase HSC engraftment are shown in Table 2. In some embodiments for engraftment of HSCs, exemplary ratios are as follows: a ratio of AMD3100 to W146 of about 0.5-0.6:1, and in some embodiments, a ratio of AMD3100:W146 of 1:2; a ratio of AMD3100 to AUY945 is between 0.4-2.5:1, and in some embodiments, the ratio of AMD3100:AUY945 is 1.1.25, a ratio of AMD3100:FTY720 is between 0.4-3.0:1, in some embodiments, a ratio of AMD3100:FTY720 is 3:1, a ratio of AMD3100 to SEW2871 is between 0.25-1.0:1, and in some embodiments, a ratio of AMD3100:SEW2871 is 1:1. In some embodiments, the following CXCR4 antagonists and S1PR1 modulator agent concentrations are useful in the method as disclosed herein to increase HSC engraftment in a subject: 5 µM AMD3100+10 µM W146; 10 µM AMD3100+12.5 µM AUY954; 15 µM AMD3100+5 µM FTY720; 10 µM AMD3100+10 µM SEW2871.

Accordingly, a first aspect of the invention provides a method for increasing or promoting the mobilization of hematopoietic stem cells or progenitor cells from the bone marrow to the peripheral blood in a mammalian subject, the method comprising administering a CXCR4 antagonist, e.g., AMD3100 in combination with specific ratio of at least one S1PR1 modulator agent to enhance the mobilization of HSCs or progenitor cells.

A second aspect of the invention provides for a method for obtaining a population of hematopoietic stem cells or progenitor cells from a subject, the method comprising the steps of: a) administering a CXCR4 antagonist, e.g., AMD3100 in combination with specific ratio of at least one S1PR1 modulator agent to a subject in an amount sufficient to mobilize the hematopoietic stem cells or progenitor cells from the bone marrow to the peripheral blood of the subject; b) collecting/harvesting the mobilized cells from the peripheral blood by apheresis.

A third aspect of the invention provides for a pharmaceutical composition comprising a CXCR4 antagonist, e.g., AMD3100 in combination with specific ratio of at least one S1PR1 modulator agent to enhance the mobilization of HSCs or progenitor cells, and a pharmaceutically acceptable carrier.

A fourth aspect of the invention provides a method of treating a subject in need of therapy with a CXCR4 antagonist, e.g., AMD3100 in combination with specific ratio of at least one S1PR1 modulator agent to enhance the mobilization of bone marrow cells from the bone marrow to the peripheral blood, comprising administering a CXCR4 antagonist, e.g., AMD3100 in combination with specific ratio of at least one S1PR1 modulator agent to enhance the mobilization of HSCs or progenitor cells as described above. In some embodiments, a CXCR4 antagonist is administered in a pharmaceutical composition also comprising at least one S1PR1 modulator agent in a specific ratio to enhance the mobilization, and in an alternative embodiment, a CXCR4 antagonist can be administered prior to, or substantially at the same time, or after the administration of at least one S1PR1 modulator agent at a specific ration to enhance the mobilization.

A fifth aspect of the invention provides a method for increasing or promoting the engraftment of hematopoietic stem cells or progenitor cells from the peripheral blood to the bone marrow in a mammalian subject, the method comprising administering a CXCR4 antagonist, e.g., AMD3100 in combination with at least one S1PR1 modulator agent at a specific ratio effective to enhance the engraftment of HSCs or progenitor cells.

Accordingly, a sixth aspect of the invention provides for a method for treating a subject in need of a HSC transplant, the method comprising the steps of: a) administering to the subject HSCs, and (b) administering to the subject a CXCR4 antagonist, e.g., AMD3100 in combination with at least one S1PR1 modulator agent at a specific ratio effective to enhance the engraftment of the transplanted hematopoietic stem cells or progenitor cells.

A seventh aspect of the invention provides for a pharmaceutical composition comprising a CXCR4 antagonist, e.g., AMD3100 in combination with at least one S1PR1 modulator agent at a specific ratio effective to enhance the engraftment of HSCs or progenitor cells, and a pharmaceutically acceptable carrier.

A fourth aspect of the invention provides a method of treating a subject in need of therapy with a CXCR4 antagonist, e.g., AMD3100 in combination with at least one S1PR1 modulator agent at a specific ratio effective to enhance the engraftment of HSCs from the peripheral blood to the bone marrow, comprising administering a CXCR4 antagonist, e.g., AMD3100 in combination with at least one S1PR1 modulator agent at a specific ration effective to enhance the engraftment of HSCs or progenitor cells as described above. In some embodiments, a CXCR4 antagonist is administered in a pharmaceutical composition also comprising at least one S1PR1 modulator agent in a specific ratio effective to enhance the engraftment, and in an alternative embodiment, a CXCR4 antagonist can be administered prior to, or substantially at the same time, or after the administration of at least one S1PR1 modulator agent at a specific ratio to enhance the engraftment.

Accordingly, a pharmaceutical composition comprising a S1PR1 modulator agent, either an agonist or antagonist, and a CXCR4 antagonist is envisioned for use in the methods of the invention. In some embodiments, a pharmaceutical composition comprises a CXCR4 antagonist, e.g., AMD3100 in combination with specific ratio of at least one S1PR1 modulator agent to enhance the mobilization of HSCs, and in an alternative embodiment, a pharmaceutical composition comprises a CXCR4 antagonist, e.g., AMD3100 in combination with specific ratio of at least one S1PR1 modulator agent to enhance engraftment HSCs.

The composition may comprise a combination of the S1PR1 modulator agent and the CXCR4 antagonist alone or in further combination with an additional agent, e.g., an anti-cancer drug. In some embodiments, an additional agent is a HSC mobilizer, for example, selected from any one or a combination mobilizer agents from the group consisting of: cytokines selected from the group consisting of interleukin-1 (IL-1), interleukin-3 (IL-3), interleukin-6 (IL-6), interleukin-11 (IL-11), interleukin-7 (IL-7), and interleukin-12 (IL12), IL-8, Mip-1α, Groβ, proteases selected from the group consisting of a metalloproteinase (like MMP2 or MMP9) a serine protease, (like cathepsin G, or elastase) a cysteine protease (like cathepsin K) and a dipeptidyl peptidase-1 (DDP-1 OR CD26), colony stimulating factors selected from the group consisting of granulocyte colony stimulating factor (G-CSF), granulocyte-macrophage colony stimulating factor (GM-CSF), macrophage colony stimulating factor (M-CSF), stem cell factor, FLT-3 ligand or a combination thereof.

In some embodiments, the CXCR4 antagonist AMD-3100 or its analogs, derivatives or combinations thereof. The structure of AMD-3100 and its derivatives and analogs thereof may be found in U.S. Pat. No. 6,987,102, which is incorporated by reference in its entirety.

Another aspect of the invention provides methods of treating of cell populations ex vivo with the CXCR4 antagonist, e.g., AMD3100 in combination with at least one S1PR1 modulator agent in a specific ratio effective to enhance the mobilization of HSCs or progenitor cells and introducing the treated populations into a compatible subject. The compounds disclosed above may be used alone or in combination with other compounds (e.g., HSC mobilizing agents as disclosed herein) and compositions to enhance the population of stem cells and/or progenitor cells in the peripheral blood.

In accordance with a seventh aspect of the invention, CXCR4 antagonist, e.g., AMD3100 in combination with at least one S1PR1 modulator agent in a specific ratio effective to enhance the mobilization of HSCs, may be used to treat hematopoietic cells in vitro or in vivo. In addition, while the agents in combination act to stimulate or enhance mobilization of stem or progenitor cells from the bone marrow to the blood compartment, the agents when used together may or may not act to increase the rate of hematopoietic stem or progenitor cellular multiplication, self-renewal, expansion, and proliferation. This may for example be useful in some embodiments for in vitro hematopoietic cell cultures used in bone marrow transplantation, peripheral blood mobilization, or ex vivo use, for example, in some embodiments involving the treatment of human diseases such as a cancer. The hematopoietic cells targeted by the methods of the invention may include hematopoietic progenitor or stem cells.

The CXCR4 antagonist, e.g., AMD3100 in combination with at least one S1PR1 modulator agent in a specific ratio effective to enhance the mobilization of HSCs and methods of the invention are also contemplated for use in mobilizing or enhancing egress of quiescent cancer stem cells from their niche in the microenvironment or in a tumor mass to the circulation or to distant organs or tissues such that the cancer stem cells are put into an activated or proliferative state in order to make them more susceptible to cytoreductive therapy, which generally targets actively dividing cells. Once they are in such an activated or proliferative state, one may administer a cytoreductive therapy in the form of a chemotherapeutic drug or radiotherapy.

In alternative embodiments, the use of CXCR4 antagonist, e.g., AMD3100 in combination with at least one S1PR1 modulator agent in a specific ratio effective to enhance the mobilization of HSCs can be used to treat a variety of hematopoietic cells, and such cells may be isolated or may form only part of a treated cell population in vivo or in vitro. Cells amenable to treatment with the combination of a CXCR4 antagonist, e.g., AMD3100 in combination with at least one S1PR1 modulator agent in a specific ratio effective to enhance the mobilization of HSCs can be used for cells such as, for example, all cells in the hematopoietic lineage, beginning with pluripotent stem cells, such as bone marrow stem or progenitor cells, lymphoid stem or progenitor cells, myeloid stem cells, cancer stem cells, CFU-GEMM cells (colony-forming-unit granulocyte, erythroid, macrophage, megakaryocye), pre-B cells, prothymocyte), BFU-E cells (burst-forming unit-erythroid), BFU-MK cells (burst-forming unit megakaryocytes), CFU-GM cells (colony-forming unit-granulocyte-macrophage-), CFU-bas cells (colony-forming unit-basophil), CFU-Mast cells (colony forming unit mast cell), CFU-G cells (colony forming unit granulocyte), CFU-M/DC cells (colony forming unit monocyte/dendritic cell), CFU-Eo cells (colony forming unit eosinophil), CFU-E cells (colony forming unit erythroid), CFU-MK cells (colony forming unit megakaryocyte), myeloblasts, monoblasts, B-lymphoblasts, T-lymphoblasts, proerythroblasts, neutrophillic myelocytes, promonocytes, or other hematopoietic cells that differentiate to give rise to mature cells such as macrophages, myeloid related dendritic cells, mast cells, plasma cells, erythrocytes, platelets, neutrophils, monocytes, eosinophils, basophils, B-cells, T-cells or lymphoid related dendritic cells.

In another embodiment, the invention provides methods of increasing the circulation of hematopoietic cells by mobilizing them from the marrow to the peripheral blood comprising administering an effective amount of an CXCR4 antagonist, e.g., AMD3100 in combination with at least one S1PR1 modulator agent in a specific ratio effective to enhance the mobilization of HSCs to cells of a patient undergoing autologous mobilization where hematopoietic stem/progenitor cells may be mobilized into the peripheral blood (1) during the rebound phase of the leukocytes and/or platelets after transient granulocytopenia and thrombocytopenia induced by myelosuppressive chemotherapy, (2) by hematopoietic growth factors, or (3) by a combination of both. Such treatment may for example be carried out so as to be effective to mobilize the hematopoietic cells from a marrow locus (i.e. a location in the bone marrow) to a peripheral blood locus (i.e. a location in the peripheral blood). Such treatments may for example be undertaken in the context of or for the clinical procedure of leukapheresis or apheresis.

In alternative embodiments, a combination of CXCR4 antagonist, e.g., AMD3100 in combination with at least one S1PR1 modulator agent in a specific ratio effective to enhance the mobilization of HSCs can be used in ex vivo stem cell expansion to supplement stem cell grafts with more immature precursors to shorten or potentially prevent hematopoietic cell depletion, including conditions such as pancytopenia, granulocytopenia, thrombocytopenia, anemia or a combination thereof; to increase the number of primitive progenitors to help ensure hematopoietic support for multiple cycles of high-dose therapy; to obtain sufficient number of stem cells from a single apheresis procedure, thus reducing the need for large-scale harvesting of marrow OR multiple leukopheresis; to generate sufficient cells from a single cord-blood unit to allow reconstitution in an adult after high-dose chemotherapy; to purge stem cell products of contaminating tumour cells; to generate large volumes of immunologically active cells with antitumour activity to be used in immunotherapeutic regimens or to increase the pool of stem cells that could be targets for the delivery of gene therapy.

Alternatively, a combination of CXCR4 antagonist, e.g., AMD3100 in combination with at least one S1PR1 modulator agent in a specific ratio effective to enhance the engraftment of HSCs can be used in ex vivo stem cell culture to prime the cells for enhanced engraftment prior to transplantation into a recipient subject.

In alternative embodiments, the invention provides methods using a combination a CXCR4 antagonist, e.g., AMD3100 with at least one S1PR1 modulator agent in a specific ratio effective to enhance the mobilization to treat stem cells ex vivo to enrich hematopoietic progenitor cells which are utilized in bone marrow (BM) and peripheral blood (PB) stem cell transplantation, wherein the hematopoietic stem cell transplantation (HSCT) protocols may for example be utilized for the purpose of treating the following diseases (from Ball, E. D., Lister, J., and Law, P. Hematopoietic Stem Cell Therapy, Churchill Livingston (of Harcourt Inc.), New York (2000)): Aplastic Anemia; Acute Lymphoblastic Anemia.; Acute Myelogenous Leukemia; Myelodysplasia; Multiple Myeloma; Chronic Lymphocytic Leukemia; Congenital Immunodeficiencies (such as Autoimmune Lymphoproliferative disease, Wiscott-Aldrich Syndrome, X-linked Lymphoproliferative disease, Chronic Granulamatous disease, Kostmann Neutropenia, Leukocyte Adhesion Deficiency); Metabolic Diseases (for instance those which have been HSCT indicated such as Hurler Syndrome (MPS I/II), Sly NW Syndrome (MPS VII), Childhood onset cerebral X-adrenoleukodystrophy, Globard cell Leukodystrophy).

Another aspect of the invention provides methods of preventing the migration of a stem cell from its niche in a tissue, or for retaining the stem cell within its niche in the tissue, the method comprising treating a subject with an effective amount of a combination of CXCR4 antagonist, e.g., AMD3100 in combination with at least one S1PR1 modulator agent in a specific ratio effective to enhance the engraftment of HSCs.

Although the CXCR4 antagonist AMD3100 is known for HSPC mobilization, its effects are limited and an improved protocol would be beneficial. Herein, the inventors demonstrate that the combination of AMD3100 with any one of W146, FTY720, or SEQ2871 in specific ratios improves mobilization of HSC from the bone marrow in vivo.

Additionally, although SIP receptor agonist (i.e. FTY720) has been reported to be administered to patients as an immunosuppressant due to its ability to block lymphocyte egress, FTY720 has not been shown to promote HSC migration and/or enhance HSC engraftment. Additionally, while S1P has previously been reported to have a role in HSPC trafficking (Massberg et al. Cell 2007 vol. 131 (5) pp. 994-1008), Massberg et al., demonstrated the opposite of the present invention, and in particular, Massberg et al., reported that FTY720 blocked HSC egress from tissues. Herein the inventors demonstrate that in a 5:1 ratio of FTY720:

AMD3100, FTY720 can function to promote migration of HSC from the bone marrow, and in a 3:1 ratio of FTY720: AMD3100, FTY720 can promote and enhance HSC engraftment.

Accordingly, the inventors have demonstrated optimal dose ratios of S1PR1 (S1P receptor 1) antagonist (W146) or S1PR1 agonist (FTY720, SEW2871, or AUY954) with a CXCR4 antagonist (AMD3100) to increase bone marrow mobilization, homing, and engraftment hematopoietic stem/progenitor cells in mammals, e.g., humans. Accordingly, the present invention provides methods and improvements to existing clinical transplantation protocols, both for mobilization of stem cells in donors, and engraftment of stem cells in recipients.

One embodiment provides a method for promoting hematopoietic stem cell growth in a subject, comprising administering at least one hematopoietic stem cell (HSC) modulator and a pharmaceutically acceptable carrier.

The method of the invention to promote HSCs mobilization and HSCs engraftment as disclosed herein provides one or more of the following benefits: (1) allows transplantation to proceed in patients who would not otherwise be considered as candidates because of the unacceptably high risk of failed engraftment; (2) reduces the number of aphereses required to generate a minimum acceptable harvest; (3) reduces the incidence of primary and secondary failure of engraftment by promoting engraftment and/or by increasing the number HSCs available for transplantation; and (4) reduces the time required for primary engraftment by increasing the number of committed precursors of the important hemopoietic lineages.

The combination of a CXCR4 antagonist and at least one S1PR1 modulator agent in either (i) a specific ratio effective to increase HSC engraftment or (ii) a specific ratio effective to increase HSC mobilization as disclosed herein can have the clinical benefits in stem cell transplantation of improvement of apheresis yields and improvement of the engraftment potential of aphereed cells.

The combination of a CXCR4 antagonist and at least one S1PR1 modulator agent in either (i) a specific ratio effective to increase HSC engraftment may also be of use in treating subjects suffering from hyperproliferative disorders of the hematopoietic system. Hyperproliferative disorders may include, but are not limited to, polycythemia vera, essential thrombocythemia, myelofibrosis with myeloid metaplasia, and chronic myelogenous leukemia.

In another embodiment, the pharmaceutical composition further comprises a chemotherapeutic agent. In yet another embodiment, the pharmaceutical composition is administered before, during or after chemotherapy or irradiation therapy in a patient suffering from a cancerous condition or a hyperproliferative disorder. In another embodiment, the pharmaceutical composition is used as adjunct therapy for treating a cancerous condition or a hyperproliferative disorder.

Other objects and advantages will become apparent to those skilled in the art from a review of the following description which proceeds with reference to the following illustrative drawings.

DESCRIPTION OF THE DRAWINGS

FIG. 1A-1G shows endothelial cell cuddling in zebrafish and mouse embryo hematopoietic tissues. FIG. 1A is a diagram of a 38 hpf zebrafish embryo with CHT marked (red box). FIG. 1B shows CHT of ~46 hpf Runx1+23:EGFP; kdrl:DsRed2 embryo (HSPCs green; endothelial cells red). Caudal artery (CA), circulation to posterior (right). Caudal vein (CV), circulation to anterior (left). White box marks detail. FIG. 1C shows HSPC (arrow) extravasates in <10 minutes by squeezing through endothelial wall. Endothelial niche will form in broken circle.

FIG. 1D shows endothelial cells remodel around HSPC. FIG. 1E shows HSPC asymmetrically divides, daughter cell migrates away, and single HSPC is left in niche. FIG. 1F shows similar events are observed in E11 mouse feta liver (FL) explant. White box marks detail. FIG. 1G shows a single c-kit-APC+HSPC (magenta) moves into group of CD31-FITC+endothelial cells (green), which closely associate with HSPC. FIG. 1H shows E12.5 embryos, showing the number of c-kit-APC+cells in the FL has expanded.

FIGS. 2A-2H show expression of cmyb/runx1 in CHT of 72 hpf embryos after chemical treatment from 48 hpf (anterior view shown in FIGS. 2A, 2C, 2E and 2G, ventral view shown in FIGS. 2B, 2D, 2F and 2H). FIGS. 2A-2D show CXCR4 antagonist AMD3100 dose-dependently reduces cmyb/runx1 in the CHT. FIG. 2E shows S1P alters cmyb/runx1 expression pattern. FIG. 2F shows S1PR1 agonist FTY720 (5 µM) has little effect alone. FIG. 2G shows when FTY720 (5µM) is combined with AMD3100 (15µM) it can increase CHT hematopoiesis. FIG. 2H shows that with FTY720 and increased AMD3100 dose, CHT hematopoiesis is greatly reduced. FIG. 2R shows a graph illustrating the scoring protocol for individual embryos as having low, intermediate, or high cmyb/runx1 expression. The panel number is shown below each bar in the graph and the number of embryos scored is in brackets. Taken together, these results demonstrate an overall trend (i.e. increase, decrease, or no change) for a given treatment condition. Scoring results are shown together for FIG. 2A-2H and FIG. 2J-2Q.

FIG. 3A-3B shows s1pr1 morpholino knockdown reduced runx1 expression in CHT at 54 hpf (FIG. 3B), as compared to control morpholino (FIG. 3A). FIG. 3C-3D show s1pr1 knockdown in cmyb:EGFP; kdrl:DsRed2 background increased cmyb+ progenitors in CHT at 36 hpf (FIG. 3D), compared to uninjected control (FIG. 3C). FIG. 3E-3G show lineage tracing of HSPCs from DA to CHT (cd41:

EGFP and uncaged FITC)). S1PR1 antagonist W146 (10 μM) increased cell number and produced morphological changes (FIG. 3F) compared to control (FIG. 3E). FIG. 3G show the number of lineage traced HSPCs in the CHT (n=12-15 embryos scored; *Student's t-test, p=0.0001). FIG. 3H-3L show the results of live cell tracking from CHT time-lapse (38-50 hpf). Control group (n=4) versus W146 (10 μM) treatment group (n=3). FIG. 3K-3L show cumulative cell tracking events after 12 h from representative control (FIG. 3K) or treatment (FIG. 3L) movie. Note: FIGS. 3H, 3L, the number of tracks scored is not an absolute measure of cell number, as one cell could migrate in and out of the scoring field, creating multiple tracks. Graphs show mean±s.e.m.

FIGS. 4A-4D show S1PR1 has a cell autonomous role in HSPCs during CHT seeding. FIGS. 4A-4D show Live imaging of HSPCs in the CHT with WT or DN-S1PR1-mCherry cDNA fusions over-expressed with the Runx1+23 enhancer. To confirm HSPC specificity, DN-S1PR1-mCherry was over-expressed in cd41:EGFP (FIG. 4A) and cmyb:EGFP (FIG. 4B) backgrounds ((i) merge; (ii) EGFP; (iii) mCherry)). FIG. 4C-4D show single frames from higher magnification live imaging of HSPCs in the CHT at ~60 hpf with WT (FIG. 4C) or DN (FIG. 4D) S1PR1-mCherry expressed.

FIGS. 5A-5P show the characterization of stable Runx1+23:EGFP and Runx1+23:NLS-mCherry transgenic zebrafish lines. FIG. 5A shows the intercross of Runx1+23:EGFP and Runx1+23:NLS-mCherry lines to show overlapping expression in the CHT (white arrowheads). FIG. 5B shows Runx1+23:EGFP; kdrl:DsRed2 shows Runx1+23 positive cells (green) in the DA (asterisks). DA is DA and the arrow marks circulation away from the heart. PCV is the posterior cardinal vein and the arrow marks circulation towards the heart. FIG. 5C shows Runx1+23:EGFP; flk1:DsRed2 shows Runx1+23 positive cells (green) in the vascular plexus of the CHT. CA and CV are as in FIG. 1. FIG. 5D shows Runx1+23:NLS-mCherry; mpx:EGFP shows Runx1+23 positive cells (red; white arrowheads) are a distinct population from EGFP+neutrophils (green). Low level expression of Runx1+23 positive nuclei in neutrophils is often observed, consistent with dilution of fluorescent protein upon differentiation of an HSPC. Co-expression at stages and in embryonic sites of hematopoiesis, as marked: FIGS. 5E, 5F, 5I, 5J, 5M and 5N show Runx1+23:NLS-mCherry; cd41:EGFP; FIGS. 5G, 5H, 5K, 5L, 5O and 5P show Runx1+23:NLS-mCherry; cmyb:EGFP. FIGS. 5N and 5P show dotted line marks the anterior head kidney in the 5 dpf larva.

FIG. 6A shows the merged image, FIG. 6B shows FITC expression, FIG. 6C shows mCherry expression and FIG. 6D shows nuclei. White arrowheads mark triple positive cells. Asterisks mark triple positive cells ventral to and outside of the CHT that are probably migratory myeloid cells.

FIG. 7A shows FSC and SSC were used to distinguish characteristic populations: erythrocyte, myeloid, lymphoid, precursor[35]. Runx1+23:NLS-mCherry positive cells made up approximately 4-5% of WKM and were found predominately in the lymphoid gate, consistent with HSPCs having morphology similar to this population. FIG. 7B shows embryo-to-embryo transplantation was performed by injection of mCherry positive cells sorted from Runx1+23:NLS-mCherry 3 dpf embryos into 2 dpf recipients (mixed clutch of runx1 W84X +/− and −/− embryos). Recipients were grown to 10 weeks and their WKM was sorted for engraftment of mCherry positive cells. A typical FACS plot is shown for one of the recipients. n=6/6 tested recipients were positive for transplanted mCherry cells at a percentage of 2-5%, which was similar to the WKM of stable adult Runx1+23:NLS-mCherry transgenic fish.

FIGS. 8A-8B shows whole mount expression patterns of cxcr4a, cxcr4b, cxcl12a, cxcl12b at 36, 48 and 72 hpf. FIG. 8A shows cxcr4a expression, FIG. 8B shows cxcr4b expression, FIG. 8C shows cxcl12a expression, FIG. 8D shows cxcl12b expression. Details of DA and CHT are shown for each example. All genes are expressed in the head and lateral line. cxcr4b but not cxcr4a is expressed in the CHT at 36 hpf. cxcl12a and cxcl12b are expressed in the DA and CHT from 30 hpf (not shown) through to 48 hpf.

FIGS. 7A and 9B are the merged image, FIGS. 9C, 9D show cxcl12a:DsRed2 expression. FIGS. 9E, 9F show kdrl:EGFP expression. FIGS. 9B, 9D and 9F are high magnification images of the image in the white box in 9A for panels 9A, 9C and 9E respectively.

FIG. 10 shows combinatorial chemical genetics to address the role of S1P and CXCR4-CXCL12 signaling pathways in CHT hematopoiesis. FIG. 10 is a continuation of FIG. 2 and should be compared for the control (FIG. 2A) and AMD3100 alone doses 15 μM (FIG. 2B-2D).

FIG. 11A shows untreated control, and FIG. 11B shows AUY954 only treated control. FIG. 11C shows 25 μM dose of AMD3100 greatly decreases cmyb/runx1 expression. Interestingly, this effect is partially rescued by addition of the S1PR1 agonist AUY954 (FIG. 11D). Addition of sphingosine kinase inhibitor 2 (SKI-2) at a 25 μM dose has the effect of depleting endogenous levels of S1P (FIG. 11E). This effect can be rescued by addition of S1PR1 agonist AUY954 (FIG. 11F). S1PR1 antagonist W146 at a 25 μM dose decreases cmyb/runx1 expression in the CHT (FIG. 11G). The effect of W146 can be rescued by addition of AUY954 (FIG. 11H) or S1P (FIG. 11J). Higher doses of S1PR1 agonists are known to function as functional antagonists, as was also observed (FIG. 11I). All panels show cmyb/runx1 expression in the CHT region of 54 hpf embryos. FIG. 11K shows the scoring protocol is as in 11.

FIG. 12A shows the expression of kdrl at 36 hpf in uninjected controls and FIG. 12B shows the expression of kdr1 of injection of 2 ng s1pr1 demonstrating that vascular patterning is not affected.

FIG. 13A shows expression patterns of cxcr4a, cxcr4b, cxcl12a, cxcl12b at 36, 48 and 72 hpf. FIG. 13B shows immunostaining with anti-CXCR4 in the CHT at 48 hpf.

FIG. 15A shows the method of the chemical screen, FIG. 15B shows a summary of the hits identified from the screen. Now that we had a model for CHT colonization, we wanted to better understand the mechanisms of CHT colonization. The chemical genetic screen was performed during the peak window of CHT colonization. Mass spawnings allowed collection of 1000s of stage matched embryos which were used to screen a library of 2400 chemicals by soaking embryos for 24 h. In situ hybridization on treated embryos was performed for the hematopoietic progenitor markers cymb and runx1. EET compound was used as a positive control for increased CHT hematopoiesis. AMD3100 was used as a negative control for decreased CHT hematopoiesis. The test compound were scored against these two controls. Sphingosine, a bioactive lipid with a known role in cell migration was identified from this screen.

FIG. 16A shows s1pr1 expression by hybridization, FIG. 16B shows expression as detected by immunostaining in the AGM at 36 hpf.

FIG. 17A shows the S1P1 kinase inhibitor, SKI-2 has little effect on improving engraftment. FIG. 17B shows engraftment grid matrix of increasing doses of SKI-2 in the presence of increasing concentrations of S1PR1 agonist AUY954. FIG. 17C shows engraftment grid matrix in the presence of increasing concentrations of S1PR1 antagonist W146. S1PR1-dependent thymocyte migration dynamics with increasing S1P concentrations.

FIG. 18 shows effect of increasing dose of CXCR4 antagonist AMD3100 with increasing dose of W146 antagonist on engraftment, showing greatest CHT score with 5 µM AMD3100 and 10 µM W146. The red box indicates an observation of an increased migratory phenotype of myeloid progenitor cells (e.g. neutrophils and macrophages) as shown by whole mount in situ hybridization of cmyb/runx1 probes. This can be interpreted as an indicator of mobilization or engraftment, as well as a general activation of hematopoietic progenitors within the embryo. The red arrows in FIG. 18 indicate the column (or fixed dose) of S1PR1 agonist in the zebrafish assay that is optimal for titration against AMD3100 for maximal engraftment.

FIG. 19A-19B show S1PR1 agonists chemically interacts with CXCR4 antagonist. FIG. 19A shows effect of increasing dose of CXCR4 antagonist with increasing dose of AUY954 on HSC engraftment, showing greatest engraftment with a +2 CHT score with 10 µM AMD3100 and 12.5 µM AUY945 (as shown by the arrow). FIG. 19B shows effect of increasing dose of CXCR4 antagonist with increasing dose of FTY720 on HSC engraftment, showing greatest engraftment with a +2 CHT score with 15 µM AMD3100 and 5 µM FTY720 (as shown by the arrow).

FIG. 25 shows live imaging of stages of CHT colonization. By breaking down these time-lapse movies into single frames, discrete stages of CHT colonization were identified; attachment and extravasation, endothelial cuddling, and asymmetric cell division. Cells that arrive in the CHT and adhere to endothelial cells undergo extravasation—or squeeze through the endothelial wall to arrive on the abluminal side of the vessel once there, the HSPC will interact with other endothelial cells that create a niche or pocket—a process herein referred to as "endothelial cuddling". Once in this niche, the HSC will either a) remain quiescent, b) divide symmetrically to create 2 HSPCs, or c) divide asymmetrically to create an HSPC and a more differentiated cell. An asymmetric cell division is shown here: one cell in the pocket divides into two, then one of the two cells, probably a myeloid progenitor, crawls out of away from the pocket.

FIG. 26A shows s1pr1 expression pattern by in situ hybridization. FIG. 26B shows the controls; s1pr1 knockdown control and the cymba and runx1. Accordingly, the bioactive lipid S1P produced an effect in the in vivo CHT colonization assay. The inventors assessed the expression pattern of s1pr1 receptor during the key stages of HSPC emergence and discovered that it is expressed in both the DA and the CHT. Importantly, morpholino knockdown of the receptor in the embryo results in a significant decrease in hematopoietic progenitor markers cmyb and runx1 (FIG. 26B). A similar phenotype results from treatment of the embryos with a s1pr1-specific chemical antagonist.

FIG. 28 shows overexpression of dominant negative S1PR1 in HSC interferes with CHT colonization. Using the same runx1 enhancer, a dominant negative version of the S1PR1 receptors was transiently overexpressed in a different zebrafish background which marks HSCs, cmyb-GFP, and used in the live imaging assay. Using time-lapse live imaging, it was determined that one end of the cell tries to adhere to the endothelial wall, but does not undergo extravasation or migration to the abluminal side of the vessel. After the cell fails to engraft, it migrates away as a presumptive myeloid progenitor. Accordingly, the inventors have demonstrated a cell-autonomous role for S1PR1 in HSC engraftment once they arrive in the CHT and is important for colonization of this hematopoietic niche in the embryo.

DETAILED DESCRIPTION

Figure 1A:
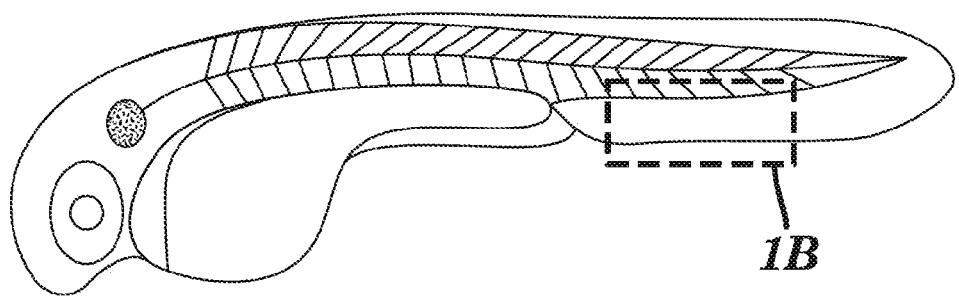
Figure 1B:
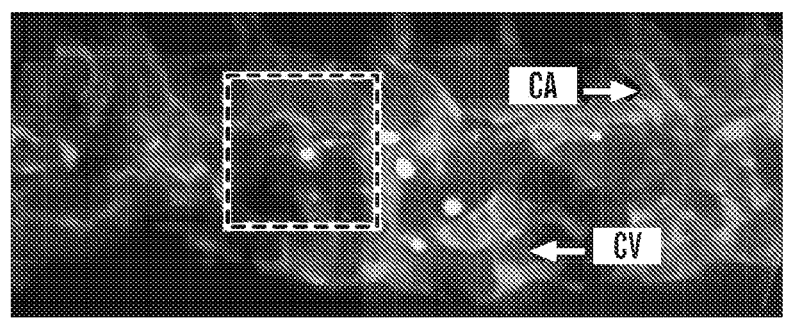

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Definitions

The terms used herein have the meanings recognized and known to those of skill in the art, however, for convenience and completeness, particular terms and their meanings are set forth below.

The term "agent" as used herein refers to all materials that may be used to prepare pharmaceutical and diagnostic compositions, or that may be compounds such as small synthetic or naturally derived organic compounds, nucleic acids, polypeptides, antibodies, fragments, isoforms, variants, or other materials that may be used independently for such purposes, all in accordance with the present invention.

The term "agonist" refers to an agent that mimics or up-regulates (e.g., potentiates or supplements) the bioactivity of a protein. An agonist may be a wild-type protein or derivative thereof having at least one bioactivity of the wild-type protein. An agonist may also be a compound that up-regulates expression of a gene or which increases at least one bioactivity of a protein. An agonist may also be a compound which increases the interaction of a polypeptide with another molecule, e.g., a target peptide or nucleic acid.

The term "antagonist" refers to an agent that down-regulates (e.g., suppresses or inhibits) at least one bioactivity of a protein. An antagonist may be a compound which inhibits or decreases the interaction between a protein and another molecule, e.g., a target peptide or enzyme substrate. An antagonist may also be a compound that down-regulates expression of a gene or which reduces the amount of expressed protein present.

In some embodiments, an antagonist is a functional antagonist. The term "functional antagonist" as used herein refers to S1PR1 modulator agent (agonist or antagonist) which decreases the activity of the S1PR1 protein. In some embodiments, S1PR1 modulating agents previously classified as S1PR1 agonists can function as "functional S1PR1 antagonists" herein at higher doses because they force internalization of the target receptor, thereby making the cell unresponsive to the signal. Accordingly, the action of "functional antagonists" and the internalization of the target receptor contribute to the unexpected response curves associated with some of these drugs.

The term "small molecule" refers to a composition that has a molecular weight of less than 3 kilodaltons (kDa), and preferably less than 1.5 kilodaltons, and more preferably less than about 1 kilodalton. Small molecules may be nucleic acids, peptides, polypeptides, peptidomimetics, carbohydrates, lipids or other organic (carbon-containing) or inorganic molecules. As those skilled in the art will appreciate, based on the present description, extensive libraries of chemical and/or biological mixtures, often fungal, bacterial, or algal extracts, may be screened with any of the assays of the invention to identify compounds that modulate a bioactivity. A "small organic molecule" is an organic compound (or organic compound complexed with an inorganic compound (e.g., metal)) that has a molecular weight of less than 3 kilodaltons, and preferably less than 1.5 kilodaltons, and more preferably less than about 1 kDa.

The concept of "combination therapy" is well exploited in current medical practice. Treatment of a pathology by combining two or more agents that target the same pathogen or biochemical pathway sometimes results in greater efficacy and diminished side effects relative to the use of the therapeutically relevant dose of each agent alone. In some cases, the efficacy of the drug combination is additive (the efficacy of the combination is approximately equal to the sum of the effects of each drug alone), but in other cases the effect can be synergistic (the efficacy of the combination is greater than the sum of the effects of each drug given alone). As used herein, the term "combination therapy" means the two compounds can be delivered in a simultaneous manner, e.g. concurrently, or wherein one of the compounds is administered first, followed by the second agent, e.g. sequentially. The desired result can be either a subjective relief of one or more symptoms or an objectively identifiable improvement in the recipient of the dosage.

The term "modulation" or "modulates" or "modulating" refers to up regulation (i.e., activation or stimulation), down regulation (i.e., inhibition or suppression) of a response, or the two in combination or apart.

The term "S1PR1 modulator agent" as disclosed herein encompasses both S1PR1 agonists and S1PR1 antagonists, where an S1PR1 agonist refers to an agent which can activate or stimulate S1PR1 function, and a S1PR1 antagonist refers to an agent which can inhibit the S1PR1 response.

The term "treatment" or "treating" refers to therapy, prevention and prophylaxis and particularly refers to the administration of medicine or the performance of medical procedures with respect to a patient, for either prophylaxis (prevention) or to cure or reduce the extent of or likelihood of occurrence of the infirmity or malady or condition or event in the instance where the patient is afflicted. In the present invention, the treatments using the agents described may be provided to treat patients suffering from a cancerous condition or hyperproliferative disease, whereby the treatment of the disease with chemotherapy or irradiation therapy results in a decrease in bone marrow cellularity, thus making the patient more prone to acquiring infectious agents or diseases. Thus, the administration of a CXCR4 antagonist with a S1PR1 modulator agent at a specific ratio effective to enhance mobilization of HSCs or progenitor cells from the bone marrow to the peripheral blood. Most preferably, the treating is for the purpose of reducing or diminishing the symptoms or progression of a cancerous disease or disorder by allowing for the use of accelerated doses of chemotherapy or irradiation therapy.

The term "subject" or "patient" refers to a mammal, preferably a human, in need of treatment for a condition, disorder or disease.

The term "prophylactic" or "therapeutic" treatment refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

A "mobilizer of HSCs" or "mobilizer agent", (used interchangeably herein) as described herein refers to any compound, whether it is a small organic molecule, synthetic or naturally derived, or a polypeptide, such as a growth factor or colony stimulating factor or an active fragment or mimic thereof, a nucleic acid, a carbohydrate, an antibody, or any other agent that acts to enhance the migration of stem cells from the bone marrow into the peripheral blood. Such a "mobilizer" may increase the number of hematopoietic stem cells or hematopoietic progenitor/precursor cells in the peripheral blood, thus allowing for a more accessible source of stem cells for use in transplantation.

The term "stem Cells" as used herein refers to cells, which are not terminally differentiated and are therefore able to produce cells of other types. Stem cells are divided into three types, including totipotent, pluripotent, and multipotent. "Totipotent stem cells" can grow and differentiate into any cell in the body, and thus can grow into an entire organism. These cells are not capable of self-renewal. In mammals, only the zygote and early embryonic cells are totipotent. "Pluripotent stem cells" are true stem cells, with the potential to make any differentiated cell in the body, but cannot contribute to making the extra embryonic membranes (which are derived from the trophoblast).

"Multipotent stem cells" are clonal cells that self-renew as well as differentiate to regenerate adult tissues. "Multipotent stem cells" are also referred to as "unipotent" and can only become particular types of cells, such as blood cells or bone cells. The term "stem cells", as used herein, refers to pluripotent stem cells capable of self-renewal.

The term "cancer stem cells" refers to a small population of cells that are quiescent, which are capable of self-renewal, and which appear to be the source of cells comprising a malignant and/or metastatic tumor.

The term "niche" as used herein refers to a small zone within the microenvironment of a stem cell that maintains and controls stem cell activity in several organs.

The term "adult stem cells" refers to cells which can be found in adult beings. Adult stem cells reproduce daily to provide certain specialized cells, for example 200 billion red blood cells are created each day in the body. Until recently it was thought that each of these cells could produce just one particular type of cell. This is called differentiation. However, in the past few years, evidence has been gathered of stem cells that can transform into several different forms. Bone marrow stem cells are known to be able to transform into liver, nerve, muscle and kidney cells. Stem cells isolated from the bone marrow have been found to be pluripotent. Useful sources of adult stem cells are found in organs throughout the body. In the same way that organs can be transplanted from cadavers, researchers have found that these could be used as a source of stem cells as well. Taking stem cells from the brains of corpses they were able to coax them into dividing into valuable neurons.

The term "hematopoiesis" refers to the highly orchestrated process of blood cell development and homeostasis. Prenatally, hematopoiesis occurs in the yolk sack, then liver, and eventually the bone marrow. In normal adults it occurs in bone marrow and lymphatic tissues. All blood cells develop from pluripotent stem cells. Pluripotent cells differentiate into stem cells that are committed to three, two or one hematopoietic differentiation pathway. None of these stem cells are morphologically distinguishable, however.

The term "hematopoietic stem cells" as used in the present invention means multipotent stem cells that are capable of differentiating into all blood cells including erythrocytes, leukocytes and platelets. For instance, the "hematopoietic stem cells" as used in the invention are contained not only in bone marrow but also in umbilical cord blood derived cells.

The term "hematopoietic progenitors", which is used interchangeably with the term "hematopoietic precursors", refers to those progenitor or precursor cells which are differentiated further than hematopoietic stem cells but have yet to differentiate into progenitors or precursors of respective blood cell lineages (unipotent precursor cells). Thus, "progenitor cell(s)" or "precursor cell(s)" are defined as cells that are lineage-committed, i.e., an individual cell can give rise to progeny limited to a single lineage such as the myeloid or lymphoid lineage. They do not have self-renewal properties. They can also be stimulated by lineage-specific growth factors to proliferate. If activated to proliferate, progenitor cells have life-spans limited to 50-70 cell doublings before programmed cell senescence and death occurs. For example, the "hematopoietic progenitors" as used in the present invention include granulocyte/macrophage associated progenitors (colony-forming unit granulocyte, macrophage, CFU-GM), erythroid associated progenitors (burst-forming unit erythroid, BFU-E), megakaryocyte associated progenitors (colony-forming unit megakaryocyte, CFU-Mk), and myeloid associated stem cells (colony-forming unit mixed, CFU-Mix). Hematopoietic progenitor cells possess the ability to differentiate into a final cell type directly or indirectly through a particular developmental lineage. Undifferentiated, pluripotent progenitor cells that are not committed to any lineage are referred to herein as "stem cells." All hematopoietic cells can in theory be derived from a single stem cell, which is also able to perpetuate the stem cell lineage, as daughter cells become differentiated. The isolation of populations of mammalian bone marrow cell populations which are enriched to a greater or lesser extent in pluripotent stem cells has been reported (see for example, C. Verfaillie et al., J. Exp. Med., 172, 509 (1990), incorporated herein by reference).

The term "differentiation" of hematopoietic stem cells and/or hematopoietic progenitors as used in the invention means both the change of hematopoietic stem cells into hematopoietic progenitors and the change of hematopoietic progenitors into unipotent hematopoietic progenitors and/or cells having characteristic functions, namely mature cells including erythrocytes, leukocytes and megakaryocytes. Differentiation of hematopoietic stem cells into a variety of blood cell types involves sequential activation or silencing of several sets of genes. Hematopoietic stem cells choose either a lymphoid or myeloid lineage pathway at an early stage of differentiation.

The term "clonal progenitors or CFU-c" refers to a colony forming unit culture, in which granulocyte-macrophage progenitor cells are identified by their ability to give rise to monoclonal colonies in the presence of appropriate stimulators in vitro.

The term "chemokines" (chemoattractant cytokines) are a family of homologous serum proteins of between 7 and 16 kDa, which were originally characterized by their ability to induce migration of leukocytes. Most chemokines have four characteristic cysteines (Cys), and depending on the motif displayed by the first two cysteines, they have been classified into CXC or alpha, CC or beta, C or gamma, and CX3C or delta chemokine classes. Two disulfide bonds are formed between the first and third cysteines and between the second and fourth cysteines. Clark-Lewis and co-workers reported that, at least for IL-8, the disulfide bridges are critical for chemokine activity (Clark-Lewis et al., J. Biol. Chem. 269:16075-16081, 1994). The only exception to the four cysteine motif is lymphotactin, which has only two cysteine residues. Thus, lymphotactin retains a functional structure with only one disulfide bond.

In addition, the CXC, or alpha, subfamily has been divided into two groups depending on the presence of the ELR motif (Glu-Leu-Arg) preceding the first cysteine: the ELR-CXC chemokines and the non-ELR-CXC chemokines (see, e.g., Clark-Lewis, supra, and Belperio et al., "CXC Chemokines in Angiogenesis," J. Leukoc. Biol. 68:1-8, 2000). ELR-CXC chemokines, such as IL-8, are generally strong neutrophil chemoattractants while non-ELR chemokines, such as IP-10, and SDF-1, predominantly recruit lymphocytes. CC chemokines, such as RANTES, MIP-1-alpha, MCP-1, generally function as chemoattractants for monocytes, basophils, eosinophils, and T-cells but not neutrophils. In general, chemokines are chemotactic agents that recruit leukocytes to the sites of injuries.

The term "SDF-1" is also known as stromal cell-derived factor-1 or"CXCL12", and are used interchangeably herein refers to a CXC chemokine that demonstrates in vitro activity with respect to lymphocytes and monocytes but not neutrophils. It is highly potent in vivo as a chemoattractant for mononuclear cells. SDF-1 has been shown to induce intracellular actin polymerization in lymphocytes, and to induce a transient elevation of cytoplasmic calcium in some cells. By "function of a chemokine, CXCL12" is meant the binding of the chemokine to its receptor and the subsequent effects on signaling. The nucleic acid sequence of the human CXCL12 is found in the following GenBank Accession numbers: NM_000609; NM_001033886; NM_199168; BC039893; AY644456; AY802782 and CR450283. The protein sequence of the human CXC chemokine, CXCL12 or SDF-1, is shown below as SEQ ID NO:1: Lys-Pro-Val-Ser-Leu-Ser-Tyr-Arg-Cys-Pro -Cys-Arg-Phe-Phe-Glu-Ser-His-Val-A-la-Arg-Ala-Asn-Val-Lys-His-Leu-Lys-Ile-Leu-Asn-Thr-Pro -Asn-Cys-Ala-Leu-Gln- -I-le-Val-Ala-Arg-Leu-Lys-Asn-Asn-Asn-Arg-Gln-Val-Cys-Ile-As-p-Pro -Lys-Leu- -Lys-Trp-Ile-Gln-Glu-Tyr-Leu-Glu-Lys-Ala-Leu-Asn "Chemokine Receptors" are G-protein coupled seven-transmembrane receptors. Based on the chemokine class they bind, the receptors have been named CXCR1, CXCR2, CXCR3, CXCR4, and CXCR5 (all of which bind CXC chemokines); CCR1 through CCR9 (all of which bind CC chemokines); XCR1 (which binds the C chemokine, Lptn); and CX3CR1 (which binds the CX3C chemokine, fractalkine or neurotactin).

Certain "antagonists of CXCR4" have been described in International Publication No. WO 01/85196 A2 entitled "CXCR4 Antagonist Treatment of Hematopoietic Cells" (PCT/CA01/00659. Both PCT publications are hereby incorporated by reference herein, including any drawings, figures and tables. The CXCR4 receptor binds to SDF-1 (CXCL12) ligand. The nucleic acid sequence of human CXCR4 can be found in the following GenBank accession numbers: NM_001008540; Y14739; BC020968; AF052572; and AF025375. The protein sequence of human CXCR4 is shown below as SEQ ID NO: 2: Met Glu Gly Be Ser Ser Ile Pro Leu Pro Leu Leu Gln Ile Tyr Thr Ser Asp Asn Tyr Thr Glu Glu Met Gly Ser Gly Asp Tyr Asp Ser Met Lys Glu Pro Cys Phe Arg Glu Glu Asn Ala Asn Phe Asn Lys Ile Phe Leu Pro Thr Ile Tyr Ser Ile Ile Phe Leu Thr Gly Ile Val Gly-Asn Gly Leu Val Ile Leu Val Met Gly Tyr Gln Lys Lys Leu Arg Ser Met Thr Asp Lys Tyr Arg Leu His Leu Ser Val Ala Asp Leu Leu Phe Val Ile Thr Leu Pro Phe Trp Ala Val Asp Ala Val Ala Asn Trp Tyr Phe Gly Asn Phe Leu Cys Lys Ala Val His Val Ile Tyr Thr Val Asn Leu Tyr Ser Ser Val Leu Ile Leu Ala Phe Ile Ser Leu Asp Arg Tyr Leu Ala Ile Val His Ala Thr
Asn Ser Gln Arg Pro Arg Lys Leu Leu Ala Glu Lys Val Val
Tyr Val Gly Val Trp Ile Pro Ala Leu Leu Leu Thr Ile Pro Asp
Phe Ile Phe Ala Asn Val Ser Glu Ala Asp Asp Arg Tyr Ile Cys
Asp Arg Phe Tyr Pro Asn Asp Leu Trp Val Val Val Phe Gln
Phe Gln His Ile Met Val Gly Leu Ile Leu Pro Gly Ile Val Ile
Leu Ser Cys Tyr Cys Ile Ile Ile Ser Lys Leu Ser His Ser Lys Gly His Gln Lys Arg Lys Ala Leu Lys Thr Thr Val Ile Leu Ile Leu Ala Phe Phe Ala Cys Trp Leu Pro Tyr Tyr Ile Gly Ile Ser Ile Asp Ser Phe Ile Leu Leu Glu Ile Ile Lys Gln Gly Cys Glu Phe Glu Asn Thr Val His Lys Trp Ile Ser Ile Thr Glu Ala Leu Ala Phe Phe His Cys Cys Leu Asn Pro Ile Leu Tyr Ala Phe Leu Gly Ala Lys Phe Lys Thr Ser Ala Gln His Ala Leu Thr Ser Val Ser Arg Gly Ser Ser Leu Lys Ile Leu Ser Lys Gly Lys Arg Gly Gly His Ser Ser Val Ser Thr Glu Ser Glu Ser Ser Ser Phe His Ser Ser

The term "hyperproliferative disease" or "hyperproliferative disorder" as used herein, refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo invasion or metastasis and malignant if it does either of these. A "metastatic" cell means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell.

The term "neoplastic disease," as used herein, refers to any abnormal growth of cells being either benign (non-cancerous) or malignant (cancerous).

The terms "anticancer agent" and "anticancer drug," as used herein, refer to any therapeutic agents (e.g., chemotherapeutic compounds and/or molecular therapeutic compounds), radiation therapies, or surgical interventions, used in the treatment of hyperproliferative diseases such as cancer (e.g., in mammals).

The term "anti-neoplastic agent," as used herein, refers to any compound that retards the proliferation, growth, or spread of a targeted (e.g., malignant) neoplasm The term "analog" as used herein, refers to a chemical compound, a nucleotide, a protein, or a polypeptide that possesses similar or identical activity or function(s) as the chemical compounds, nucleotides, proteins or polypeptides having the desired activity and therapeutic effect of the present invention, but need not necessarily comprise a compound that is similar or identical to those compounds of the preferred embodiment, or possess a structure that is similar or identical to the agents of the present invention.

The term "derivative" refers to the chemical modification of molecules, either synthetic organic molecules or proteins, nucleic acids, or any class of small molecules such as fatty acids, or other small molecules that are prepared either synthetically or isolated from a natural source, such as a plant, that retain at least one function of the active parent molecule, but may be structurally different. Chemical modifications may include, for example, replacement of hydrogen by an alkyl, acyl, or amino group. It may also refer to chemically similar compounds which have been chemically altered to increase bioavailability, absorption, or to decrease toxicity. A derivative polypeptide is one modified by glycosylation, pegylation, or any similar process that retains at least one biological or immunological function of the polypeptide from which it was derived.

As used herein, the term "candidate compound" or "test compound" or "test agent" refers to any compound, molecule or agent that is to be tested. As used herein, the terms, which are used interchangeably, refer to biological or chemical compounds such as simple or complex organic or inorganic molecules, peptides, proteins, oligonucleotides, polynucleotides, carbohydrates, or lipoproteins. A vast array of compounds can be synthesized, for example oligomers, such as oligopeptides and oligonucleotides, and synthetic organic compounds based on various core structures, and these are also included in the terms noted above. In addition, various natural sources can provide compounds for screening, such as plant or animal extracts, and the like. Compounds can be tested singly or in combination with one another. Agents or candidate compounds can be randomly selected or rationally selected or designed. As used herein, an agent or candidate compound is said to be "randomly selected" when the agent is chosen randomly without considering the specific interaction between the agent and the target compound or site. As used herein, an agent is said to be "rationally selected or designed", when the agent is chosen on a nonrandom basis which takes into account the specific interaction between the agent and the target site and/or the conformation in connection with the agent's action.

The phrase "pharmaceutically acceptable" refers to molecular entities and compositions that are physiologically tolerable and do not typically produce an allergic or similar untoward reaction, such as gastric upset, dizziness and the like, when administered to a human Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

Other than in the operating examples, or where otherwise indicated, all numbers expressing quantities of ingredients or reaction conditions used herein should be understood as modified in all instances by the term "about." The term "about" when used in connection with percentages may mean ±1%.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Hematopoietic Stem Cells (HSCs)

Hematopoietic stem cell (HSC) homeostasis it tightly controlled by growth factors, signaling molecules, and transcription factors. Definitive HCSs derived during embryogenesis in the aorta-gonad-mesonephros (AGM) region subsequently colonize the niche in fetal and adult hematopoietic organs. Dzierzak, 12 Curr. Opin. Hematol. 197-202 (2004); Galloway & Zon, 53 Curr. Top. Devel. Biol. 139-58 (2003).

The invention relates to the unexpected finding that the use of a CXCR4 antagonist in combination with certain ratios of S1PR1 modulating agent can enhance the mobilization of the hematopoietic stem cells or progenitor cells from the bone marrow to the peripheral blood, whereas the combination of CXCR4 antagonists with different ratios of S1PR1 modulator agents can enhance or increase engraftment of HSCs from the peripheral blood to the bone marrow.

As such, the combination of a CXCR4 antagonist at least one S1PR1 modulating agent at a specific ratio to promote mobilization of HSCs, can be used alone or in combination with additional mobilizing agents, such as a colony stimulating factor like G-CSF, are of significant value as it allows for the use of lower levels of the colony stimulating factor, thus resulting in significant cost reduction to the patient, as well as shortened hospital stays. Additionally, the methods of the present invention would allow for mobilization of the hematopoietic stem cells from the bone marrow to the circulation, thus allowing for collection of these cells from the patient prior to the onset of, for example, chemotherapy, to be administered back to the patient for autologous transplant.

It is known in the art that several other factors act to increase white blood cells and/or hematopoietic stem cells or progenitor cells in both human and animal subjects. These include granulocyte-macrophage colony stimulating factor (GM-CSF), Interleukin-1 (IL-1), Interleukin-3 (IL-3), Interleukin-8 (IL-8), PIXY-321 (GM-CSF/IL-3 fusion protein), macrophage inflammatory protein (MIP), stem cell factor, thrombopoietin and growth related oncogene, as single agents or in combination (Dale, D., et al., Am. J. of Hematol. (1998) 57:7-15; Rosenfeld, C., et al., Bone Marrow Transplantation (1997) 17:179-183; Pruijt, J., et al., Cur. Op. in Hematol. (1999) 6:152-158; Broxmeyer, H., et al., Exp. Hematol. (1995) 23:335-340; Broxmeyer, et al., Blood Cells, Molecules and Diseases (1998) 24:14-30; Glaspy, J., et al., Cancer Chemother. Pharmacol. (1996) 38 (suppl): S53-S57; Vadhan-Raj, S., et al., Ann Intern. Med. (1997) 126:673-81; King, A., et al., Blood (2001) 97:1534-1542; Glaspy, J., et al., Blood (1997) 90:2939-2951). However, while these agents are effective, there are known disadvantages to their use. For example, since many of these agents/growth factors are proteins, the effort put into the cloning, purification/isolation, in addition to the cost to the patient, sets the stage for searching for small molecule mimics that would be easier to manufacture and less costly for the patient in need of such therapy.

Accordingly, a treatment modality that enhances the stem and/or progenitor cells in blood is helpful in treatments to ameliorate the effects of standard protocols that adversely affect the bone marrow, such as chemotherapy or irradiation therapy that results in leukopenia. The combination of a CXCR4 antagonist in combination with at least one S1PR1 modulating agent in a specific ratio effective to increase HSC mobilization as proposed by the present invention may also enhance the success of bone marrow transplantation, and may also combat infections in the patient undergoing such therapies.

Similarly, administration to a subject receiving a bone marrow transplant a combination of a CXCR4 antagonist with at least one S1PR1 modulating agent in a specific ratio effective to increase HSC engraftment can enhance the success of bone marrow transplant. The combination of a CXCR4 antagonist in combination with at least one S1PR1 modulating agent in a specific ratio effective to increase HSC mobilization can be used to mobilize and harvest hematopoietic stem cells or progenitor cells via apheresis and the harvested cells are used in treatments requiring stem cell transplantations. Furthermore, the combination of a CXCR4 antagonist in combination with at least one S1PR1 modulating agent in a specific ratio effective to increase HSC mobilization can be used both in vivo to promote mobilization of hematopoietic stem cells or progenitor cells from the bone marrow to the peripheral blood, or alternatively, can be used ex vivo, whereby a patient's own stem cells are removed and expanded in culture for autologous transplants. Also contemplated by the present invention are in vitro screens, whereby candidate or test compounds can be combined with a CXCR4 antagonist, e.g., AMD3100, and measured for their effects on mobilization before being administered in vivo.

HSC Mobilization

As disclosed herein, the present invention relates to a unique combination of HSC modulator agents, specifically CXCR4 antagonists with different molar ratios of S1PR1 modulator agents (e.g., S1PR1 agonists and antagonists) which can be administered to a subject for increased HSC mobilization (e.g., for a bone marrow donor subject) or administered to a subject for HSC engraftment (e.g., for a bone marrow or HSC transplant recipient).

In particular, the inventors have demonstrate that mobilization of HSCs was enhanced when a different ratio of the same agents; antagonist (W146) or S1PR1 agonist (FTY720 or SEW2871) in combination with a CXCR4 antagonist (AMD3100) was used.

Without being limited to theory, exemplary HSC modulator agent combination concentrations or ratios to increase HSC mobilization are shown in Table 1. In particular, in some embodiments, for mobilization of HSCs, exemplary CXCR4 antagonists and S1PR1 modulator agent combination concentrations or ratios to increase HSC mobilization are as follows: a ratio of AMD3100 to W146 between 1.25-2.0:1, or in some embodiments a ratio of AMD3100:W146 is a 2:1 ratio; a ratio of AMD3100 to FTY720 is 5:1, a ratio of AMD3100 to SEW2871 is between 1.25-5:1, or in some embodiments, a ratio of AMD3100:FTY720 of 5:3.

In some embodiments, exemplary concentrations of CXCR4 antagonists and S1PR1 modulator agent useful in methods to increase HSC mobilization in a subject include: AMD3100:W146 at 2-25 µM:2-20 µM, or 10 µM AMD3100+5 µM W146; or AMD3100:FTY720 ratio of 10-50 µM-2-25 µM, or 25 µM AMD3100+5 µM FTY720; or AMD3100:SEW2871 ratio of 10-50 µM:6-30 µM or 25 µM AMD3100+15 µM SEW2871.

As demonstrated herein, S1PR1 modulator agents used in combination with a CXCR4 antagonists, e.g., AMD3100, at the molar ratios as shown in Table 1 can promote HSC mobilization, thus increase HSC numbers in peripheral blood. An increase in HSC numbers in the peripheral blood can be an increase of about 10%, about 20%, about 30%, about 40%, about 50%, about 60%, about 70%, about 80%, about 90%, about 100%, about 150%, about 200% or more, than the HSC numbers exhibited by the subject prior to treatment with a combination of a CXCR4 antagonist in combination with at least one S1PR1 modulating agent in a specific ratio effective to increase HSC mobilization. S1PR1 modulator agents can also influence HSC expansion in culture (in vitro), during short term incubation (ex vivo) or in vivo.

TABLE 1

Example of ratios of S1PR1 modulating agents in combination with CXCR4 antagonists which are effective at increasing HSC mobilization:

| | Experimental data | Ratio range AMD3100:S1PR1 modulator agent | Exemplary range AMD3100:S1PR1 modulator agent | AMD3100 (dose range) | Dose range of other compound |
|---|---|---|---|---|---|
| W146 | 10 μM AMD3100 + 5 μM W146 | (1.25-2.0):1 | 2:1 | 10 μM (5-25 μM) 2 mg/kg (1-5 mg/kg) | 5 μM (2 μM-20 μM) 1 mg/kg (0.4-4 mg/kg) |
| FTY720 | 25 μM AMD3100 + 5 μM FTY720 | 5:1 | 5:1 | 25 μM (10-50 μM) 5 mg/kg (2-10 mg/kg) | 5 μM (2 μM-25 μM) 1 mg/kg (0.4-5 mg/kg) |
| SEW2871 | 25 μM AMD3100 + 15 μM SEW2871 | (1.25-5.0):1 | 5:3 | 25 μM (10-50 μM) 5 mg/kg (2-10 mg/kg) | 15 μM (6 μM-30 μM) 3 mg/kg (1.2-6 mg/kg) |

The combination of a CXCR4 antagonist with at least one S1PR1 modulating agent in a specific ratio effective to increase HSC mobilization (see Table 1) can cause mobilization of HSC can cause a mobilization of about 10%, about 20%, about 30%, about 40%, about 50%, about 60%, about 70%, about 80%, about 90%, about 100%, HSCs from the bone marrow. In some embodiments, the amount of HSCs in the circulation increase by about 10%, about 20%, about 30%, about 40%, about 50%, about 60%, about 70%, about 80%, about 90%, about 100%, about 150%, about 200% or more by the combination of a CXCR4 antagonist with at least one S1PR1 modulating agent in a specific ratio effective to increase HSC mobilization as compared to the number of HSCs in the circulation, e.g., peripheral blood (PB) in the subject prior to treatment. HSC numbers in the peripheral blood may be evaluated by the alleviation of the symptoms of the disease, for example, increased platelet count, increased hematocrit, wherein platelet count or hematocrit is increased about 10%, about 20%, about 30%, about 40%, about 50%, about 60%, about 70%, about 80%, about 90%, about 100%, about 150%, about 200% or more. The effect on HSC numbers may be evaluated by the alleviation of the symptoms of the disease, for example, increased platelet count, increased hematocrit, wherein platelet count or hematocrit is increased about 10%, about 20%, about 30%, about 40%, about 50%, about 60%, about 70%, about 80%, about 90%, about 100%, about 150%, about 200% or more.

Direct ex vivo administration of a CXCR4 antagonist with at least one S1PR1 modulating agent in a specific ratio effective to increase HSC mobilization (see Table 1) can enable significant in vivo expansion of hematopoietic stem cells, such that even smaller amounts of hematopoietic stem cells can then be enough in transplantation. Consequently, for example, cord blood stem cell transplantation may now be applied to not only children but also adults. Such stem cells may be collected from sources including, for example, peripheral blood, cord blood, bone marrow, amniotic fluid, or placental blood. Alternatively, the HSC-containing source sample may be harvested and then stored immediately in the presence of a combination of CXCR4 antagonist with at least one S1PR1 modulating agent in a specific ratio effective to increase HSC mobilization, or alternatively, initially incubated (prior to differentiation) then thawed in the presence of a CXCR4 antagonist with at least one S1PR1 modulating agent in a specific ratio effective to increase HSC mobilization before introduction into a subject.

Additionally, a CXCR4 antagonist with at least one S1PR1 modulating agent in a specific ratio effective to increase HSC mobilization (see Table 1) can be used in vivo to increase the number of stem cells in bone marrow or other sources (such as cord blood). By increasing the number of stem cells, the total harvest of stem cells from the subject can be significantly improved. Further, by increasing the number of stem cells harvested from the subject, the number of stem cells available for transplantation back into the subject or to another subject can also be significantly improved, thereby potentially reducing the time to engraftment, and consequently leading to a decrease in the time during which the subject has insufficient neutrophils and platelets, thus preventing infections, bleeding, or other complications.

In addition, the present invention can reduce the proportion of subjects who are otherwise unable to mobilize enough cells for stem cell harvest to proceed with treatment for their primary illness, e.g., chemotherapy and other bone marrow ablative treatments. Thus, the proportion of the number of subjects with delayed primary engraftment can also be reduced. Furthermore, the present invention can promote recovery subsequent to bone marrow ablative treatments by increasing HSC numbers.

The combination of a CXCR4 antagonist with at least one S1PR1 modulating agent in a specific ratio effective to increase HSC mobilization (see Table 1) as disclosed herein, can be used in vivo to increase HSC production or mobilization from the bone marrow into the circulation and peripheral blood, or alternatively, can be used ex vivo to increase HSC number. This is accomplished by administering the combination of a CXCR4 antagonist with at least one S1PR1 modulating agent in a specific ratio effective to increase HSC mobilization (see Table 1) to a subject or to the stem cells.

In some embodiments, a combination of a CXCR4 antagonist with at least one S1PR1 modulating agent in a specific ratio effective to increase HSC mobilization (see Table 1) can also be used to provide autologous HSCs to a subject. Typically, this involves the steps of administering a combination of a CXCR4 antagonist with at least one S1PR1 modulating agent in a specific ratio effective to increase HSC mobilization (see Table 1) to a subject in need thereof to enhance expansion of the stem cell population within bone marrow and/or to mobilize the stem cells in peripheral circulation; harvesting one or more of the bone marrow stem cells or one or more of the stem cells in the peripheral circulation; and transplanting the one or more harvested stem cells back into the subject.

It has been shown that hematopoietic stem cells are present in peripheral blood of healthy persons. Unfortunately, they are present in numbers that are insufficient to permit collection of an adequate graft by standard leukapheresis (Kessionger, A. et al., Bone Marrow Transplant 6, 643-646 (1989)). Several methods have been shown to increase the circulation of progenitor and stem cells by "mobilizing" them from the marrow into the peripheral blood. For example, in autologous transplantation, hematopoietic stem/progenitor cells may be mobilized into the peripheral blood (Lane T. A. Transfusion 36, 585-589 (1996)) during the rebound phase of the leukocytes after transient leukopenia induced by myelosuppressive chemotherapy, (Giralt S. et al., Blood, 89, 4531-4536 (1997) by hematopoietic growth factors, or (Lasky L. C. et al., Transfusion 21, 247-260 (1981)) by a combination of both.

One particular aspect of the present invention provides for the combined use of a CXCR4 antagonist with at least one S1PR1 modulator agents in specific ratio to enhance or increase HSC mobilization.

In one embodiment of the invention, agents that decrease the expression of CXCL12 or that block or antagonize CXCR4 may be used in combination with S1PR1 modulator agents in a ratio effective to increase HSC mobilization. These agents that decrease the expression of CXCL12 or that block or antagonize CXCR4 may be selected from the group consisting of small organic molecules, polypeptides, nucleic acids and carbohydrates. In more particular embodiments, the polypeptides that decrease the expression of CXCL12 may be selected from the group consisting of a cytokine, a colony stimulating factor, a protease or a chemokine other than CXCL12. The cytokine may be selected from the group consisting of interleukin-1 (IL-1), interleukin-3 (IL-3), interleukin-6 (IL-6), interleukin-11 (IL-11), interleukin-7 (IL-7) and interleukin-12 (IL12). The protease may be selected from the group consisting of a metalloproteinase (like MMP2 or MMP9) a serine protease, (like cathepsin G, or elastase) a cysteine protease (like cathepsin K) and a dipeptidyl peptidase-1 (DDP-1 OR CD26). The chemokine other than CXCL12 may be selected from the group consisting of IL-8, MIP-1α. and Groβ. The colony stimulating factor may be selected from the group consisting of granulocyte colony stimulating factor (G-CSF), granulocyte-macrophage colony stimulating factor (GM-CSF), macrophage colony stimulating factor (M-CSF), stem cell factor, FLT-3 ligand or a combination thereof. The nucleic acid may be a DNA or an RNA molecule. The nucleic acid may be a small interfering RNA (siRNA) molecule or an antisense molecule specific for CXCL12 or CXCR4.

The CXCR4 antagonist and S1PR1 modulator agents as disclosed herein at ratios effective at increasing HSC mobilization can be administered as sole active ingredients and/or in a mixture with one or more additional active ingredients or agents that are therapeutically or nutritionally useful, such as antibiotics, vitamins, herbal extracts, anti-inflammatories, glucose, antipyretics, analgesics, growth factors (e.g., granulocyte-macrophage colony stimulating factor (GM-CSF), Interleukins (IL-1, IL-2, IL-3, IL-4, IL-5, IL-6, IL-7, IL-8, IL-9, IL-10 IL-11, IL-12, IL-13, IL-14, or IL-15), TPO, or SCF), or other growth factors such as CSF-1, SF, EPO, leukemia inhibitory factor (LIF), or fibroblast growth factor (FGF), as well as C-KIT ligand, M-CSF and TNF-.alpha., PIXY-321 (GM-CSF/IL-3 fusion protein), macrophage inflammatory protein, stem cell factor, thrombopoietin, growth related oncogene, G-CSF, VEGF, or chemotherapy and the like.

The term, "in conjunction with", as used herein, refers to concurrent administration of the active compound with and additional agent (e.g., a growth factor or chemical agent), as well as administration of the active compound within several days (e.g., within approximately 1 to 7 days) of administration of the growth factor. Administration of the additional agent can be before, concurrent, or after administration of the active compound.

In some embodiments, the active compound can be administered alone, or in conjunction with other compounds or agents that mobilize stem cells, such as growth factors (e.g., G-CSF), other mobilizing agents, as disclosed in US Patent Applications 2007/0190023 or 2011/0020274, which are incorporated herein in their entirety by reference, or anti-cancer agent or chemotherapeutic agents, such as cyclophosphamide or 5-fluorouracil; and/or certain antibodies, such as anti-VLA4. Combinations of these other compounds can also be used.

Methods of Identifying Cells in Peripheral Blood

Any methods including quantitative and qualitative methods can be used to identify that the hematopoietic stem cells have been mobilized into the peripheral blood. The methods typically involve isolating a quantity of the patient's blood and analyzing the quantity of the cells within the blood. Any method can be used to analyze the number of cells, including but not limited to: ELISA to identify the specific cells, FACS analysis, coulter counters and other blood counting devices, morphological identification, and PCR. The cells can be identified by any method known to one of skill in the art, including but not limited to, the identification of one or more proteins which are specifically expressed by the stem cells, by morphology, by mRNA expression, and by PCR. The identification of the cells can be done at any time after administration of a composition comprising a CXCR4 antagonist and at least one S1PR1 modulator agent in a ratio effective to increase HSC mobilization, including but not limited to: 5 minutes, 10 minutes, 20 minutes, 30 minutes, 45 minutes, 1 hour, 1.5 hours, 2 hours, 3 hours, 4 hours, 5 hours, 6 hours, 7 hours, 8 hours, 9 hours, 10 hours, 12 hours, 1 day, 2 days, 3 days, 4 days, 5 days, 6 days, 7 days, 2 weeks, 1 month, 2 months, 3 months, 4 months, 5 months, 6 months, 7 months, 8 months, 9 months, 10 months, 1 year, 2 years. Further, the mobilization can be identified soon after treatment to identify whether the treatment is working. If the treatment does not appear to be working, an alternative CXCR4 antagonist and/or S1PR1 modulator agent, or a different ratio can be administered.

The efficacy of the mobilization can be tested throughout treatment with the combination of a CXCR4 antagonist and at least one S1PR1 modulator agent in a ratio effective to increase HSC mobilization), or alternatively, an initial test to determine efficacy can be performed. In some embodiments, a test can be performed 1 day after treatment and again 1 week after treatment.

In addition, the stem cells obtained from harvesting according to method of the present invention described above can be cryopreserved using techniques known in the art for stem cell cryopreservation. Accordingly, using cryopreservation, the stem cells can be maintained such that once it is determined that a subject is in need of stem cell transplantation, the stem cells can be thawed and transplanted back into the subject. As noted previously, the use of the combination of a CXCR4 antagonist with at least one S1PR1 modulating agent in a specific ratio effective to increase HSC mobilization during cryopreservation techniques may enhance the HSC population.

More specifically, another embodiment of the present invention provides for the enhancement of HSCs collected from cord blood or an equivalent neonatal or fetal stem cell source, which may be cryopreserved, for the therapeutic uses of such stem cells upon thawing. Such blood may be collected by several methods known in the art. For example, because umbilical cord blood is a rich source of HSCs (see Nakahata & Ogawa, 70 J. Clin. Invest. 1324-28 (1982); Prindull et al., 67 Acta. Paediatr. Scand. 413-16 (1978); Tchernia et al., 97(3) J. Lab. Clin. Med. 322-31 (1981)), an excellent source for neonatal blood is the umbilical cord and placenta. The neonatal blood may be obtained by direct drainage from the cord and/or by needle aspiration from the delivered placenta at the root and at distended veins. See, e.g., U.S. Pat. Nos. 7,160,714; 5,114,672; 5,004,681; U.S. patent application Ser. No. 10/076,180, Pub. No. 20030032179.

Indeed, umbilical cord blood stem cells have been used to reconstitute hematopoiesis in children with malignant and nonmalignant diseases after treatment with myeloablative doses of chemo-radiotherapy. Sirchia & Rebulla, 84 Haematologica 738-47 (1999). See also Laughlin 27 Bone Marrow Transplant. 1-6 (2001); U.S. Pat. No. 6,852,534. Additionally, it has been reported that stem and progenitor cells in cord blood appear to have a greater proliferative capacity in culture than those in adult bone marrow. Salahuddin et al., 58 Blood 931-38 (1981); Cappellini et al., 57 Brit. J. Haematol. 61-70 (1984).

Alternatively, fetal blood can be taken from the fetal circulation at the placental root with the use of a needle guided by ultrasound (Daffos et al., 153 Am. J. Obstet. Gynecol. 655-60 (1985); Daffos et al., 146 Am. J. Obstet. Gynecol. 985-87 (1983), by placentocentesis (Valenti, 115 Am. J. Obstet. Gynecol. 851-53 (1973); Cao et al., 19 J. Med. Genet. 81-87 (1982)), by fetoscopy (Rodeck, in Prenatal Diagnosis, (Rodeck & Nicolaides, eds., Royal College of Obstetricians & Gynaecologists, London, 1984)). Indeed, the chorionic villus and amniotic fluid, in addition to cord blood and placenta, are sources of pluripotent fetal stem cells (see WO 2003/042405) that may be treated by the HCS modulators of the present invention.

Various kits and collection devices are known for the collection, processing, and storage of cord blood. See, e.g., U.S. Pat. Nos. 7,147,626; 7,131,958. Collections should be made under sterile conditions, and the blood may be treated with an anticoagulant. Such an anticoagulants include citrate-phosphate-dextrose, acid citrate-dextrose, Alsever's solution (Alsever & Ainslie, 41 N.Y. St. J. Med. 126-35 (1941), DeGowin's Solution (DeGowin et al., 114 J.A.M.A. 850-55 (1940)), Edglugate-Mg (Smith et al., 38 J. Thorac. Cardiovasc. Surg. 573-85 (1959)), Rous-Turner Solution (Rous & Turner 23 J. Exp. Med. 219-37 (1916)), other glucose mixtures, heparin, or ethyl biscoumacetate. See Hurn Storage of Blood 26-160 (Acad. Press, NY, 1968).

Various procedures are known in the art and can be used to enrich collected cord blood for HCSs. These include but are not limited to equilibrium density centrifugation, velocity sedimentation at unit gravity, immune rosetting and immune adherence, counterflow centrifugal elutriation, T lymphocyte depletion, and fluorescence-activated cell sorting, alone or in combination. See, e.g., U.S. Pat. No. 5,004,681.

Typically, collected blood is prepared for cryogenic storage by addition of cryoprotective agents such as DMSO (Lovelock & Bishop, 183 Nature 1394-95 (1959); Ashwood-Smith 190 Nature 1204-05 (1961)), glycerol, polyvinylpyrrolidine (Rinfret 85 Ann N.Y. Acad. Sci. 576-94 (1960)), polyethylene glycol (Sloviter & Ravdin 196 Nature 899-900 (1962)), albumin, dextran, sucrose, ethylene glycol, i-erythritol, D-ribitol, D-mannitol (Rowe, 3(1) Cryobiology 12-18 (1966)), D-sorbitol, i-inositol, D-lactose, choline chloride (Bender et al., 15 J. Appl. Physiol. 520-24 (1960)), amino acids (Phan & Bender, 20 Exp. Cell Res. 651-54 (1960)), methanol, acetamide, glycerol monoacetate (Lovelock, 56 Biochem. J. 265-70 (1954)), and inorganic salts (Phan & Bender, 104 Proc. Soc. Exp. Biol. Med. (1960)). Addition of plasma (e.g., to a concentration of 20-25%) may augment the protective effect of DMSO.

Collected blood should be cooled at a controlled rate for cryogenic storage. Different cryoprotective agents and different cell types have different optimal cooling rates. See e.g., Rapatz, 5(1) Cryobiology 18-25 (1968), Rowe & Rinfret, 20 Blood 636-37 (1962); Rowe, 3(1) Cryobiology 12-18 (1966); Lewis et al., 7(1) Transfusion 17-32 (1967); Mazur 168 Science 939-49 (1970). Considerations and procedures for the manipulation, cryopreservation, and long-term storage of HSC sources are known in the art. See e.g., U.S. Pat. Nos. 4,199,022; 3,753,357; 4,559,298; 5,004,681. There are also various devices with associated protocols for the storage of blood. U.S. Pat. Nos. 6,226,997; 7,179,643

Considerations in the thawing and reconstitution of HCS sources are also known in the art. U.S. Pat. Nos. 7,179,643; 5,004,681. The HCS source blood may also be treated to prevent clumping (see Spitzer, 45 Cancer 3075-85 (1980); Stiff et al., 20 Cryobiology 17-24 (1983), and to remove toxic cryoprotective agents (U.S. Pat. No. 5,004,681). Further, there are various approaches to determining an engrafting cell dose of HSC transplant units. See U.S. Pat. No. 6,852,534; Kuchler Biochem. Methods in Cell Culture & Virology 18-19 (Dowden, Hutchinson & Ross, Strodsburg, Pa., 1964); 10 Methods in Medical Research 39-47 (Eisen, et al., eds., Year Book Med. Pub., Inc., Chicago, Ill., 1964).

Thus, not being limited to any particular collection, treatment, or storage protocols, an embodiment of the present invention provides for the addition of a combination of a CXCR4 antagonist with at least one S1PR1 modulating agent in a specific ratio effective to increase HSC mobilization to the neonatal blood. This may be done at collection time, or at the time of preparation for storage, or upon thawing and before infusion.

For example, stem cells isolated from a subject, e.g., with or without prior treatment of the subject with a combination of a CXCR4 antagonist with at least one S1PR1 modulating agent in a specific ratio effective to increase HSC mobilization, may be incubated in the presence of a combination of a CXCR4 antagonist with at least one S1PR1 modulating agent in a specific ratio effective to increase HSC mobilization, e.g., at ratios as listed in Table 1, in order to mobilize and/or expand the number of HSCs. Expanded HSCs may be subsequently reintroduced into the subject from which they were obtained (e.g., autologous transplant) or may be introduced into another subject (allogenic transplant). In some embodiments, the recipient subject is treated with a combination of a CXCR4 antagonist with a S1PR1 modulating agent in a ratio effective to enhance HSC engraftment according to the methods as disclosed herein.

The combination of a CXCR4 antagonist with at least one S1PR1 modulating agent in ratios effective to increase HSC mobilization as set forth in Table 1 and disclosed herein, can thus be used for, inter alia: reducing the time to engraftment following reinfusion of stem cells in a subject; reducing the incidence of delayed primary engraftment; reducing the incidence of secondary failure of platelet production; and reducing the time of platelet and/or neutrophil recovery following reinfusion of stem cells in a subject. These methods typically include the steps of administering a combination of a CXCR4 antagonist with at least one S1PR1 modulating agent in a ratio effective to increase HSC mobilization as set forth in Table 1, to a subject in need thereof to enhance expansion of the stem cell population within bone marrow and/or mobilize the stem cells in peripheral circulation and then harvesting one or more of the bone marrow stem cells or the stem cells in the peripheral circulation and then transplanting the harvested stem cell back into the subject at the appropriate time, as determined by the particular needs of the subject.

The combination of a CXCR4 antagonist with at least one S1PR1 modulating agent in a ratio effective to increase HSC mobilization and thus cause an increase HSC numbers, can provide a convenient single dose therapy to improve the efficiency of stem cell transplantation, to permit more aggressive treatment of solid tumors, myeloma and lymphoma and to increase the number of candidates for stem cell transplantation.

The method of the invention using combination of a CXCR4 antagonist with at least one S1PR1 modulating agent in a ratio effective to increase HSC mobilization as set forth in Table 1 may also be used to increase the number of stem cells from a donor subject (including bone marrow cells or cord blood cells), whose cells are then used for rescue of a recipient subject who has received bone marrow ablating chemotherapy or irradiation therapy.

As used herein, a subject includes anyone who is a candidate for autologous stem cell or bone marrow transplantation during the course of treatment for malignant disease or as a component of gene therapy. Other possible candidates are subjects who donate stem cells or bone marrow to subjects for allogeneic transplantation for malignant disease or gene therapy. Subjects may have undergone irradiation therapy, for example, as a treatment for malignancy of cell type other than hematopoietic. Subjects may be suffering from anemia, e.g., sickle cell anemia, thalessemia, aplastic anemia, or other deficiency of HSC derivatives.

While the present invention relates primarily to promoting egress or mobilization of hematopoietic stem cells from their niche in the bone marrow to the peripheral circulation using a combination of a CXCR4 antagonist and at least one S1PR1 modulator agent in a specific ratio to promote mobilization of HSCs, it is proposed that the same mechanisms may be involved in the egress of cancer stem cells from their niche into the circulation, lymphatic system or to distant organs and tissues, thus exacerbating the metastatic process. However, using a combination of a CXCR4 antagonist and at least one S1PR1 modulator agent in a specific ratio to promote mobilization of HSCs may also mobilize cancer stem cells from their niche in the microenvironment, or in the tumor cell itself, and may paradoxically lead to increased metastasis. Thus, it may be that while this strategy may be useful in the treatment of cancer, (e.g., to mobilize cancer stem cells into the peripheral blood thus allowing them to be more susceptible to chemotherapeutics agents and radiotherapy), it may be useful to combine this therapy with administration of a chemotherapeutic drug or irradiation therapy, as proposed herein. Thus, in another embodiment, it is envisioned that a combination of a CXCR4 antagonist and at least one S1PR1 modulator agent in a specific ratio to promote mobilization of HSC may be used to optimize the egress of cancer stem cells from their niche in the microenvironment, which may bring them from a quiescent state to an actively dividing state, thus making them more sensitive to chemotherapy or irradiation therapy, which may target actively dividing cells. Accordingly, in some embodiments, a combination of a CXCR4 antagonist and at least one S1PR1 modulator agent in a specific ratio to promote mobilization of HSCs is administered in combination with an anti-cancer agent, e.g., a chemotherapeutic agent or radiotherapy, which may be useful for treating patients suffering from a cancerous condition.

Myelosuppressive Therapy

Hematopoietic stem cell mobilization into peripheral blood has been used as a procedure following myelosuppressive chemotherapy regimens to mobilize hematopoietic stem and progenitor cells into the peripheral blood. Suggested treatment regimens for mobilization may include cyclophosphamide alone, in single doses of 4-7 g/m2, or other agents such as Adriamycin (doxorubicin), carboplatin, Taxol (paclitaxel), etoposide, ifosfamide, daunorubicin, cytosine arabinosides 6-thioguanine, either alone or in combination (Richman, C. M. et al., Blood 47, 1031-1039 (1976); Stiff P. J. et al., Transfusion 23, 500-503 (1983); To L. B. et al. Bone Marrow Transplant 9, 277-284 (1992)). Such a regiment may induce a transient but profound myelosuppression in patients, at about 7-14 days after chemotherapy. This maybe followed on day 10-21 by rapid reappearance of leukocytes in the peripheral blood and frequently a "rebound" increase of the circulating leukocytes above baseline levels. As the leukocyte count rises, hematopoietic progenitor cells also begin to appear in the peripheral blood and rapidly increase.

Hematopoietic stem cells (HSC) collected from mobilized peripheral blood progenitor cells (PBPC) are increasingly used for both autologous and allogeneic transplantation after myeloablative or nonmyeloablative therapies (Lane T. A. Transfusion 36, 585-589 (1996)). Purported advantages of PBPC transplantation include rapid and durable trilineage hematologic engraftment, improved tolerance of the harvesting procedure (without general anesthesia), and possibly diminished tumor contamination in the autologous setting (Lasky L. C. et al., Transfusion 21, 247-260 (1981); Moss T. J. et al, Blood 76, 1879-1883)). Techniques for autologous mobilized PBPC grafting may also be successful for allogeneic transplantation. Early reports in animals and syngeneic transplants in humans supported this hypothesis (Kessionger, A. et al., Bone Marrow Transplant 6, 643-646 (1989)).

Many investigators have reported that PBPC mobilization employing a combination of chemotherapy and followed by growth factor (GM-CSF or G-CSF) administration is more effective than either chemotherapy or growth factor alone (Siena S. et al., Blood 74, 1905-1914 (1989); Pettengel R. et al., Blood, 2239-2248 (1993); Haas R. et al., Bone Marrow Transplant 9, 459-465 (1992); Ho A. D. et al., Leukemia 7, 1738-1746 (1993)). The combination reportedly results in a 50- to 75-fold increase in circulating CFU-GM and 10- to 50-fold increase in CD34+ cells (Pettengel R. et al., Blood, 2239-2248 (1993); Haas R. et al., Bone Marrow Transplant 9, 459-465 (1992); Ho A. D. et al., Leukemia 7, 1738-1746 (1993)). Direct comparisons show that chemotherapy and growth factors resulted in a mean 3.5-fold greater peak number of circulating CFU-GM (range, 0 to 6.8 times greater verses chemotherapy or growth factor alone (Siena S. et al., Blood 74, 1905-1914 (1989); Pettengel R. et al., Blood, 2239-2248 (1993); Haas R. et al., Bone Marrow Transplant 9, 459-465 (1992); Moskowitz C. H. et al. Clin. Cancer Res. 4, 311-316 (1998)).

It is reportedly possible to expand hematopoietic progenitor cells in stroma-containing or nonstromal systems. Expansion systems have reportedly shown increases in CFU GM of more than 100-fold. Enrichment of CD34+ cells may be required before expansion in nonstromal culture but may not be necessary in stroma-containing systems. Early results of clinical trails are encouraging and have been taken to demonstrate that the engraftment potential of the expanded hematopoietic cells is not compromised by culture. Expansion of cord blood-derived hematopoietic cells may be especially important because of the limited number of cells that can be collected. Successful expansion of primitive and committed hematopoietic cells from cord blood may allow more extensive use in clinical transplantation, particularly in adult patients. Other possible applications of stem cell expansion include purging of tumor cells; production of immune-competent cells, such as dendritic cells and NK cells, and gene therapy.

Permanent marrow recovery after cytotoxic drug and radiation therapy generally depends on the survival of hematopoietic stem cells having long term reconstituting (LTR) potential. The major dose limiting sequelae consequent to chemotherapy and/or radiation therapy are typically neutropenia and thrombocytopenia. Protocols involving dose intensification (i.e., to increase the log-kill of the respective tumor therapy) or schedule compression may exacerbate the degree and duration of myelosuppression associated with the chemotherapy and/or radiation therapy. For instance, in the adjuvant setting, repeated cycles of doxorubicin-based treatment have been shown to produce cumulative and long-lasting damage in the bone marrow progenitor cell populations (Lorhrman et al., (1978) Br. J. Haematol. 40:369). The effects of short-term hematopoietic cell damage resulting from chemotherapy has been overcome to some extent by the concurrent use of G-CSF (Neupogen™.), used to accelerate the regeneration of neutrophils (Le Chevalier (1994) Eur. J. Cancer 30A:410). This approach has been met with limitations also, as it may be accompanied by progressive thrombocytopenia and cumulative bone marrow damage as reflected by a reduction in the quality of mobilized progenitor cells over successive cycles of treatment. Because of the current interest in chemotherapy dose intensification as a means of improving tumor response rates and perhaps patient survival, the necessity for alternative therapies to either improve or replace current treatments to rescue the myeloablative effects of chemotherapy and/or radiation therapy has escalated, and is currently one of the major rate limiting factors for tumor therapy dose escalations.

Transplanted peripheral blood stem cells (PBSC, or autologous PBSC) may provide a rapid and sustained hematopoietic recovery after the administration of high-dose chemotherapy or radiation therapy in patients with hematological malignancies and solid tumours. PBSC transplantation has become the preferred source of stem cells for autologous transplantation because of the shorter time to engraftment and the lack of a need for surgical procedures such as are necessary for bone marrow harvesting (Demirer et al. (1996) Stem Cells 14:106-116; Pettengel et al., (1992) Blood 82:2239-2248). Although the mechanism of stem cell release into the peripheral blood from the bone marrow is not well understood, agents that augment the mobilization of CD34+ cells may prove to be effective in enhancing autologous PBSC transplantation. G-CSF and GM-CSF are currently the most commonly used hematopoietic growth factors for PBSC mobilization, although the mobilized cellular profiles can differ significantly from patient to patient. Therefore, other agents, such as those proposed and described herein are required for this clinical application.

Accordingly, in some embodiments, the CXCR4 antagonists, e.g., AMD3100 and mimetics thereof in combination with a S1PR1 modulator agent at a ration effective to increase mobilization of HSC in a subject can be used in a methods for treatment following myelosuppressive chemotherapy regimens.

HSC Engraftment.

As disclosed herein, the present invention relates to a unique combination of HSC modulator agents, specifically CXCR4 antagonists with different molar ratios of S1PR1 modulator agents (e.g., S1PR1 agonists and antagonists) which can be administered to a subject for increased HSC engraftment (e.g., for a bone marrow or HSC transplant recipient).

In particular, the inventors have demonstrate that engraftment of HSCs was optimized when different ratios of S1PR1 modulator agents, e.g., a S1PR1 (S1P receptor 1) antagonist (W146) or S1PR1 agonist (FTY720, SEW2871, or AUY954) with a CXCR4 antagonist (AMD3100) were used. Conversely, the inventors discovered that mobilization of HSCs was enhanced when a different ratio of the same agents; antagonist (W146) or S1PR1 agonist (FTY720 or SEW2871) in combination with a CXCR4 antagonist (AMD3100) was used.

Without being limited to theory, exemplary HSC modulator agent combination concentrations or ratios to increase HSC engraftment are shown in Table 2. In particular, in some embodiments, exemplary CXCR4 antagonists and S1PR1 modulator agent combination concentrations or ratios to increase HSC engraftment are as follows: a ratio of AMD3100 to W146 of between about 0.5-0.6:1, and in some embodiments, a ratio of AMD3100:W146 of 1:2; a ratio of AMD3100 to AUY945 is between 0.4-2.5:1, and in some embodiments, the ratio of AMD3100:AUY945 is 1.1.25, a ratio of AMD3100:FTY720 is between 0.4-3.0:1, in some embodiments, a ratio of AMD3100:FTY720 is 3:1, a ratio of AMD3100 to SEW2871 is between 0.25-1.0:1, and in some embodiments, a ratio of AMD3100:SEW2871 is 1:1.

In some embodiments, the following CXCR4 antagonists and S1PR1 modulator agent concentrations are useful in the method as disclosed herein to increase HSC engraftment in a subject: a ratio of AMD3100:W146 of about 2-25 µM:5-25 µM, or 5 µM AMD3100+10 µM W146; a ratio of AMD3100: AUY954 of 5-20 µM:5-25 µM, or in some embodiments, 10 µM AMD3100+12.5 µM AUY954; a ratio of AMD3100: FTY720 of about 5-25 µM:2-25 µM, or in some embodiments 15 µM AMD3100+5 µM FTY720; and a ratio of AMD3100:SEW2871 of about 5-25 µM:5-25 µM, or in some embodiments 10 µM AMD3100+10 µM SEW2871.

TABLE 2

Example of ratios of S1PR1 modulating agents in combination with CXCR4 antagonists which are effective at increasing HSC engraftment.

| | Experimental data | Range ratio of AMD3100:S1PR1 modulator agent | Exemplary Ratio AMD3100:S1PR1 modulator agent | AMD3100 (dose range) | Dose range of other compound |
|---|---|---|---|---|---|
| W146 | 5 µM AMD3100 + 10 µM W146; | (0.5-0.6):1 | 1:2 | 5 µM (2 µM-25 µM) 1 mg/kg (0.4-5 mg/kg) | 10 µM (5-25 µM) 2 mg/kg (1-5 mg/kg) |

TABLE 2-continued

Example of ratios of S1PR1 modulating agents in combination with CXCR4 antagonists which are effective at increasing HSC engraftment.

| Experimental data | | Range ratio of AMD3100:S1PR1 modulator agent | Exemplary Ratio AMD3100:S1PR1 modulator agent | AMD3100 (dose range) | Dose range of other compound |
|---|---|---|---|---|---|
| AUY954 | 10 µM AMD3100 + 12.5 µM AUY954 | (0.4-2.5):1 | 1:1.25 | 10 µM (5 µM-20 µM) 2 mg/kg (1-4 mg/kg) | 12.5 µM (5-25 µM) 2.5 mg/kg (1.25-5 mg/kg) |
| FTY720 | 15 µM AMD3100 + 5 µM FTY720 | (0.4-3.0):1 | 3:1 | 15 µM (5 µM-25 µM) 3 mg/kg (1-5 mg/kg) | 5 µM (2-25 µM) 1 mg/kg (0.4-5 mg/kg) |
| SEW2871 | 10 µM AMD3100 + 10 µM SEW2871 | (0.25-1.0):1 | 1:1 | 10 µM (5 µM-25 µM) 2 mg/kg (1-5 mg/kg) | 10 µM (5 µM-25 µM) 2 mg/kg (1-5 mg/kg) |

In some embodiments, the HSC-containing source sample may be harvested and then stored immediately in the presence of a combination of CXCR4 antagonist with at least one S1PR1 modulating agent in a specific ratio effective to increase HSC engraftment, or alternatively, the HSC-containing source can be stored, then incubated (prior to, or after differentiation) in the presence of a CXCR4 antagonist with at least one S1PR1 modulating agent in a specific ratio effective to increase HSC engraftment before introduction into a subject.

Thus, not being limited to any particular collection, treatment, or storage protocols, an embodiment of the present invention provides for the addition of a combination of a CXCR4 antagonist with at least one S1PR1 modulating agent in a ratio effective to increase HSC engraftment to any population of cells comprising HSCs, including adult peripheral blood, umbilical cord blood, neonatal blood. This may be done at collection time, or at the time of preparation for storage, or upon thawing and before infusion.

The combination of a CXCR4 antagonist with at least one S1PR1 modulating agent in ratios effective to increase HSC engraftment as set forth in Table 2 can thus be used for, inter alia: reducing the time to engraftment following infusion of stem cells into a subject; reducing the incidence of delayed primary engraftment; reducing the incidence of secondary failure of platelet production; and reducing the time of platelet and/or neutrophil recovery following reinfusion of stem cells in a subject. These methods typically include the steps of administering a combination of a CXCR4 antagonist with at least one S1PR1 modulating agent in a ratio effective to increase HSC engraftment as set forth in Table 2, to a subject in need thereof (e.g., a subject about to, or has undergone HSC transplantation) to enhance engraftment of the HSC population within bone marrow.

In alternative embodiments, the HSCs are contacted with a combination of a CXCR4 antagonist with at least one S1PR1 modulating agent in a ratio effective to increase HSC engraftment as set forth in Table 2, immediately after harvesting the HSC population from the donor subject, or during an incubation period (e.g., ex vivo), prior to transplanting the HSCs into the recipient subject. In some embodiments, the HSC population to be transplanted into the recipient subject is a mobilized HSC population performed by the methods as disclosed herein.

Methods for Treating Cancer

It is envisioned that the methods of the invention may be applicable not only for use in enhancing mobilization of hematopoietic stem cells, or for enhancing HSC engraftment, but may also be applicable for treating cancers, for example, carcinomas, including but not limited to, breast or prostate cancer. Prostate cancer is the most common malignancy of males, affecting one male in nine over 65 years of age. Despite enormous advances in our understanding of the biology and the therapy of the disease, the high incidence of distant metastases remains the leading cause of death. Therefore new avenues to prevent the occurrence of metastasis may have a profound clinical impact in the management of prostate cancer.

Accordingly, in some embodiments, a combination of a CXCR4 antagonist and at least one S1PR1 modulator agent in a specific ratio effective to increase HSC engraftment can be used in a method to treat cancer, in particular, a method to treat malignant cancer by preventing the egress of HSCs and cancer stem cells from the bone marrow, thus reducing occurrence of metastasis.

Accordingly, in some embodiments, a combination of a CXCR4 antagonist and at least one S1PR1 modulator agent in a specific ratio effective to increase HSC engraftment can be used in conjunction with an anti-cancer agent.

A number of suitable anti-cancer agents are contemplated for combination or co-administration or in conjunction with a CXCR4 antagonist and at least one S1PR1 modulator agent in a specific ratio effective to increase HSC engraftment to treat, prevent, or ameliorate any of the aforementioned diseases, maladies, conditions, or disorders. Indeed, some embodiments contemplate, but are not limited to, administration of a CXCR4 antagonist and at least one S1PR1 modulator agent in a specific ratio effective to increase HSC engraftment in combination or co-administered with numerous anticancer agents such as: agents that induce apoptosis; polynucleotides (e.g., anti-sense, ribozymes, siRNA); polypeptides (e.g., enzymes and antibodies); biological mimetics (e.g., gossypol or BH3 mimetics); agents that bind (e.g., oligomerize or complex) Cdc42; alkaloids; alkylating agents; antitumor antibiotics; antimetabolites; hormones; platinum compounds; monoclonal or polyclonal antibodies (e.g., antibodies conjugated with anti-cancer drugs, toxins, defensins), toxins; radionuclides; biological response modifiers (e.g., interferons (e.g., IFN-alpha) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteasome inhibitors: NF-KB modulators; anti-CDK compounds; HDAC inhibitors; and the like. Numerous other examples of chemotherapeutic compounds and anticancer therapies suitable for mixture or co-administration with the disclosed CXCR4 antagonists and at least one S1PR1 modulator agent in a specific ratio effective to increase HSC engraftment are known to those skilled in the art.

In more embodiments, the combination of a CXCR4 antagonist and at least one S1PR1 modulator agent in a specific ratio effective to increase HSC engraftment as described herein and used in the methods disclosed are mixed or combined or co-administered with anticancer agents that induce or stimulate apoptosis. Agents that induce apoptosis which are suitable in such compositions, mixtures, therapies and methods include, but are not limited to, radiation (e.g., X-rays, gamma rays, UV); tumor necrosis factor (TNF)-related factors (e.g., TNF family receptor proteins, TNF family ligands, TRAIL, antibodies to TRAILR1 or TRAILR2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC™)); antisense molecules; antibodies (e.g., HERCEPTINT™, RITUXAN™, ZEVALIN™, and AVASTINT™); antiestrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON™, DELTASONE™, dexamethasone, dexamethasone intensol, DEXONE™, HEXADROL™, hydroxychloroquine, METI-CORTENT™, oradexon, ORASONE™, oxyphenbutazone, PEDIAPRED™, phenyl butazone, PLAQUENIL™, prednisolone, prednisone, PRELONE™, and TANDEARIL™); and cancer chemotherapeutic drugs (e.g., irinotecan (CAMPTOSAR™), CPT-11, fludarabine (FLUDARAT™), dacarbazine (DTICT™), dexamethasone, mitoxantrone, MYLOTARG™, VP-16™, cisplatin, carboplatin, oxaliplatin, 5-FU™, doxorubicin, gemcitabine, bortezomib, gefitinib, bevacizumab, TAXOTERE™ or TAXOL™); cellular signaling molecules; ceramides and cytokines; staurosporine, and the like.

In still other embodiments, compositions and methods described provide a combination of a CXCR4 antagonist and at least one S1PR1 modulator agent in a specific ratio effective to increase HSC engraftment, and at least one anti-hyperproliferative or antineoplastic agent selected from alkylating agents, antimetabolites, and natural products (e.g., herbs and other plant and/or animal derived compounds).

Alkylating agents suitable for use in the present compositions, mixtures, therapies, and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC™; dimethyltriazenoimid-azolecarboxamide).

In some embodiments, antimetabolites suitable for use in the present compositions, mixtures, therapies, and methods include, but are not limited to: 1) folic acid analogs (e.g., methotrexate (amethopterin)); 2) pyrimidine analogs (e.g., fluorouracil (5-fluorouracil; 5-FU™) floxuridine (fluorodeoxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use with the compositions, mixtures, therapies, and methods described herein include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; M1H)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods disclosed herein. For example, the U.S. Food and Drug Administration maintains a formulary of oncolytic agents approved for use in the United States. International counterpart agencies to the U.S.F.D.A. maintain similar formularies.

In some embodiments, conventional anticancer agents for use in administration with the present compounds include, but are not limited to, adriamycin, 5-fluorouracil, etoposide, camptothecin, actinomycin D, mitomycin C, cisplatin, docetaxel, gemcitabine, carboplatin, oxaliplatin, bortezomib, gefitinib, bevacizumab, demethylating agents, inhibitors of her-2, inhibitors of IGF-1R, VEGF, inhibitors of VEGFR, mTOR inhibitors, mitotic inhibitors, Smad inhibitors and taxanes. These agents can be prepared and used singularly, in combined therapeutic compositions, in kits, or in combination with immunotherapeutic agents, and the like.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

CXCR4 Antagonists

In some embodiments, a CXCR4 antagonist is AMD3100, or derivatives or analogues or combinations thereof. The structure of AMD-3100 and its derivatives and analogs thereof are encompassed for use in the methods, compositions and kits of the present invention and can be found in U.S. Pat. No. 6,987,102, which is incorporated by reference in its entirety.

AMD3100 is also know as 1,1'-[1,4-Phenylenebis(methylene)]bis[1,4,8,11-tetraazacyclotetradecane] and has the following structure (Compound I):

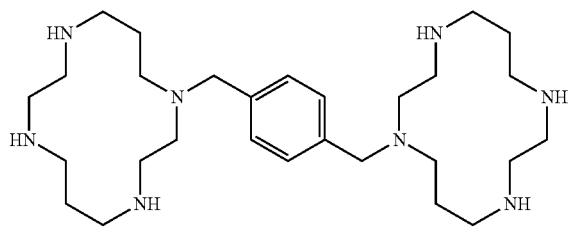 [SMILES: c1cc(CN2CCCNCCNCCCNCC2)ccc1CN1CCCNCCNCCCNCC1]

In some embodiments, a CXCR4 antagonist is T-140 (4F-benzoyl-TN14403), which has been reported to exhibit rapid HSC mobilization in mammals and a synergistic effect when administered together with G-CSF (Abraham, 2007, Stem Cells, 25; 2158-2166, which is incorporated herein in its entirety by reference).

Other CXCR4 antagonists encompassed for use in the methods and compositions as disclosed herein include without limitation RNAi agents to CXCR4, as well as anti-VLA-4 (Papayannopoulou et al, 1993) and anti-cKit (Czechowicz et al, 2007).

Derivatives, as used herein, include a chemically modified compound wherein the modification is considered routine by the ordinary skilled chemist, such as additional chemical moieties (e.g., an ester or an amide of an acid, protecting groups, such as a benzyl group for an alcohol or thiol, and tert-butoxycarbonyl group for an amine). Derivatives also include radioactively labeled CXCR4 antagonist, conjugates of CXCR4 antagonist (e.g., biotin or avidin, with enzymes such as horseradish peroxidase and the like, with bioluminescent agents, chemoluminescent agents or fluorescent agents). Additionally, moieties may be added to a CXCR4 antagonist or a portion thereof to increase half-life in vivo. Derivatives, as used herein, also encompasses analogs, such as a compound that comprises a chemically modified form of a specific compound or class thereof, and that maintains the pharmaceutical and/or pharmacological activities characteristic of said compound or class, are also encompassed in the present invention. Derivatives, as used herein also encompasses prodrugs of a CXCR4 antagonist, which are known to enhance numerous desirable qualities of pharmaceuticals (e.g., solubility, bioavailability, manufacturing, etc.).

In some embodiments, as an alternative to using a CXCR4 antagonist in the methods and compositions as disclosed herein, an agent which decreases the expression or function of a chemokine, more particularly, CXCL12, also known as SDF-1 can be used. The human amino acid sequence of SDF-1 has Gen Bank accession number CAG29279. The alpha isoform has GenBank accession number NP_954637. The beta isoform has GenBank accession number NP_000600. The gamma isoform has GenBank accession number NP_001029058.

Alternatively, a CXCR4 antagonist for use in the methods, kits and compositions as disclosed herein can be a RNAi agent which interferes with the expression of CXCR4. RNAi agents are well known by persons of ordinary skill, and can be selected based on their ability to gene silence the human amino acid sequence of CXCR4, which has GenBank accession number CAA12166.

CXC chemokine receptor 4 (CXCR4), is a 7 transmembrane protein, coupled to G1 and was previously called LESTR (Loetscher, M., Geiser, T., O'Reilly, T., Zwahlen, R., Baggionlini, M., and Moser, B., (1994) J. Biol. Chem., 269, 232-237), HUMSTR (Federsppiel, B., Duncan, A. M. V., Delaney, A., Schappert, K., Clark-Lewis, I., and Jirik, F. R. (1993) Genomics 16, 707-712) and Fusin (Feng, Y., Broeder, C. C., Kennedy, P. E., and Berger, E. A. (1996) HIV-1 entry cofactor: Functional cDNA cloning of a seven-transmembrane G protein-coupled receptor, Science 272, 872-877). CXCR4 is widely expressed on cells of hemopoietic origin, and is a major co-receptor with CD4 for human immunodeficiency virus 1 (HIV-1) (Feng, Y., Broeder, C. C., Kennedy, P. E., and Berger, E. A. (1996) HIV-1 entry cofactor: Functional cDNA cloning of a seven-transmembrane G protein-coupled receptor, Science 272, 872-877).

Chemokines are thought to mediate their effect by binding to seven transmembrane G protein-coupled receptors, and to attract leukocyte subsets to sites of inflammation (Baglionini et al. (1998) Nature 392: 565-568). Many of the chemokines have been shown to be constitutively expressed in lymphoid tissues, indicating that they may have a homeostatic function in regulating lymphocyte trafficking between and within lymphoid organs (Kim and Broxmeyer (1999) J. Leuk. Biol. 56: 6-15).

Stromal cell derived factor one (SDF-1), also known as CXCL12, is a member of the CXC family of chemokines that has been found to be constitutively secreted from the bone marrow stroma (Tashiro, (1993) Science 261, 600-602). The human and mouse SDF-1 predicted protein sequences are approximately 92% identical. Stromal cell derived factor-1.alpha. (SDF-1α) and stromal cell derived factor-1β. (SDF-1β) are closely related (together referred to herein as SDF-1). The native amino acid sequences of SDF-1α and SDF-1β.are known, as are the genomic sequences encoding these proteins (see U.S. Pat. No. 5,563,048 issued 8 Oct. 1996, and U.S. Pat. No. 5,756,084 issued 26 May 1998). Identification of genomic clones has shown that the alpha and beta isoforms are a consequence of alternative splicing of a single gene. The alpha form is derived from exons 1-3 while the beta form contains an additional sequence from exon 4. The entire human gene is approximately 10 Kb. SDF-1 was initially characterized as a pre-B cell-stimulating factor and as a highly efficient chemotactic factor for T cells and monocytes (Bieul et al. (1996) J. Exp. Med. 184:1101-1110).

Biological effects of SDF-1 may be mediated by the chemokine receptor CXCR4 (also known as fusin or LESTR), which is expressed on mononuclear leukocytes including hematopoietic stem cells. SDF-1 is thought to be the natural ligand for CXCR4, and CXCR4 is thought to be the natural receptor for SDF-1 (Nagasawza et al. (1997) Proc. Natl. Acad. Sci. USA 93:726-732). Genetic elimination of SDF-1 is associated with parinatal lethality, including abnormalities in cardiac development, B-cell lymphopoiesis, and bone marrow myelopoiesis (Nagasawa et al. (1996) Nature 382:635-637).

SDF-1 is functionally distinct from other chemokines in that it is reported to have a fundamental role in the trafficking, export and homing of bone marrow progenitor cells (Aiuti, A., Webb, I. J., Bleul, C., Springer, T:, and Guierrez-Ramos, J. C., (1996) J. Exp. Med. 185, 111-120 and Nagasawa, T., Hirota, S., Tachibana, K., Takakura N., Nishikawa, S.-I., Kitamura, Y., Yoshida, N., Kikutani, H., and Kishimoto, T., (1996) Nature 382, 635-638). SDF-1 is also structurally distinct in that it has only about 22% amino acid sequence identity with other CXC chemokines (Bleul, C. C., Fuhlbrigge, R. C., Casasnovas, J. M., Aiuti, A., and Springer, T. A., (1996) J. Exp. Med. 184, 1101-1109;

Katayama, Y., Hidalgo, A., Furie, B. C., Vestweber, D., Furie, B., and Frenette, P. S. (2003). PSGL-1 participates in E-selectin-mediated progenitor homing to bone marrow: evidence for cooperation between E-selectin ligands and alpha4 integrin. Blood 102, 2060-2067). SDF-1 appears to be produced constitutively by several cell types, and particularly high levels are found in bone-marrow stromal cells (Shirozu, M., Nakano, T., Inazawa, J., Tashiro, K., Tada, H. Shinohara, T., and Honjo, T., (1995) Genomics, 28, 495-500 and Bleul, C. C., Fuhlbrigge, R. C., Casasnovas, J. M., Aiuti, A., and Springer, T. A., (1996) J. Exp. Med. 184, 1101-1109). A basic physiological role for SDF-1 is implied by the high level of conservation of the SDF-1 sequence between species. In vitro, SDF-1 stimulates chemotaxis of a wide range of cells including monocytes and bone marrow derived progenitor cells (Aiuti, A., Webb, U., Bleul, C., Springer, T., and Guierrez-Ramos, J. C., (1996) J. Exp. Med. 185, 111-120 and Bleul, C. C., Fuhlbrigge, R. C., Casasnovas, J. M., Aiuti, A., and Springer, T. A., (1996) J. Exp. Med. 184, 1101-1109). SDF-1 also stimulates a high percentage of resting and activated T-lymphocytes (Bleul, C. C., Fuhlbrigge, R. C., Casasnovas, J. M., Aiuti, A., and Springer, T. A., (1996) J. Exp. Med. 184, 1101-1109 and Campbell, J. J., Hendrick, J., Zlotnik, A., Siani, M. A., Thompson, D. A., and Butcher, E. C., (1998) Science, 279 381-383).

Native SDF-1 has been demonstrated to induce the maturation and activation of platelets (Hamada T. et al., J. Exp. Med. 188, 638-548 (1998); Hodohara K. et al., Blood 95, 769-775 (2000); Kowalska M. A. et al., Blood 96, 50-57 (2000)), and CXCR4 is expressed on the megakaryocytic lineage cells (CFUOMeg) (Wang J-F. et al., Blood 92, 756-764 (1998)).

S1PR1 Modulator Agents

S1PR1 modulator agents encompassed in the compositions, methods and kits as disclosed herein are disclosed in Marsolais et al., Nature Reviews Drug Discovery, 2009; 8, 297-307, which is incorporated herein in its entirety by reference.

In some embodiments, a S1PR1 modulator agent is W146, or derivatives or analogues thereof. W146 is also known as: (R)-3-Amino-4-(3-hexylphenylamino)-4-oxobutylphosphonic acid; or 3-amino-4-(3-hexylphenylamino)-4-oxobutyl phosphonic acid, or W146_02-01 or (3R)-3-amino-4-[(3-hexylphenyl)amino]-4-oxobutyl]phosphonic acid, and has the chemical as shown below (Compound II):

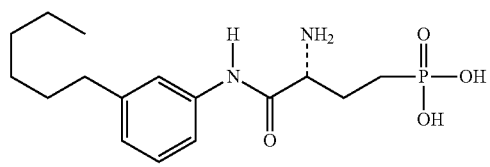 [SMILES: CCCCCCc1cccc(NC(=O)[C@H](N)CCP(=O)(O)O)c1]

W146 is commercially available from Cayman Chemical Company (Cayman Chemical Item Number 10009109). In some embodiment, W146 is in an ionic form in combination with $F_3CCOOH$. W146, and derivatives thereof are disclosed in 2012/0039866, which is incorporated herein in its entirety by reference.

In some embodiments, a S1PR1 modulator agent is AUY954, or derivatives or analogues thereof. AUY945 is known as 3-[[2-[4-phenyl-3-(trifluoromethyl)phenyl]-1-benzothiophen-5-yl]methylamino]propanoic acid, and has the following structure (Compound III):

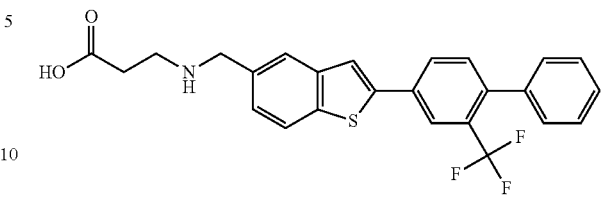

In some embodiments, a S1PR1 modulator agent, e.g., exemplary AUY945 agents for use in the compositions and examples as disclosed herein are disclosed in 2011/0130409, which is incorporated herein by reference in its entirety.

In some embodiments, a S1PR1 modulator agent is FTY720, or derivatives or analogues thereof. FTY720 is also known as: 2-amino-2-[2-(4-octylphenyl)ethyl]propane-1,3-diol; 2-amino-2-[2-(4-octylphenyl)ethyl]-1,3-propanediol, hydrochloride has the following structure (Compound IVa):

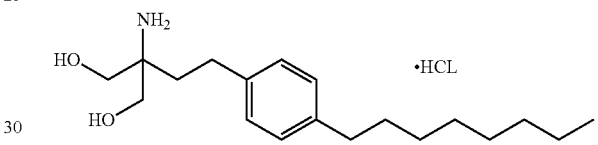

An exemplary S1P receptor agonist having agonist activity on the S1P1 receptor is FTY720 (fingolimod), an immunosuppressive agent currently in clinical trials (Martini et al., Expert Opin. Investig. Drugs, 16:505-518, 2007). FTY720 acts as a prodrug which is phosphorylated in vivo; the phosphorylated derivative is an agonist for S1P1, S1P3, S1P4 and SIPS receptors (but not the S1P2 receptor) (Chiba, Pharmacology & Therapeutics, 108:308-319, 2005). FTY720 has been shown to rapidly and reversibly induce lymphopenia (also referred to as peripheral lymphocyte lowering (PLL); Hale et al., Bioorg. Med. Chem. Lett., 14:3351-3355, 2004). This is attended by clinically useful immunosuppression by virtue of sequestering T- and B-cells in secondary lymphoid tissue (lymph nodes and Peyer's patches) and thus apart from sites of inflammation and organ grafts (Rosen et al., Immunol. Rev., 195:160-177, 2003; Schwab et al., Nature Immunol., 8:1295-1301, 2007).

In clinical trials, FTY720 elicited an adverse event (i.e., transient asymptomatic bradycardia) due to its agonism of the S1P3 receptor (Budde et al., J. Am. Soc. Nephrol., 13:1073-1083, 2002; Sanna et al., J. Biol. Chem., 279: 13839-13848, 2004; Ogawa et al., BBRC, 361:621-628, 2007).

TY720 has been reported to have therapeutic efficacy in at least: a rat model for autoimmune myocarditis and a mouse model for acute viral myocarditis (Kiyabayashi et al., J. Cardiovasc. Pharmacol., 35:410-416, 2000; Miyamoto et al., J. Am. Coll. Cardiol., 37:1713-1718, 2001); mouse models for inflammatory bowel disease including colitis (Mizushima et al., Inflamm. Bowel Dis., 10:182-192, 2004; Deguchi et al., Oncology Reports, 16:699-703, 2006; Fujii et al., Am. J. Physiol. Gastrointest. Liver Physiol., 291:G267-G274, 2006; Daniel et al., J. Immunol., 178:2458-2468, 2007); a rat model for progressive mesangioproliferative glomerulonephritis (Martini et al., Am. J. Physiol. Renal Physiol., 292:F1761-F1770, 2007); a mouse model for asthma, suggested to be primarily through the S1P1 receptor on the basis of work using the S1P1 receptor agonist SEW2871 (Idzko et al, J. Clin. Invest., 116:2935-2944, 2006); a mouse model for airway inflammation and induction of bronchial hyperresponsiveness (Sawicka et al., J. Immunol., 171; 6206-6214, 2003); a mouse model for atopic dermatitis (Kohno et al., Biol. Pharm. Bull., 27:1392-1396, 2004); a mouse model for ischemia-reperfusion injury (Kaudel et al., Transplant. Proc, 39:499-502, 2007); a mouse model for systemic lupus erythematosus (SLE) (Okazaki et al., J. Rheumatol., 29:707-716, 2002; Herzinger et al, Am. J. Clin. Dermatol., 8:329-336, 2007); rat models for rheumatoid arthritis (Matsuura et al., Int. J. Immunopharmacol., 22:323-331, 2000; Matsuura et al., Inflamm. Res., 49:404-410, 2000); a rat model for autoimmune uveitis (Kurose et al., Exp. Eye Res., 70:7-15, 2000); mouse models for type I diabetes (Fu et al, Transplantation, 73:1425-1430, 2002; Maki et al., Transplantation, 74:1684-1686, 2002; Yang et al., Clinical Immunology, 107:30-35, 2003; Maki et al., Transplantation, 79:1051-1055, 2005); mouse models for atherosclerosis (Nofer et al., Circulation, 115:501-508, 2007; Keul et al., Arterioscler. Thromb. Vasc. Biol., 27:607-613, 2007); a rat model for brain inflammatory reaction following traumatic brain injury (TBI) (Zhang et al., J. Cell. Mol. Med., 11:307-314, 2007); and mouse models for graft coronary artery disease and graft-versus-host disease (GVHD) (Hwang et al., Circulation, 100:1322-1329, 1999; Taylor et al., Blood, 110:3480-3488, 2007). In vitro results suggest that FTY720 may have therapeutic efficacy for β-amyloid-related inflammatory diseases including Alzheimer's disease (Kaneider et al., FASEB J., 18:309-311, 2004). KRP-203, an SIP receptor agonist having agonist activity on the S1P1 receptor, has been reported to have therapeutic efficacy in a rat model for autoimmune myocarditis (Ogawa et al., BBRC, 361:621-628, 2007). Using the S1P1 receptor agonist SEW2871, it has been shown that agonism of endothelial S1P1 receptors prevents proinflammatory monocyte/endothelial interactions in type I diabetic vascular endothelium (Whetzel et al., Circ. Res., 99:731-739, 2006) and protects the vasculature against TNFα-mediated monocyte/endothelial interactions (Bolick et al., Arterioscler. Thromb. Vasc. Biol., 25:976-981, 2005).

Additionally, FTY720 has been reported to have therapeutic efficacy in experimental autoimmune encephalomyelitis (EAE) in rats and mice, a model for human multiple sclerosis (Brinkmann et al., J. Biol. Chem., 277:21453-21457, 2002; Fujino et al., J. Pharmacol. Exp. Ther., 305: 70-77, 2003; Webb et al., J. Neuroimmunol., 153:108-121, 2004; Rausch et al., J. Magn. Reson. Imaging, 20:16-24, 2004; Kataoka et al., Cellular & Molecular Immunology, 2:439-448, 2005; Brinkmann et al., Pharmacology & Therapeutics, 115:84-105, 2007; Baumruker et al., Expert Opin. Investig. Drugs, 16:283-289, 2007; Balatoni et al., Brain Research Bulletin, 74:307-316, 2007). Furthermore, FTY720 has been found to have therapeutic efficacy for multiple sclerosis in clinical trials. In Phase II clinical trials for relapsing-remitting multiple sclerosis, FTY720 was found to reduce the number of lesions detected by magnetic resonance imaging (MRI) and clinical disease activity in patients with multiple sclerosis (Kappos et al., N. Engl. J. Med., 355:1124-1140, 2006; Martini et al., Expert Opin. Investig. Drugs, 16:505-518, 2007; Zhang et al., Mini-Reviews in Medicinal Chemistry, 7:845-850, 2007; Brinkmann, Pharmacology & Therapeutics, 115:84-105, 2007). FTY720 is currently in Phase III studies of remitting-relapsing multiple sclerosis (Brinkmann, Pharmacology & Therapeutics, 115:84-105, 2007; Baumruker et al., Expert. Opin. Investig. Drugs, 16:283-289, 2007; Dev et al., Pharmacology and Therapeutics, 117:77-93, 2008).

FTY720 is commercially available, for example, from Cayman Chemical Company (Cayman Chemical Item Number 10006292)(CAS 162359-56-0). FTY720 is also known in the art as Fingolimod or GILENYA™ and its structure and derivatives are disclosed in U.S. Pat. No. 7,811,822, which is incorporated herein in its entirety by reference. In some embodiments, FTY720 is provided in the presence of HCl. In some embodiments, a S1PR1 modulator is a prodrug of FTY720, which includes, but is not limited to FTY720-P, which has the following structure (Compound IVb).

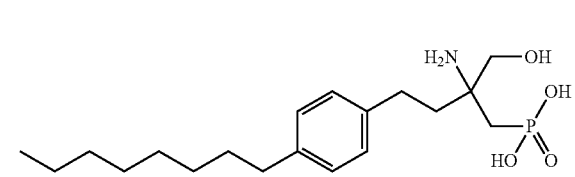 [SMILES: CCCCCCCCc1ccc(CCC(N)(CO)CP(=O)(O)O)cc1]

Figure 24:
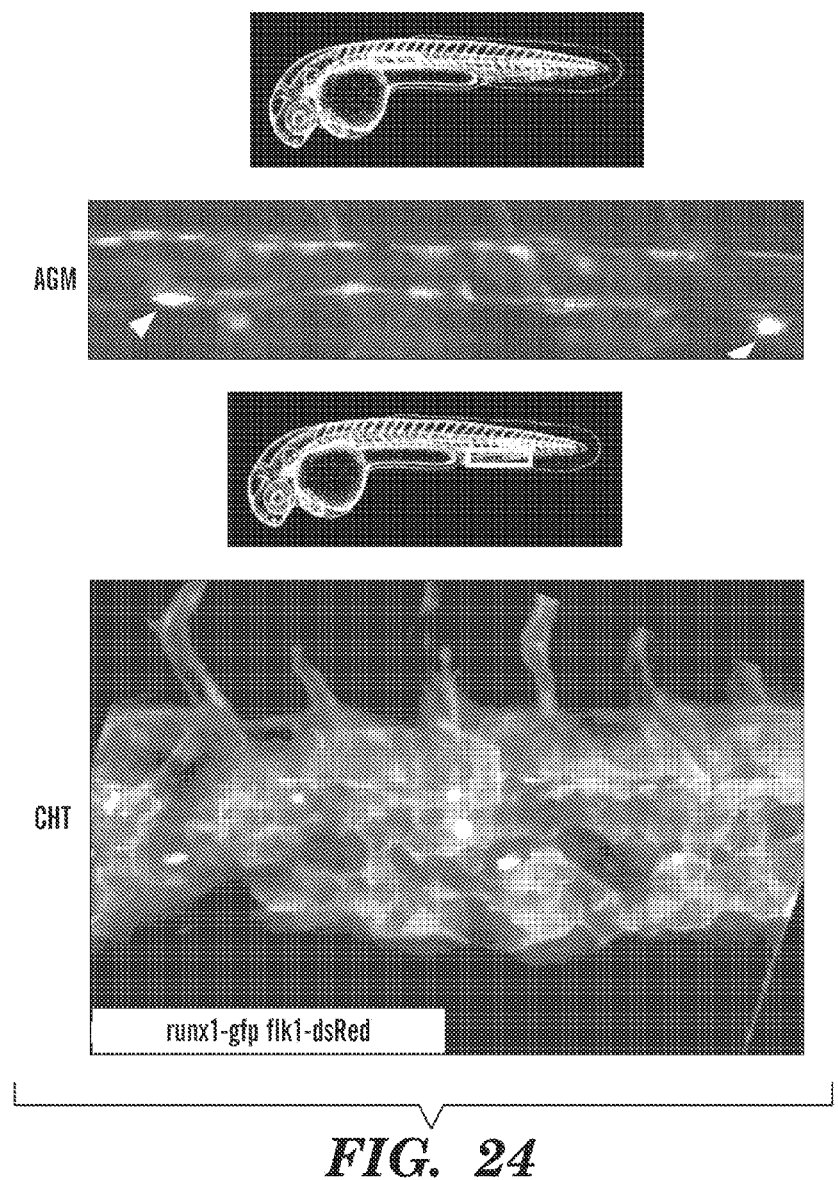
FIG. 24 shows Runx1 reporter labels hematopoietic stem and progenitor cells in the AGM and CHT. To follow colonization in vivo the inventors produced a transgenic line to mark definitive HSPCs in zebrafish that were specific and expressed at a high levels to identify the HSCs. Using the HSPC-specific enhancer from the first intron of the Runx1 locus, originally characterized in the lab of Marella de Bruijn, placed upstream of a minimal promoter driving GFP, HSC-specific expression identified by GFP expression was established in the zebrafish.
Figure 25:
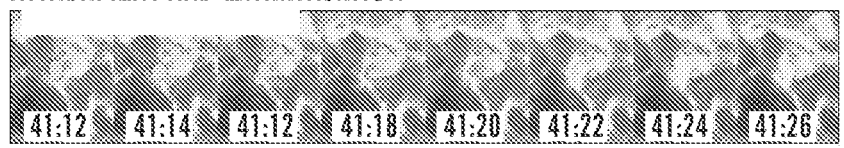
FIG. 25 shows green HSCs green emerging from the DA in red at about 36 hpf. The boxed area in the zebrafish schematics indicate the area of the zebrafish shown in the imaged panels. This zebrafish model was used for time-lapse live imaging of CHT colonization.
Figure 25:
Figure 25:
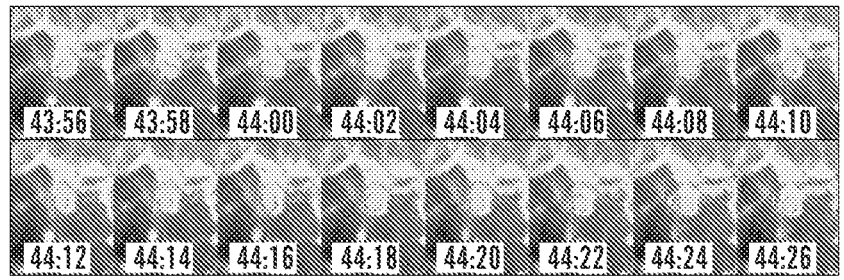
Figure 26A:
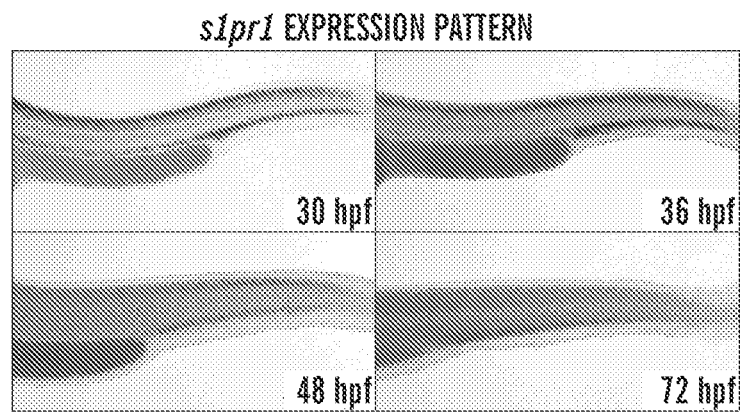
FIG. 26A-26B shows sphingosine-1-phosphate receptor 1 (s1pr1) expression and function during CHT colonization.
Figure 26B:
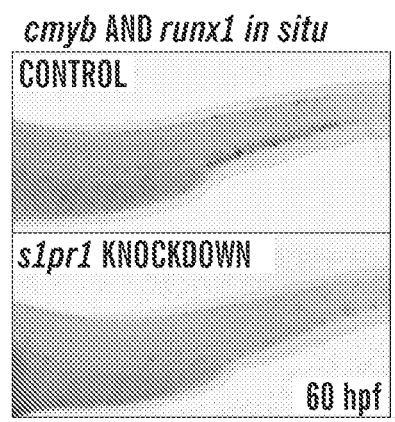
Figure 27:
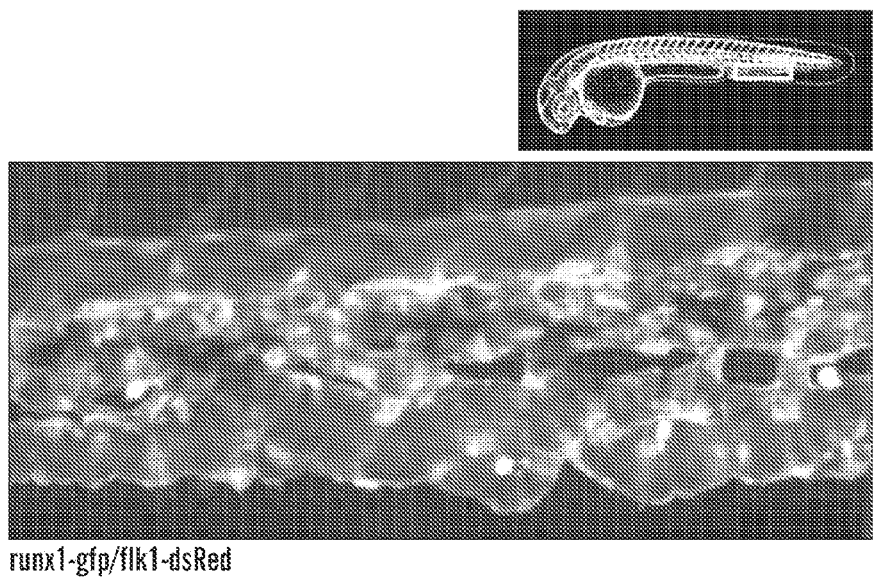
FIG. 27 shows S1PR1 antagonist (W146) interferes with CHT colonization. Using the time-lapse live imaging with our runx1-reporter line, the embryos in the chemical antagonist during embryo imaging. HSCs (identified by GFP expression) were still arriving in the CHT (thus they were still being produced), but they failed to engraft. Surprisingly, HSCs would adhere briefly to the endothelial cells in the vascular plexus, but would not undergo extravasation.
Figure 28:
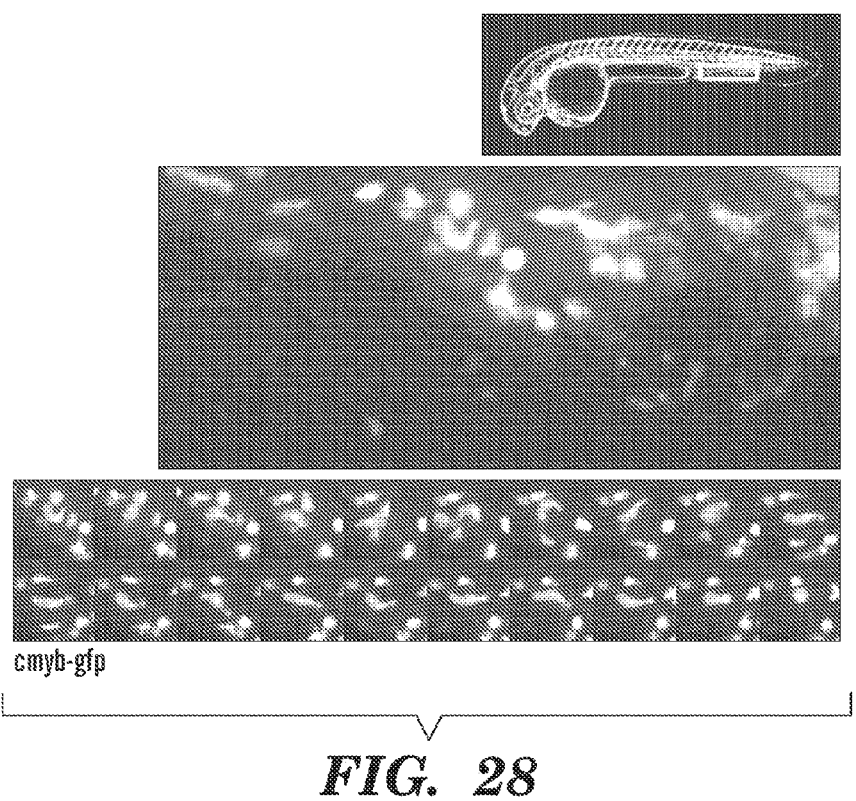
In FIG. 28, a HSC progenitor cell would arrive in the CHT but fails to undergo any of the colonization steps after adhering to the vessel wall. The boxed area in the zebrafish schematic indicates the area of study analyzed in the live imaging.
Figure 29:
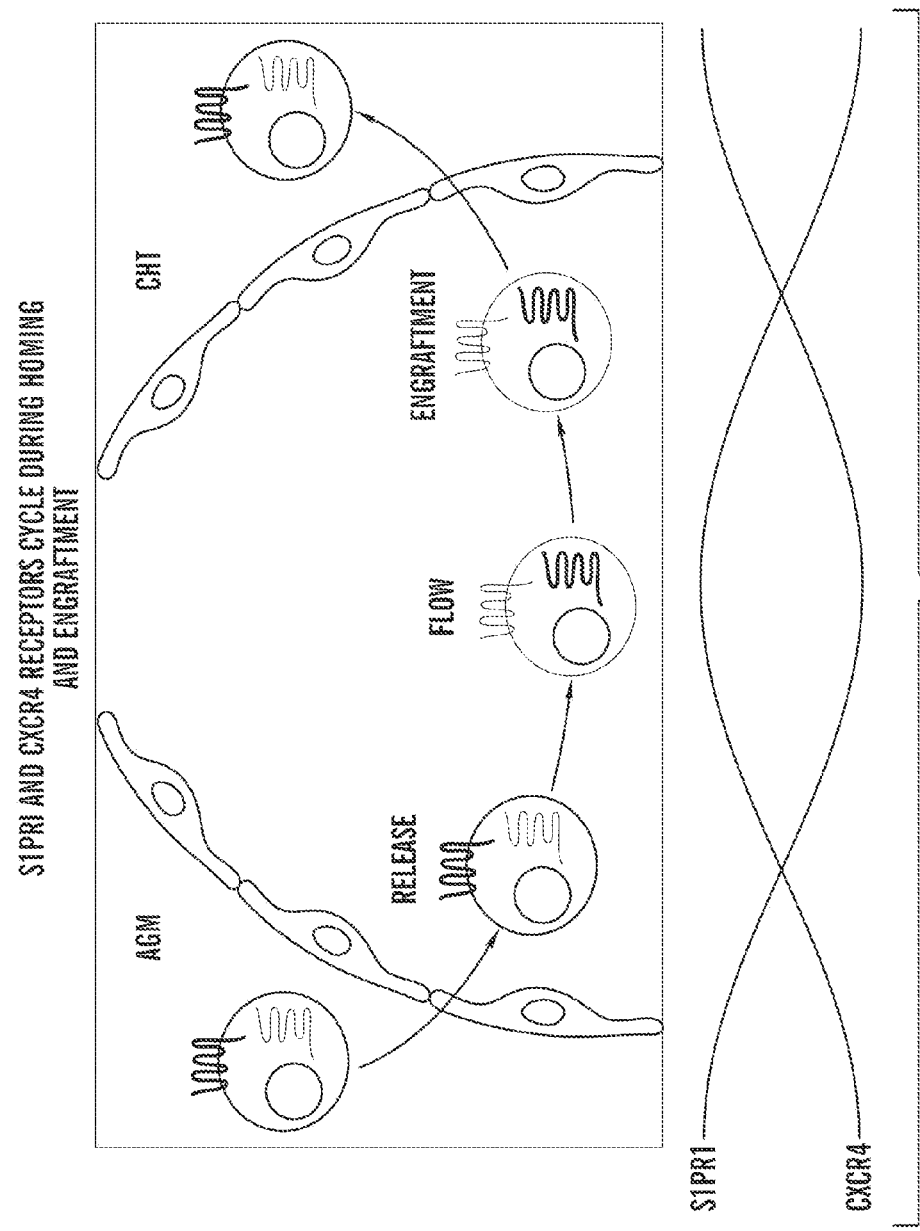
FIG. 29 shows a schematic of S1PR1 and CXCR4 receptors cycling during homing and engraftment. The inventors demonstrate herein that treatment with antagonist against either S1PR1 and CXCR4 receptors results in decreased hematopoiesis in the CHT. Accordingly, there is cycling between these two receptors during migration of HSPCs from the DA to the CHT. S1PR1 receptor is high when the stem cells are in the DA and when they are first released into circulation. The S1P receptor is quickly internalized once in circulation, where S1P levels are high, and CXCR4 receptor rapidly moves to the cell surface. This enables the cell to respond to high SDF-1 levels on endothelial cells in the CHT. Finally, migration of the stem cell from the lumen to the abluminal side requires recycling of S1PR1 to the cell surface. Accordingly, this model allows one of ordinary skill in the art to predict an optimal ratio of these receptor levels to promote mobilization or engraftment.
Figure 30:
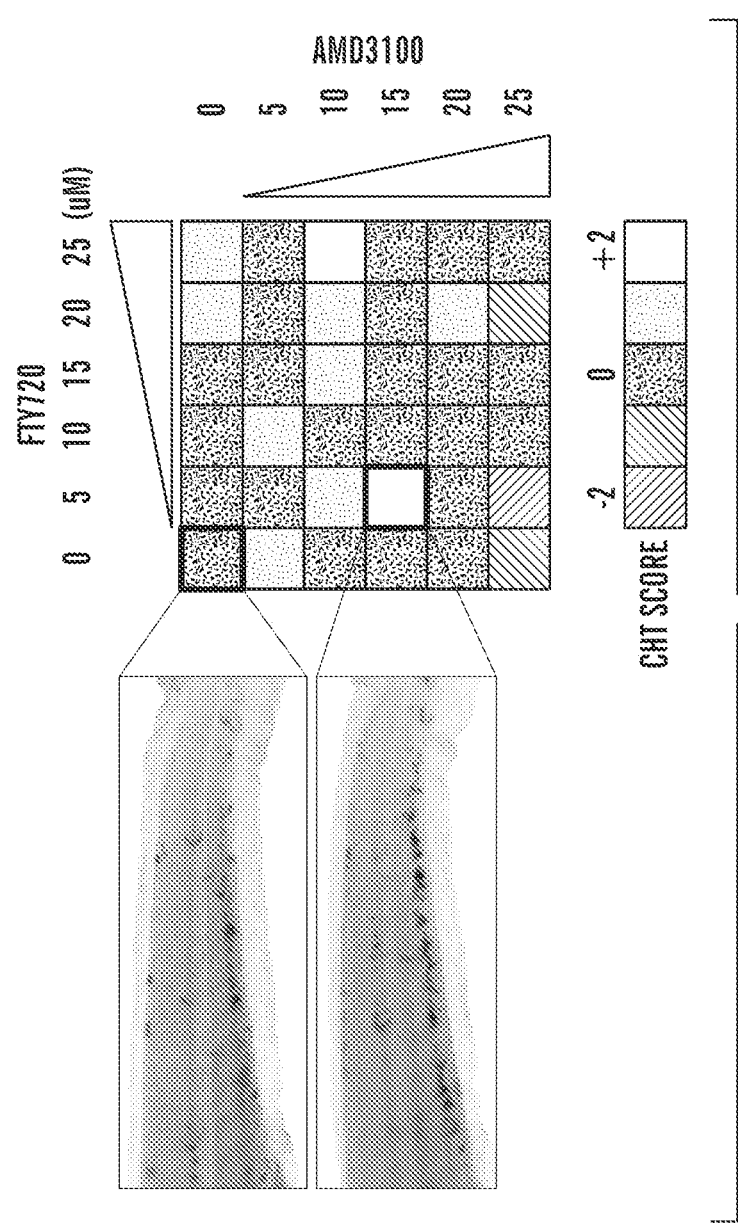
FIG. 30 shows the combined effect of S1PR1 and CXCR4 antagonists increases CHT colonization. A chemical genetic interaction matrix between the CXCR4 antagonist AMD3100, (which used alone, decreases CHT hematopoiesis), and FTY720, an S1P analogue that functions as a functional antagonist of S1P receptor. Engraftment was assessed in this integration matrix of increasing concentrations of the FTY720 compound were used across the X-axis from left to right, and increasing concentrations the AMD3100 drug was used along the Y-axis from top to bottom. The combination of FTY720 and AMD3100 at specific combined doses increased CHT hematopoiesis, however, the doses alone had no effect.

As used herein, the term "FTY720 derivative or analog" refers to a compound, natural or synthetic, that is structurally similar to FTY720 suitable for use in the instant invention but does not include FTY720 (2-amino-2-(4-octylphenethyl) propane-1,3-diol). In certain embodiments, the FTY720 analog or derivative is effective in treating or reducing the risks of developing ALI; in certain particular embodiments, the FTY720 analog or derivative is effective in treating or reducing the risks of developing radiation induced- or lung trauma-induced ALI. In certain embodiments, the FTY720 analog or derivative is effective in treating or reducing the risks of developing ALI in a mammal result from dysregulation of the ceramide/sphingolipid pathway. In certain other embodiments, the FTY720 analog or derivative is effective in reducing vascular leakage or vascular permeability in the lung, or reducing the risk of developing vascular leakage or increased vascular permeability in the lung of a mammal, reducing acute lung inflammation in a mammal, increasing alveolar cell integrity or increasing endothelial cell integrity in a mammal, reducing BAL protein levels or BAL cell count in a mammal, and/or reducing weight loss or hair loss associated with thoracic radiation therapy in a mammal. FTY720 derivatives or analogs include, without limitation, the (R) or (5) enantiomer of FTY720-phosphonate, the (R) or (S) enantiomer of FTY720-enephosphonate, and the (R) or (5) enantiomer of FTY720 regioisomer (3-(aminomethyl)-5-(4-octylphenyl)pentane-1,3-diol), as shown in FIG. 24, or pharmaceutically acceptable salts thereof. In certain embodiments, the FTY720 analog or derivative is an FTY720-phosphonte, including the (R) and (S) enantiomers of FTY720-phosphonate, i.e., enantiomerically enriched or purified preparations of (R)- and (5*)-3-amino-3-(hydroxymethyl)-5-(4-octylphenyl)pentylphosphonic acid, and the (R) and (5) enantiomer of FTY720-enephosphonate, i.e., enantiomerically enriched or purified preparations of (R)- and (S)-3-amino-3-(hydroxymethyl)-5-(4-octylphenyl)pent-1-enylphosphonic acid. In certain particular embodiments, the FTY720 analog or derivative is FTY720-phosphonte, including the (R) and (S) enantiomers of FTY720-phosphonate, i.e., enantiomerically enriched or purified preparations of (R)- or (5*)-3-amino-3-(hydroxymethyl)-5-(4-octylphenyl)pentylphosphonic acid. In certain advantageous embodiments, the FTY720 analog or derivative is (5)-FTY720-phosphonte, also referred to as Tysiponate, Tysip, TyS, Tys, fTyS, or IS throughout the instant application. In certain particular embodiments, the FTY720 analog or derivative does not include FTY720-phosphate (p-FTY720). The structure of (5)-FTY720-phosphonte (Tysiponate) is shown below: In some embodiments, a S1PR1 modulator agent is a FTY720-derived agent or FTY720 analogue or derivative such as those disclosed in US Application 2012/0136063 or 2011/109650 which are incorporated herein in its entirety by reference.

In some embodiments a S1PR1 modulator agent or compound is a derivative of FTY720. In some embodiments, a S1PR1 modulator agent is of formula (I):

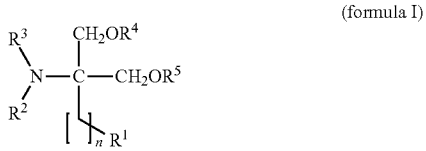

(formula I)

wherein:
$R^1$ is a straight- or branched-aliphatic, aryl, heteroaryl, cyclyl, or heterocyclyl, each of which can be optionally substituted;
$R^2$ and $R^3$ are the same or different and each is a hydrogen, an alkyl, an aralkyl, an acyl, or an alkoxycarbonyl, each of which can be optionally substituted;
$R^4$ and $R^5$ are the same or different and each is a hydrogen, an alkyl, an aralkyl, an acyl, an alkoxycarbonyl, or $P(O)(OR^6)_2$, each of which can be optionally substituted, or $R^4$ and $R^5$ can be bonded to form an alkylene chain, which can be optionally substituted;
$R^6$ is independently for each occurrence hydrogen, a negative charge, aliphatic, aryl, heteroaryl, cyclyl, or heterocyclyl, each of which can be optionally substituted;
n is 0, 1, 2, 3, 4, 5, 6, 7, 8, 9, or 10;
and pharmaceutically acceptable salts thereof.

In some embodiments, n is 2.

In some embodiments, $R^1$ is an optionally substituted phenyl. In some embodiments, $R^1$ is a phenyl group substituted with 1, 2, 3, 4, or 5 aliphatic groups, which can all be same, all different, or a combination of same and different. When the phenyl is substituted, the substituent can be located at the o-, m- or p-position relative to the site where the phenyl group is binds to the rest of formula (I). In some embodiments, the phenyl group can be substituted with an optionally substituted straight- or branched chain $C_6$-$C_{14}$ alkyl, an optionally substituted straight- or branched chain $C_6$-$C_{14}$ alkoxy, or an optionally substituted straight- or branched chain $C_6$-$C_{14}$ alkenyloxy. In one embodiment, $R^1$ is 4-octylphenyl.

In some embodiments, $R^2$ and $R^3$ are both different. In some embodiments, $R^2$ and $R^3$ are both different and one of $R^2$ and $R^3$ is H. In some embodiments, $R^2$ and $R^3$ are both same. In some embodiments, $R^2$ and $R^3$ are both H.

In some embodiments, at least one of $R^4$ and $R^5$ is H. In some embodiments, at least one of $R^4$ and $R^5$ is not H. In some embodiments, one of $R^4$ and $R^5$ is $P(O)(OR^6)_2$ and the other is H.

In some embodiments, at least one $R^6$ is H. In some embodiments, at least one $R^6$ is a negative charge.

Exemplary compounds of formula (I) include, but are not limited to, 2-amino-2-tridecyl-1,3-propanediol, 2-amino-2-tetradecyl-1,3,-propanediol, 2-amino-2-pentadecyl-1,3-propanediol, 2-amino-2exadecyl-1,3-propanediol, 2-amino-2-heptadecyl-1,3-propanediol, 2-amino-2octadecyl-1,3-propanediol, 2-amino-2-nonadecyl-1,3propanediol, 2-amino-2-icosyl-13-propanediol, 2-amino-2-(12-fluorododecyl)-1,3-propanediol, 2-amino-2(14-fluorotetradecyl)-1, 3-propanediol, 2-amino-2-(8-phenyloctyl)-13-propanediol, 2-amino-2-(9-phenylnonyl)-13-propanediol, 2-amino-2(10-phenyldecyl)-1,3-propanediol, 2-amino-2-(11-phenylundecyl)-1,3-propanediol, 2-amino-2-(12phenyldodecyl)-1,3-propanediol, 2-amino-2-(13phenyltridecyl)-1,3-propanediol, 2-amino-2-(14-phenyltetradecyl)-1,3-propanediol, 2-amino-2-(15phenylpentadecyl)-1,3-propanediol, 2-amino-2-(16phenylhexadecyl)-1,3-propanediol, 2-amino-2-[6-(8phenyloctyloxy)hexyl]-1,3-propanediol, 2-amino-2-(8phenylmethyloxyoctyl)-1,3-propanediol, 2-amino-2-(9phenoxynonyl)-1,3-propanediol, 2-amino-2-(12phenoxydodecyl)-13-propanediol, 2-amino-2-[6-(2phenoxyethyloxy)hexyl]-1,3-propanediol, 2-amino-2-(10-phenyldecyl)-1,3propanediol, 2-amino-2-(13-phenyltridecyl)-1,3propanediol, 2-amino-2-[6-(8-phenyloctyloxy)hexyl]-1,3-propanediol, 2-amino-2-(8-phenylmethyloxyocryl)-13propanediol, 2-amino-2-(9-phenoxynonyl)-1,3prepanediol, 2-amino-2-(12-phenoxydodecyl)-1,3 propanediol, 2-amino-2-[6-(2-phenoxyethyloxy)hexyl]-1,3-propanediol, 2-amino-2-[2(4-phenylmethyloxyphenyl)ethyl]-1,3-propanediol, 2-amino-2-[2(4-(2-phenylethyloxy)phenyl)ethyl]-1,3propanediol, 2-amino-2-[2-(4-(3-phenylpropyloxy)phenyl)ethyl]-1,3-propanediol, 2-amino-2-[2-(4-(4phenylbutyloxy)phenyl)ethyl]-13-propanediol, 2-amino-2-[2-(4-(5-phenylpentyloxy)phenyl)ethyl]-1,3propanediol, 2-amino-2-[2-(14-(6-phenylhexyloxy)phenyl)ethyl]-1,3-propanediol, 2-amino-2-[2-(4-(7-phenylheptyloxy)phenyl)ethyl]-1,3-propanediol, 2-amino-2-[2(4-(8-phenyloctyloxy)phenyl)ethyl]-1,-propanediol, 2-amino-2-[4-(6-(4-fluorophenyl)hexyloxy)phenyl)ethyl]-1,3-propanediol, 2-amino-2-[2-(4-(5phenylpentyloxymethyl)phenyl)ethyl]-1,3-propanediol, 2-amino-2-[2-(4-(4-phenoxyburyloxy)phenyl)ethyl]-1,3propanediol, 2-amino-2-[2-(4-(5-phenoxypentyloxy)phenyl)ethyl]-1,3-propanediol, 2-amino-2-[2-(4-(6-phenoxyhexyloxy)phenyl)ethyl]-1,3-propanediol, 2-amino-2-[2-(4-(7-phenoxyheptyloxy)phenyl)ethyl]-1,3-propanediol, 2-amino-2-[2-(4-(4-phenoxybutyl)phenyl)ethyl]-1,3-propanediol, 2-amino-2-[2-(4-(5-phenoxypentyl)phenyl)ethyl]-1,3-propanediol, 2-amino-2-[2-(4-(6-phenoxyhexyl)phenyl)ethyl]-1,3propanediol, 2-amino-2-[2-(4-(7-phenoxyheptyl)phenyl)ethyl]-13-propanediol, -amino-2-[2-(4-(6-phenylhexyloxy)phenyl)ethyl]-13-propanediol, 2-amino-2-[2-(4-(5-phenylpentyloxymethyl)phenyl)ethyl]-1,3-propanediol, 2-amino-2-[2-(5-octyl-2-thienyl)ethyl]-1,3propanediol, 2-amino-2-[2-(5-nonyl-2-thienyl)ethyl]-1,3propanediol, 2-amino-2-[2-(5-decyl-2-thienyl)ethyl]-1,3propanediol, 2-amino-2-[2-(5-dodecyl-2-thienyl)ethyl]-1,3-propanediol, 2-amino-2-[13(2-thienyl)tridecyl]-13propanediol, 2-amino-2-[2(5-octyl-2-pyridyl)ethyl]-1,3propanediol. 2-amino-2-[2-(5-decyl-2-pyridyl)ethyl]-1,3-propanediol, 2-amino-2-[13-(2-pyridyl)tridecyl]-1,3-propanediol, 2-amino-2-[2-(2-octyl-5-pyridyl)ethyl]-13propanediol, 2-amino-2-[2-(2-decyl-5-pyridyl)ethyl]-1,3-propanediol, 2-amino-2-[13-(3-pyridyl)tridecyl]-1,3-propanediol, 2-amino-2-[2-(1-ortylpiperidin-4-yl)ethyl]-1,3-propanediol, 2-amino-2-[2-(1-dodecylpiperidin-40-ethyl]-1,3-propanediol, 2-amino-2-(4-decylphenyl)-1,3propanediol, 2-amino-2-(4-dodecylphenyl)-1,3propanediol, 2-amino-2(4-tetradecylphenyl)-1,3 propanediol, 2-amino-2(4-hexadecylphenyl)-1,3propanediol, 2-amino-2-(4-octylphenoxymethyl)1,3-propanediol, 2-amino-2-(4-decylphenoxymethyl)-1,3-propanediol, 2-amino-2(4-dodecylphenoxymethyl)-1,3-propanediol, 2-amino-2-

(4tetradecylphenoxymethyl)-1,3-propanediol, 2-amino-2-(1,2,12-trihydroxy-4-25 consisting of alkoxy, alkenyloxy, alkynyloxy, aralkyloxy, octadecenyl)-1,3-propanediol, 2-amino-2-(1,2-alkylenedioxy, acyl, alkylamino, alkylthio, acylamino, dihydroxy-4-octadecenyl)-13-propanediol, 2-amino-2-alkoxycarbonyl, alkoxycarbonylamino, acyloxy, (1,2-dihydroxyoctadecyl)-13-propanediol, 2-amino-2-<1, alkylcarbamoyl, haloalkyl, haloalkoxy, nitro, halogen, 12-dihydroxy-4-octadecenyl)-13-propanediol, 2-amino-amino, hydroxy, carboxy, optionally substituted aryl, option 2-(1,2,4-trihydroxybutyl)-1,3-propanediol, 2-amino-2-(1, 30ˆsubstituted aryloxy, optionally substituted cycloalkyl, 2,12-trihydroxyoctadecyl)-13-propanediol, 2-amino-2-[2-(4-heptylphenyl)ethyl]-1,3-propanediol, 2-amino-2-[2-(4-octylphenyl)ethyl]-1,3-propanediol (FTY720), 2-amino-2-[2-(4-nonylphenyl)ethyl]-13propanediol, 2-amino-2-[2-(4-decylphenyl)ethyl]-1,3-propanediol, 2-amino-2-[2-(4-undecylphenyl)ethyl]-1,3-propanediol, 2-amino-2-[2-(4-dodecylphenyl)ethyl]-13propanediol, 2-amino-2-[2-(4-tridecylphenyl)ethyl]-13propanediol, 2-amino-2-[2-(4-tetradecylphenyl)ethyl]-1,3-propanediol, 2-amino-2-[2-(4-hexyloxyphenyl)ethyl]13-propanediol, 2-amino-2-[2-(4-heptyloxyphenyl)ethyl]-1,3-propanediol, 2-amino-2-[2-(4-octyloxyphenyl)ethyl]-1,3-propanediol, 2-amino-2-[2-(4nonyloxyphenyl)ethyl]-1,3-propanediol, 2-amino-2-[2(4-decyloxyphenyl)ethyl]-1,3-propanediol, 2-amino-2-[2-(4-undecyloxyphenyl)ethyl]-1,3-propanediol, 2-amino-2-[2-(4-dodecyloxyphenyl)ethyl]-1,3propanediol, 2-amino-2-[2-(4-tridecyloxyphenyl)ethyl]13-propanediol, 2-amino-2-[2-(4-(8-fluorooctyl)phenyl)ethyl]-1,3-propanediol, 2-amino-2-[2-(4-(12-fluorododecyl)phenyl)ethyl]-1,3-propanediol, 2-amino-2[2-(4-(7-fluoroheptyloxy)phenyl)ethyl]-1,3-propanediol, 2-amino-2-[2-[2-(4-(11-fluoroundecyloxy)phenyl)ethyl]-1,3-propanediol, 2-amino-2-[2-(4-(7-octenyloxy)phenyl)ethyl]-13-propanediol, 2-amino-2-[2-(4-heptylphenyl)ethyl]-1,3-propanediol, 2-amino-2-[2-(4-octylphenyl)ethyl]-1,3-propanediol, 2-amino-2-[2-(4-nonylphenyl)ethyl]-1,3-propanediol, 2-amino-2-[2-(4-decylphenyl)ethyl]-1,3-propanediol, 2-amino-2-[2-(4-undecylphenyl)ethyl]-13propanediol, 2-amino-2-[2-(4-dodecylphenyl)ethyl]-1,3-propanediol, 2-amino-2-[2-(4-heptyloxyphenyl)ethyl]-1,3-propanediol, 2-amino-2-[2-(4-octyloxyphenyl)ethyl]-1,3-propanediol, 2-amino-2-[2-(4-nonyloxyphenyl)ethyl]-1,3-propanediol, 2-amino-2-[2-(4-undecyloxyphenyl)ethyl]-1,3-propanediol, 2-amino-2-[2-(4-(7octenyloxy)phenyl)ethyl]-1,3-propanediol, and a pharmaceutically acceptable salt thereof. Additional exemplary compounds of formula (I) are described for example in U.S. Pat. No. 5,719,176, content of which is incorporated herein by reference in its entirety.

In some embodiments the compound of formula (I) is 2-amino-2-[2-(4-octylphenyl)ethyl]-1,3-propanediol (FTY720) or 2-amino-2[2-(4-octylphenyl)ethyl]-1,3-propanediol, mono dihydrogen phosphate ester (FTY720-P).

The term "aliphatic", as used herein, means straight-chain, branched or cyclic $C_1$-$C_{12}$ hydrocarbons which are completely saturated or which contain one or more units of unsaturation, but which are not aromatic. For example, suitable aliphatic groups include substituted or unsubstituted linear, branched or cyclic alkyl, alkenyl, alkynyl groups and hybrids thereof, such as cycloalkyl, (cycloalkyl)alkyl, (cycloalkenyl) alkyl or (cycloalkyl)-alkenyl. In various embodiments, the aliphatic group has one to ten, one to eight, one to six, one to four, or one, two, or three carbons.

The terms "alkyl", "alkenyl", and "alkynyl", used alone or as part of a larger moiety, refer to a straight and branched chain aliphatic group having from one to twelve carbon atoms. For purposes of the present invention, the term "alkyl" will be used when the carbon atom attaching the aliphatic group to the rest of the molecule is a saturated carbon atom. However, an alkyl group can include unsaturation at other carbon atoms. Thus, alkyl groups include, without limitation, methyl, ethyl, propyl, allyl, propargyl, butyl, pentyl, and hexyl.

The term "alkoxy" refers to an —O-alkyl radical.

For purposes of the present disclosure, the term "alkenyl" will be used when the carbon atom attaching the aliphatic group to the rest of the molecule forms part of a carboncarbon double bond. Alkenyl groups include, without limitation, vinyl, 1-propenyl, 1-butenyl, 1-pentenyl, and 1-hexenyl.

For purposes of the present disclosure, the term "alkynyl" will be used when the carbon atom attaching the aliphatic group to the rest of the molecule forms part of a carbon-carbon triple bond. Alkynyl groups include, without limitation, ethynyl, 1-propynyl, 1-butyryl, 1-pentynyl, and 1-hexynyl.

The term "cycloaliphatic", used alone or as part of a larger moiety, refers to a saturated or partially unsaturated cyclic aliphatic ring system having from 3 to about 14 members, wherein the aliphatic ring system is optionally substituted. In some embodiments, the cycloaliphatic is a monocyclic hydrocarbon having 3-8 or 3-6 ring carbon atoms. Nonlimiting examples include cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloaliphatic is a bridged or fused bicyclic hydrocarbon having 6-12, 6-10, or 6-8 ring carbon atoms, wherein any individual ring in the bicyclic ring system has 3-8-members.

In some embodiments, two adjacent substituents on a cycloaliphatic ring, taken together with the intervening ring atoms, form an optionally substituted fused 5- to 6-membered aromatic or 3- to 8-membered non-aromatic ring having 0-3 ring heteroatoms selected from the group consisting of O, N, and S. Thus, the term "cycloaliphatic" includes aliphatic rings that are fused to one or more aryl, heteroaryl, or heterocyclyl rings, where the radical or point of attachment is on the aliphatic ring. Nonlimiting examples include indanyl, 5,6,7,8-tetrahydroquinoxalinyl, decahydronaphthyl, or tetrahydronaphthyl, where the radical orpoint of attachment is on the aliphatic ring.

The terms "haloaliphatic", "haloalkyl", "haloalkenyl" and "haloalkoxy" refer to an aliphatic, alkyl, alkenyl or alkoxy group, as the case can be, which is substituted with one or more halogen atoms. As used herein, the term "halogen" or "halo" means F, Cl, Br, or I. The term "fluoroaliphatic" refers to a haloaliphatic wherein the halogen is fluoro.

Nonlimiting examples of fluoroaliphatics include —$CH_2F$, —$CHF_2$, —$CH_3$, —$CH_2CH_{3y}$, —$CH_2CH_3$, and —$CH_2CH_3$.

The terms "aryl" and "ar-", used alone or as part of a larger moiety, e.g., "aralkyl", "aralkoxy", or "aryloxyalkyl", refer to a $C_6$ to $C_{14}$ aromatic hydrocarbon, comprising one to three rings, each of which is optionally substituted. Preferably, the aryl group is a $C_{6-10}$ aryl group. Aryl groups include, without limitation, phenyl, naphthyl, and antllracenyl. In some embodiments, two adjacent substituents on an aryl ring, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the term "aryl", as used herein, includes groups in which an aromatic ring is fused to one or more heteroaryl, cycloaliphatic, or heterocyclyl rings, where the radical or point of attachment is on the aromatic ring. Nonlimiting examples of such fused ring systems include indolyl, isoindolyl, benzothienyl, benzofuranyl, dibenzofuranyl, indazolyl, benzimidazolyl, benzthiazolyl, quinolyl, isoquinolyl, quinolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl. An aryl group can be mono-, bi-, tri-, or polycyclic, preferably mono-, bi-, or tricyclic, more preferably mono- or bicyclic. The term "aryl" can be used interchangeably with the terms "aryl group", "aryl moiety", and "aryl ring."

An "aralkyl" or "arylalkyl" group comprises an aryl group covalently attached to an alkyl group, either of which independently is optionally substituted. Preferably, the aralkyl group is $C_{6-10}$ aryl($C_{6-10}$)alkyl, including, without limitation, benzyl, phenethyl, and naphthylmethyl.

The terms "heteroaryl" and "heteroar-", used alone or as part of a larger moiety, e.g., heteroaralkyl, or "heteroaralkoxy", refer to groups having 5 to 14 ring atoms, preferably 5, 6, 9, or 10 ring atoms; having 6, 10, or $14\pi$ electrons shared in a cyclic array; and having, in addition to carbon atoms, from one to four heteroatoms. The term "heteroatom" refers to nitrogen, oxygen, or sulfur, and includes any oxidized form of nitrogen or sulfur, and any quaternized form of a basic nitrogen. Thus, when used in reference to a ring atom of a heteroaryl, the term "nitrogen" includes an oxidized nitrogen (as in pyridine N-oxide). Certain nitrogen atoms of 5-membered heteroaryl groups also are substitutable, as further defined below. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl.

In some embodiments, two adjacent substituents on a heteroaryl ring, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzotllienyl, benzofuranyl, dibenzofuranyl, indazolyl, benzimidazolyl, benzthiazolyl, quinolyl, isoquinolyl, cirmolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. A heteroaryl group can be mono-, bi-, tri-, or polycyclic, preferably mono-, bi-, or tricyclic, more preferably mono- or bicyclic. The term "heteroaryl" can be used interchangeably with the terms "heteroaryl ring", or "heteroaryl group", any of which terms include rings that are optionally substituted. The term "heteroaralkyl" refers to an alkyl group substituted by a heteroaryl, wherein the alkyl and heteroaryl portions independently are optionally substituted.

As used herein, the terms "aromatic ring" and "aromatic ring system" refer to an optionally substituted mono-, bi-, or tricyclic group having 0-6, preferably 0-4 ring heteroatoms, and having 6, 10, or $14\pi$ electrons shared in a cyclic array. Thus, the terms "aromatic ring" and "aromatic ring system" encompass both aryl and heteroaryl groups.

As used herein, the terms "heterocycle", "heterocyclyl", "heterocyclic radical", and "heterocyclic ring" are used interchangeably and refer to a stable 3- to 7-membered monocyclic, or to a fused 7- to 10-membered or bridged 6- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a heterocyclyl ring having 1-3 heteroatoms selected from oxygen, sulfur or nitrogen, the nitrogen can be N (as in 3,4-dihydro-2H-pyrrolyl), NH (as in pyrrolidinyl), or $^+$NR (as in N-substituted pyrrolidinyl). A heterocyclic ring can be attached to its pendant group at any heteroatom or carbon atom that results in a stable structure, and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl.

In some embodiments, two adjacent substituents on a heterocyclic ring, taken together with the intervening ring atoms, form an optionally substituted fused 5 to 6-membered aromatic or 3- to 8-membered non-aromatic ring having 0-3 ring heteroatoms selected from the group consisting of O, N, and S. Thus, the terms "heterocycle", "heterocyclyl", "heterocyclyl ring", "heterocyclic group", "heterocyclic moiety", and "heterocyclic radical", are used interchangeably herein, and include groups in which a heterocyclyl ring is fused to one or more aryl, heteroaryl, or cycloaliphatic rings, such as indolinyl, 3H-indolyl, cl1romanyl, phenanthridinyl, or tetrahydroquinolinyl, where the radical or point of attachment is on the heterocyclyl ring. A heterocyclyl group can be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms. The term "partially unsaturated" is intended to encompass rings having multiple sites of unsaturation, but is not intended to include aryl or heteroaryl moieties, as herein defined.

The term "linker group" or "linker" means an organic moiety that connects two parts of a compound. Linkers typically comprise an atom such as oxygen or sulfur, a unit such as NH, CH2, C(O), C(O)NH, or a chain of atoms, such as an alkylene chain. The molecular mass of a linker is typically in the range of about 14 to 200, preferably in the range of 14 to 96 with a length of up to about six atoms. In some embodiments, the linker is a $C_{1\_6}$ alkylene chain which is optionally substituted.

The term "alkylene" refers to a bivalent alkyl group. An "alkylene chain" is a polymethylene group, i.e., —$(CH_4)_n$—, wherein n is a positive integer, preferably from one to six, from one to four, from one to three, from one to two, or from two to three. A substituted alkylene chain is a polymethylene group in which one or more methylene hydrogen atoms is replaced with a substituent. Suitable substituents include those described below for a substituted aliphatic group. An alkylene chain also can be substituted at one or more positions with an aliphatic group or a substituted aliphatic group.

An alkylene chain also can be optionally interrupted by a functional group. An alkylene chain is "interrupted" by a functional group when an internal methylene unit is replaced with the functional group. Examples of suitable "interrupting functional groups" include —C(R*)=C(R*)—, —C≡C—, —O—, —S—S, —S(O)—, —S(O)$_2$—, —S(O)$_2$N(R$^+$), —N(R*)—, —N(R$^+$)CO—, N(R$^+$)CO$_2$—, —N(R$^+$)C(O)N(R$^+$)—, —C(O)N(R$^+$)—, —C(O)—, —C(O)—C(O)—, —CO$_2$—, —OCC(O)—, —OC(O)N(R$^+$)—, or N(R$^+$)S(O)$_2$. Each R$^+$, independently, is hydrogen or an optionally substituted aliphatic, aryl, heteroaryl, or heterocyclyl group, or two R$^+$ on the same nitrogen atom, taken together with the nitrogen atom, form a five to eight membered aromatic or non-aromatic ring having, in addition to the nitrogen atom, zero to two ring heteroatoms selected from N, O, and S. Each R* independently is hydrogen or an optionally substituted aliphatic, aryl, heteroaryl, or heterocyclyl group.

One of ordinary skill in the art will recognize that when an alkylene chain having an interruption is attached to a functional group, certain combinations are not sufficiently stable for pharmaceutical use. Only stable or chemically feasible compounds are within the scope of the present invention. A stable or chemically feasible compound is one in which the chemical structure is not substantially altered when kept at a temperature from about −80° C. to about +40° C., preferably from about −20° C. to about +40° C., in the absence of moisture or other chemically reactive conditions, for at least a week, or a compound which maintains its integrity long enough to be useful for therapeutic or prophylactic administration to a patient.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

The phrase "one or more substituents", as used herein, refers to a number of substituents that equals from one to the maximum number of substituents possible based on the number of available bonding sites, provided that the above conditions of stability and chemical feasibility are met. Unless otherwise indicated, an optionally substituted group can have a substituent at each substitutable position of the group, and the substituents can be either the same or different. As used herein, the term "independently selected" means that the same or different values can be selected for multiple instances of a given variable in a single compound.

Unless otherwise stated, structures depicted herein are meant to include compounds which differ only in the presence of one or more isotopically emiched atoms. For example, compounds having the present structure except for the replacement of a hydrogen atom by a deuterium or tritium, or the replacement of a carbon atom by a 13C- or 14C-enriched carbon are within the scope of the invention.

It also will be apparent to one skilled in the art that certain compounds of this invention can exist in tautomeric forms, all such tautomeric forms of the compounds being within the scope of the invention. Unless stereochemical configuration is expressly defined, structures depicted herein are meant to include all stereochemical forms of the structure; i.e., the R and S configurations for each asymmetric center. Therefore, unless otherwise indicated, single stereochemical isomers as well as enantiomeric and diastereomeric mixtures of the present compounds are within the scope of the invention. By way of example, the compounds of formula (I) wherein R$^a$ is hydroxy can have R or S configuration at the carbon atom bearing R$^a$. Both the R and the S stereochemical isomers, as well as all mixtures thereof, are included within the scope of the invention.

Where stereochemical configuration at a given asymmetric center is defined by structure, unless stated otherwise, the depicted configuration indicates stereochemistry relative to other asymmetric centers in the molecule. Where stereochemical configuration is defined by chemical name, the designations (rel), (R*), and (S*) indicate relative stereochemistry, while the designations (+), (−), (R), (S), and (abs) indicate absolute stereochemistry.

In the compounds of formula (I), where relative stereochemistry is defined, the diastereomeric purity of the compound preferably is at least 80%, more preferably at least 90%, still more preferably at least 95%, and most preferably at least 99%. As used herein, the term. "diastereomeric purity" refers to the amount of a compound having the depicted relative stereochemistry, expressed as a percentage of the total amount of all diastereomers present.

In some embodiments, stereochemical configurations depicted at asterisked positions indicate absolute as well as relative stereochemistry. Preferably, the enantiomeric purity of the compound is at least 80%, more preferably at least 90%, still more preferably at least 95%, and most preferably at least 99%. As used herein, the term "enantiomeric purity" refers to the amount of a compound having the depicted absolute stereochemistry, expressed as a percentage of the total amount of the depicted compound and its enantiomer.

Methods for determining diastereomeric and enantiomeric purity are well-known in the art. Diastereomeric purity can be determined by any analytical method capable of quantitatively distinguishing between a compound and its diastereomers. Examples of suitable analytical methods include, without limitation, nuclear magnetic resonance spectroscopy (NMR), gas chromatography (GC), and high performance liquid chromatography (HPLC). Similarly, enantiomeric purity can be determined by any analytical method capable of quantitatively distinguishing between a compound and its enantiomer. Examples of suitable analytical methods include, without limitation, GC or HPLC, using a chiral column packing material. Enantiomers can also be distinguishable by NMR if first derivatized with an optically enriched derivatizing agent, e.g., Mosher's acid.

In some embodiments, a S1PR1 modulator agent is SEW278, or derivatives or analogues thereof SEW278 is also known as 5-[4-phenyl-5-(trifluoromethyl)-2-thienyl]-3-[3-(trifluoromethyl)phenyl]-1,2,4-oxadiazole, and has the following structure (Compound V):

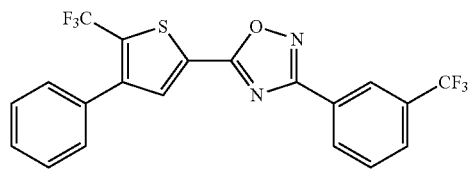 [SMILES: FC(F)(F)c1cccc(-c2noc(-c3cc(-c4ccccc4)c(C(F)(F)F)s3)n2)c1]

SEW278 is commercially available, e.g., from Cayman Chemical Company (Ann Arbor, Mich.) (Cayman Chemical Item Number 10006440)). SEW2871 is a selective S1P receptor agonist that is an immunosuppressant that does not induce bradycardia.

Derivatives, as used herein, include a chemically modified compound wherein the modification is considered routine by the ordinary skilled chemist, such as additional chemical moieties (e.g., an ester or an amide of an acid, protecting groups, such as a benzyl group for an alcohol or thiol, and tert-butoxycarbonyl group for an amine). Derivatives also include a radioactively labeled S1PR1 modulator agent, conjugates of a S1PR1 modulator agent (e.g., biotin or avidin, with enzymes such as horseradish peroxidase and the like, with bioluminescent agents, chemoluminescent agents or fluorescent agents). Additionally, moieties may be added to a S1PR1 modulator agent or a portion thereof to increase half-life in vivo. Derivatives, as used herein, also encompasses analogs, such as a compound that comprises a chemically modified form of a specific compound or class thereof, and that maintains the pharmaceutical and/or pharmacological activities characteristic of said compound or class, are also encompassed in the present invention. Derivatives, as used herein also encompasses prodrugs of a S1PR1 modulator agent, which are known to enhance numerous desirable qualities of pharmaceuticals (e.g., solubility, bioavailability, manufacturing, etc.).

Pharmaceutical Compositions

The combination of a CXCR4 antagonist and at least one S1PR1 modulator agent in either (i) a specific ratio effective to increase HSC mobilization or (ii) a specific ratio effective to increase HSC engraftment as disclosed herein can be contained in pharmaceutically acceptable formulations. Such a pharmaceutically acceptable formulation may include a pharmaceutically acceptable carrier(s) and/or excipient(s). As used herein, "pharmaceutically acceptable carrier" includes any and all solvents, dispersion media, coatings, antibacterial and anti fungal agents, isotonic and absorption delaying agents, and the like that are physiologically compatible. For example, the carrier can be suitable for injection into the cerebrospinal fluid. Excipients include pharmaceutically acceptable stabilizers. The present invention pertains to any pharmaceutically acceptable formulations, including synthetic or natural polymers in the form of macromolecular complexes, nanocapsules, microspheres, or beads, and lipid-based formulations including oil-in-water emulsions, micelles, mixed micelles, synthetic membrane vesicles, and resealed erythrocytes.

When the agents or compounds are delivered to a patient, they can be administered by any suitable route, including, for example, orally (e.g., in capsules, suspensions or tablets) or by parenteral administration. Parenteral administration can include, for example, intramuscular, intravenous, intraarticular, intraarterial, intrathecal, subcutaneous, or intraperitoneal administration. The agent can also be administered orally, transdermally, topically, by inhalation (e.g., intrabronchial, intranasal, oral inhalation or intranasal drops) or rectally. Administration can be local or systemic as indicated. Agents can also be delivered using viral vectors, which are well known to those skilled in the art.

Both local and systemic administration are contemplated by the invention. Desirable features of local administration include achieving effective local concentrations of the active compound as well as avoiding adverse side effects from systemic administration of the active compound. In a preferred embodiment, the antagonist is administered locally. Localized delivery techniques are described in, for example, 51 J. Biomed. Mat. Res. 96-106 (2000); 100(2) J. Control Release 211-19 (2004); 103(3) J. Control Release 541-63 (2005); 15(3) Vet. Clin. North Am. Equine Pract. 603-22 (1999); 1(1) Semin Interv. Cardiol. 17-23 (1996)

Compounds, or mixtures of compounds described herein, can be synthetic, naturally-occurring, or a combination thereof. Compounds, or mixtures of compounds described herein can comprise amino acids, nucleotides, hydrocarbons, lipids, polysaccharides, etc. Compounds, or mixtures of compounds described herein, can be formulated into pharmaceutical composition comprising a pharmaceutically acceptable carrier and other excipients as apparent to the skilled worker. Such composition can additionally contain effective amounts of other compounds, especially for the treatment of conditions, diseases, and/or disorders described herein.

Some embodiments comprise the administration of a pharmaceutically effective quantity of active agent or its pharmaceutically acceptable salts or esters, active agent analogs or their pharmaceutically acceptable salts or esters, or a combination thereof.

The compositions and preparations described preferably contain at least 0.1% of active agent. The percentage of the compositions and preparations can, of course, be varied, and can contain between about 2% and 60% of the weight of the amount administered. Preferably, the percentage of the compositions and preparations can contain between about 2, 5, 10, or 15% and 30, 35, 40, 45, 50, 55, or 60% of the weight of the amount administered. The amount of active compounds in such pharmaceutically useful compositions and preparations is such that a suitable dosage will be obtained.

The active agent can form salts, which are also within the scope of the preferred embodiments. Reference to a compound of the active agent herein is understood to include reference to salts thereof, unless otherwise indicated. The term "salt(s)", as employed herein, denotes acidic and/or basic salts formed with inorganic and/or organic acids and bases. In addition, when an active agent contains both a basic moiety, such as, but not limited to an amine or a pyridine or imidazole ring, and an acidic moiety, such as, but not limited to a carboxylic acid, zwitterions ("inner salts") can be formed and are included within the term "salt(s)" as used herein. Pharmaceutically acceptable (e.g., non-toxic, physiologically acceptable) salts are preferred, although other salts are also useful, e.g., in isolation or purification steps, which can be employed during preparation. Salts of the compounds of the active agent can be formed, for example, by reacting a compound of the active agent with an amount of acid or base, such as an equivalent amount, in a medium such as one in which the salt precipitates or in an aqueous medium followed by lyophilization.

The active agents which contain a basic moiety, such as, but not limited to an amine or a pyridine or imidazole ring, can form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The active agents which contain an acidic moiety, such as, but not limited to a carboxylic acid, can form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups can be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Prodrugs and solvates of the compounds of the preferred embodiments are also contemplated herein. The term "prodrug", as employed herein, denotes a compound which, upon administration to a subject, undergoes chemical conversion by metabolic or chemical processes to yield a compound of the active agent, and/or a salt and/or solvate thereof. Solvates of the active agent are preferably hydrates.

Active agent, and salts thereof, can exist in their tautomeric form (for example, as an amide or imino ether). All such tautomeric forms are contemplated herein as part of the preferred embodiments.

All stereoisomers of the present compounds, such as those, for example, which can exist due to asymmetric carbons on any of the substituents, including enantiomeric forms (which can exist even in the absence of asymmetric carbons) and diastereomeric forms, are contemplated and within the scope of the preferred embodiments. Individual stereoisomers of the compounds of the preferred embodiments can, for example, be substantially free of other isomers, or can be admixed, for example, as racemates or with all other or other selected, stereoisomers. The chiral centers of the preferred embodiments can have the S or R configuration as defined by the IUPAC 1974 Recommendations.

When the compounds according to the preferred embodiments are in the forms of salts, they are preferably pharmaceutically acceptable salts. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

The pharmaceutically acceptable salts can be prepared by reacting the active agent with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol, etc. Mixture of solvents can be used. Organic bases like lysine, arginine, diethanolamine, choline, guandine and their derivatives etc. can also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, fonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane, etc. Mixture of solvents can also be used.

As indicated above, a further object of the preferred embodiments relates to a pharmaceutical composition comprising at least one CXCR4 antagonist, and at least one S1PR1 modulator agent and a pharmaceutically acceptable vehicle or support.

The compounds can be formulated in various forms, including solid and liquid forms, such as tablets, gel, syrup, powder, aerosol, etc.

The compositions of the preferred embodiments can contain physiologically acceptable diluents, fillers, lubricants, excipients, solvents, binders, stabilizers, and the like. Diluents that can be used in the compositions include but are not limited to dicalcium phosphate, calcium sulphate, lactose, cellulose, kaolin, mannitol, sodium chloride, dry starch, powdered sugar and for prolonged release tablet-hydroxy propyl methyl cellulose (HPMC). The binders that can be used in the compositions include but are not limited to starch, gelatin and fillers such as sucrose, glucose, dextrose and lactose.

Natural and synthetic gums that can be used in the compositions include but are not limited to sodium alginate, ghatti gum, carboxymethyl cellulose, methyl cellulose, polyvinyl pyrrolidone and veegum. Excipients that can be used in the compositions include but are not limited to microcrystalline cellulose, calcium sulfate, dicalcium phosphate, starch, magnesium stearate, lactose, and sucrose. Stabilizers that can be used include but are not limited to polysaccharides such as acacia, agar, alginic acid, guar gum and tragacanth, amphotsics such as gelatin and synthetic and semi-synthetic polymers such as carbomer resins, cellulose ethers and carboxymethyl chitin.

Solvents that can be used include but are not limited to Ringers solution, water, distilled water, dimethyl sulfoxide to 50% in water, propylene glycol (neat or in water), phosphate buffered saline, balanced salt solution, glycol and other conventional fluids.

The dosages and dosage regimen in which the compounds are administered will vary according to the dosage form, mode of administration, the condition being treated and particulars of the patient being treated. Accordingly, optimal therapeutic concentrations will be best determined at the time and place through routine experimentation.

The compounds in some embodiments can also be used enterally. Orally, the compounds according to the preferred embodiments are suitable administered at the rate of 100 µg to 100 mg per day per kg of body weight. Preferably, orally, the compounds according to the preferred embodiments are suitable administered at the rate of about 100, 150, 200, 250, 300, 350, 400, 450, or 500 µg to about 1, 5, 10, 25, 50, 75, 100 mg per day per kg of body weight. The required dose can be administered in one or more portions. For oral administration, suitable forms are, for example, tablets, gel, aerosols, pills, dragees, syrups, suspensions, emulsions, solutions, powders and granules; a preferred method of administration consists in using a suitable form containing from 1 mg to about 500 mg of active substance. Preferably, a method of administration consists in using a suitable form containing from about 1, 2, 5, 10, 25, or 50 mg to about 100, 200, 300, 400, 500 mg of active substance.

The compounds according to the preferred embodiments can also be administered parenterally in the form of solutions or suspensions for intravenous or intramuscular perfusions or injections. In that case, the compounds according to the preferred embodiments are generally administered at the rate of about 10 µg to 10 mg per day per kg of body weight; a preferred method of administration consists of using solutions or suspensions containing approximately from 0.01 mg to 1 mg of active substance per ml. Preferably, the compounds according to the preferred embodiments are generally administered at the rate of about 10, 20, 30, 40, 50, 60, 70, 80, 90, or 100 µg to 1, 2, 3, 4, 5, 6, 7, 8, 9, or 10 mg per day per kg of body weight; a preferred method of administration consists of using solutions or suspensions containing approximately from 0.01, 0.02, 0.03, 0.04, or 0.5 mg to 0.1, 0.2, 0.3, 0.4, 0.5, 0.6, 0.7, 0.8, 0.9, or 1 mg of active substance per ml.

The compounds can be used in a substantially similar manner to other known anti-tumor agents for treating (both chemopreventively and therapeutically) various tumors. For the compounds of the preferred embodiments, the anti-tumor dose to be administered, whether a single dose, multiple dose, or a daily dose, will of course vary with the particular compound employed because of the varying potency of the compound, the chosen route of administration, the size of the recipient, the type of tumor, and the nature of the patient's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. For example, an oncologist skilled in the art of cancer treatment will be able to ascertain, without undue experimentation, appropriate protocols for the effective administration of the compounds of the preferred embodiments related to cancer therapy, such as by referring to the earlier published studies on compounds found to have anti-tumor properties.

The active compounds and/or pharmaceutical compositions of the embodiments disclosed herein can be administered according to various routes, typically by injection, such as local or systemic injection(s). For example, intratumoral injections are preferred for treating existing cancers. However, other administration routes can be used as well, such as intramuscular, intravenous, intradermic, subcutaneous, etc. Furthermore, repeated injections can be performed, if needed, although it is believed that limited injections will be needed in view of the efficacy of the compounds.

For ex vivo administration, the active agent can be administered by any standard method that would maintain viability of the cells, such as by adding it to culture medium (appropriate for the target cells) and adding this medium directly to the cells. As is known in the art, any medium used in this method can be aqueous and non-toxic so as not to render the cells non-viable. In addition, it can contain standard nutrients for maintaining viability of cells, if desired. For in vivo administration, the complex can be added to, for example, to a pharmaceutically acceptable carrier, e.g., saline and buffered saline, and administered by any of several means known in the art. Examples of administration include parenteral administration, e.g., by intravenous injection including regional perfusion through a blood vessel supplying the tissues(s) or organ(s) having the target cell(s), or by inhalation of an aerosol, subcutaneous or intramuscular injection, topical administration such as to skin wounds and lesions, direct transfection into, e.g., bone marrow cells prepared for transplantation and subsequent transplantation into the subject, and direct transfection into an organ that is subsequently transplanted into the subject. Further administration methods include oral administration, particularly when the active agent is encapsulated, or rectal administration, particularly when the active agent is in suppository form.

It is contemplated that such target cells can be located within a subject or human patient, in which case a safe and effective amount of the active agent, in pharmacologically acceptable form, would be administered to the patient. Generally speaking, it is contemplated that useful pharmaceutical compositions of the preferred embodiments will include the selected active compound derivative in a convenient amount, e.g., from about 0.001% to about 10% (w/w) that is diluted in a pharmacologically or physiologically acceptable carrier, such as, for example, phosphate buffered saline. The route of administration and ultimate amount of material that is administered to the subject under such circumstances will depend upon the intended application and will be apparent to those of skill in the art in light of the examples which follow.

Any composition chosen should be of low or non-toxicity to the cell. Toxicity for any given compound can vary with the concentration of compound used. It is also beneficial if the compound chosen is metabolized or eliminated by the body and if this metabolism or elimination is done in a manner that will not be harmfully toxic.

The examples are illustrative of the types of compounds to be used in the method claimed herein; the list is not exhaustive. Derivatives of the above compounds that fit the criteria of the claims are preferably also be considered when choosing an active compound.

The compound is preferably administered such that a therapeutically effective concentration of the compound is in contact with the affected cells of the body. The dose administered to a subject, particularly a human, in the context of the preferred embodiments is preferably sufficient to effect a therapeutic response in the subject over a reasonable period of time. The dose will be determined by the strength of the particular compound employed and the condition of the subject, as well as the body weight of the subject to be treated. The existence, nature, and extent of any adverse side effects that might accompany the administration of a particular compound also will determine the size of the dose and the particular route of administration employed with a particular patient. In general, the compounds of the preferred embodiments are therapeutically effective at low doses. The generally useful dose range is from about 0.001 mM, or less, to about 100 mM, or more. Preferably, the effective dose range is from about 0.01, 0.05, 0.1, 0.5, 0.6, 0.7, 0.8, or 0.9 mM, to about 1, 2, 3, 4, 5, 6, 7, 8, 9, or 10 mM. Accordingly, the compounds will be generally administered in low doses. However, guideline ratios of the CXCR4 antagonists to S1PR1 modulator agents to promote HSC migration are provided in Table 1, and guidelines of the ratios of CXCR4 antagonist to S1PR1 modulator agents effective to enhance engraftment are provided in Table 2. Additionally, one can use the grid matrix array as disclosed in the Examples to determine the optimal ratio of the CXCR4 antagonist: S1PR1 modulator for the desired result, e.g., to enhance mobilization or to enhance engraftment.

In some embodiments, the composition can be administered in a pharmaceutically acceptable carrier. Pharmaceutically acceptable carriers are well-known to those who are skilled in the art. The choice of carrier will be determined in part by the particular compound, as well as by the particular method used to administer the composition. Accordingly, there is a wide variety of suitable formulations of the pharmaceutical composition of the preferred embodiments.

The compounds as disclosed herein can be administered orally, topically, parenterally, by inhalation or spray, vaginally, rectally or sublingually in dosage unit formulations. The term "administration by injection" includes but is not limited to: intravenous, intraarticular, intramuscular, subcutaneous and parenteral injections, as well as use of infusion techniques. Dermal administration can include topical application or transdermal administration. One or more compounds can be present in association with one or more non-toxic pharmaceutically acceptable carriers and if desired other active ingredients.

In some embodiments, compositions intended for oral use can be prepared according to any suitable method known to the art for the manufacture of pharmaceutical compositions. Such compositions can contain one or more agents selected from the group consisting of diluents, sweetening agents, flavoring agents, coloring agents and preserving agents in order to provide palatable preparations. Tablets contain the active ingredient in admixture with non-toxic pharmaceutically acceptable excipients that are suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets can be uncoated or they can be coated by known techniques to delay disintegration and adsorption in the gastrointestinal tract and thereby provide a sustained action over a longer period. For example, a time delay material such as glyceryl monostearate or glyceryl distearate can be employed. These compounds can also be prepared in solid, rapidly released form.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active materials in admixture with excipients suitable for the manufacture of aqueous suspensions can also be used. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, can also be present.

In some embodiments, the compounds can also be in the form of non-aqueous liquid formulations, e.g., oily suspensions which can be formulated by suspending the active ingredients in a vegetable oil, for example arachis oil, olive oil, sesame oil or peanut oil, or in a mineral oil such as liquid paraffin. The oily suspensions can contain a thickening agent, for example beeswax, hard paraffin or cetyl alcohol. Sweetening agents such as those set forth above, and flavoring agents can be added to provide palatable oral preparations. These compositions can be preserved by the addition of an anti-oxidant such as ascorbic acid.

In further embodiments, the compounds as disclosed herein can also be administrated transdermally using methods known to those skilled in the art. For example, a solution or suspension of an active agent in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of an active agent can be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents can also include mixtures of one or more materials selected from lower alcohols, lower ketones, lower carboxylic acid esters, polar ethers, lower hydrocarbons, halogenated hydrocarbons.

Suitable penetration enhancing materials for transdermal delivery system are known to those skilled in the art, and include, for example, monohydroxy or polyhydroxy alcohols such as ethanol, propylene glycol or benzyl alcohol, saturated or unsaturated C8-C18 fatty alcohols such as lauryl alcohol or cetyl alcohol, saturated or unsaturated C8-C18 fatty acids such as stearic acid, saturated or unsaturated fatty esters with up to 24 carbons such as methyl, ethyl, propyl, isopropyl, n-butyl, sec-butyl, isobutyl, tertbutyl or monoglycerin esters of acetic acid, capronic acid, lauric acid, myristinic acid, stearic acid, or palmitic acid, or diesters of saturated or unsaturated dicarboxylic acids with a total of up to about 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations can also include mixtures of one or more materials selected from monohydroxy or polyhydroxy alcohols, saturated or unsaturated C8-C18 fatty alcohols, saturated or unsaturated C8-C18 fatty acids, saturated or unsaturated fatty esters with up to 24 carbons, diesters of saturated or unsaturated discarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrenebutadiene copolymers, and natural and synthetic rubbers. Cellulose ethers, derivatized polyethylenes, and silicates can also be used as matrix components. Additional additives, such as viscous resins or oils can be added to increase the viscosity of the matrix.

Pharmaceutical compositions as disclosed herein can also be in the form of oil-in-water emulsions. The oil phase can be a vegetable oil, for example olive oil or arachis oil, or a mineral oil, for example, liquid paraffin or mixtures of these. Suitable emulsifying agents can be naturally-occurring gums, for example, gum acacia or gum tragacanth, naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions can also contain sweetening and flavoring agents. Syrups and elixirs can be formulated with sweetening agents, for example glycerol, propylene glycol, sorbitol or sucrose. Such formulations can also contain a demulcent, a preservative and flavoring and coloring agents.

In some embodiments, the compositions as disclosed herein can be formulated for administration in the form of suppositories for rectal or vaginal administration of the drug. These compositions can be prepared by mixing the drug with a suitable nonirritating excipient which is solid at ordinary temperatures but liquid at the rectal temperature or vaginal temperature and will therefore melt in the rectum or vagina to release the drug. Such materials include cocoa butter and polyethylene glycols.

For all regimens of use disclosed herein for active agent, the daily oral dosage regimen will preferably be from about 0.01 to about 200 mg/Kg of total body weight. Preferably, the daily oral dosage regimen will preferably be from about 0.01, 0.05, 0.1, 0.5, 1, 2, 3, 4, or 5 to about 10, 50, 100, 110, 120, 130, 140, 150, 160, 170, 180, 190, or 200 mg/Kg of total body weight. The daily dosage for administration by injection, including intravenous, intramuscular, subcutaneous and parenteral injections, and use of infusion techniques will preferably be from 0.01 to 200 mg/Kg of total body weight. Preferably, the daily dosage for administration by injection, including intravenous, intramuscular, subcutaneous and parenteral injections, and use of infusion techniques will preferably be from about 0.01, 0.05, 0.1, 0.5, 1, 2, 3, 4, or 5 to about 10, 50, 100, 110, 120, 130, 140, 150, 160, 170, 180, 190, or 200 mg/Kg of total body weight. The daily vaginal dosage regime will preferably be from 0.01 to 200 mg/Kg of total body weight. The daily topical dosage regimen will preferably be from 0.01 to 200 mg administered between one to four times daily. The concentration for vaginal dosage and topical dosage will preferably be that required to maintain a daily dose is of from 0.1 to 200 mg/Kg. Preferably, the daily oral dosage regimen will preferably be from about 0.01, 0.05, 0.1, 0.5, 1, 2, 3, 4, or 5 to about 10, 50, 100, 110, 120, 130, 140, 150, 160, 170, 180, 190, or 200 mg/Kg of total body weight. The daily inhalation dosage regimen will preferably be from 0.01 to 10 mg/Kg of total body weight. Preferably, the daily inhalation dosage regimen will preferably be from about 0.01, 0.05, 0.1, 0.5, to about 1, 2, 3, 4, 5, or 10, mg/Kg of total body weight.

It will be appreciated by those skilled in the art that the particular method of administration will depend on a variety of factors, all of which are considered routinely when administering therapeutics. It will also be understood, however, that the specific dose level for any given patient will depend upon a variety of factors, including, the activity of the specific compound employed, the age of the patient, the body weight of the patient, the general health of the patient, the gender of the patient, the diet of the patient, time of administration, route of administration, rate of excretion, drug combinations, and the severity of the condition undergoing therapy. It will be further appreciated by one skilled in the art that the optimal course of treatment, i.e., the mode of treatment and the daily number of doses of an active agent or a pharmaceutically acceptable salt thereof given for a defined number of days, can be ascertained by those skilled in the art using conventional treatment tests.

The active compounds can be incorporated into pharmaceutical compositions suitable for administration to a subject, e.g., a human. Such compositions typically comprise the nucleic acid molecule, protein, modulator, or antibody and a pharmaceutically acceptable carrier.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the preferred embodiments. Supplementary active compounds can also be incorporated into the compositions. A pharmaceutical composition of the preferred embodiments is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid, buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes) can also be used as pharmaceutically acceptable carriers. These can be prepared according to methods known to those skilled in the art.

It is especially advantageous to formulate oral or parenteral compositions in dosage unit form for ease of administration and uniformity of dosage. "Dosage unit form" as used herein refers to physically discrete units suited as unitary dosages for the subject to be treated, each unit containing a predetermined quantity of active compound calculated to produce the desired therapeutic effect in association with the required pharmaceutical carrier. The specification for the dosage unit forms of the preferred embodiments are dictated by and directly dependent on the unique characteristics of the active compound and the particular therapeutic effect to be achieved, and the limitations inherent in the art of compounding such an active compound for the treatment of individuals. In some embodiments, dosage unit allow different ratios of the CXCR4 antagonist with at least one S1PR1 modulator agent, thus enabling one to tailor the specific response. For example, without wishing to be bound by theory, a dosage unit can be a specific dosage unit of each agent to be used in combination with the other agent, e.g., a dose of the CXCR4 antagonist AMD3100 to be used with the S1PR1 modulator agent FTY720 can be provided. For example, a dose unit of AMD3100 can be of a particular amount such that 3 doses of the AMD3100 (e.g., 3×1 dose units) is combined with 1 dose unit of the FTY720 drug for engraftment, and 5 dose units of AMD3100 (e.g., 5×1 dose units) is combined with 1 dose unit of the FTY720 agent to promote HSC mobilization. In another exemplary example, a dose unit of AMD3100 can be of a particular amount such that 1 dose of the AMD3100 is combined with 2 dose units of the FTY720 (e.g., 2×1 dose units) for engraftment, and 2 dose units of AMD3100 (e.g., 2×1 dose units) is combined with 1 dose unit of the FTY720 agent to promote HSC mobilization.

As used herein, the term "therapeutically effective amount" means the total amount of each active component of the pharmaceutical composition or method that is sufficient to show a meaningful patient benefit. This includes both therapeutic and prophylactic treatments. Accordingly, the compounds can be used at very early stages of a disease, or before early onset, or after significant progression. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the preferred embodiments, a therapeutically effective amount of one, two, or more of the active agents of the preferred embodiments is administered to a subject afflicted with a disease or disorder related to the mobilization of hematopoietic stem cells or progenitor cells, or to a tissue which has such disease or disorder. The active agents of the preferred embodiments can be administered in accordance with the method of the preferred embodiments either alone of in combination with other known therapies. When co-administered with one or more other therapies, the active agents of the preferred embodiments can be administered either simultaneously with the other treatment(s), or sequentially. If administered sequentially, the attending physician will decide on the appropriate sequence of administering the active agents of the preferred embodiments in combination with the other therapy.

Generally, a therapeutically effective amount of active agent (i.e., an effective dosage) ranges from about 0.001 to 5000 mg/kg body weight, more preferably about 0.01 to 1000 mg/kg body weight, more preferably about 0.01 to 500 mg/kg body weight, more preferably about 0.01 to 250 mg/kg body weight, more preferably about 0.01 to 100 mg/kg body weight, more preferably about 0.001 to 60 mg/kg body weight, more preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors can influence the dosage required to effectively treat a subject, including but not limited to the severity of the disease or disorder, previous treatments, the general health and/or age of the subject, and other diseases present. Moreover, treatment of a subject with a therapeutically effective amount can include a single treatment or, preferably, can include a series of treatments. In a preferred example, a subject is treated in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage used for treatment can increase or decrease over the course of a particular treatment. Changes in dosage can result and become apparent from the results of diagnostic assays as described herein.

In some embodiments, the present invention encompass one or more additional agents in addition to a CXCR4 antagonist and at least one S1PR1 modulator agent. Such an agent can, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (I.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The pharmaceutically acceptable formulations can be suspended in aqueous vehicles and introduced through conventional hypodermic needles or using infusion pumps.

The amount of agent administered to the individual will depend on the characteristics of the individual, such as general health, age, sex, body weight and tolerance to drugs as well as the degree, severity and type of rejection. The skilled artisan will be able to determine appropriate dosages depending on these and other factors.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the preferred embodiments. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses can be determined using the assays described herein. When one or more of these small molecules is to be administered to a subject (e.g., a human) in order to modulate expression or activity of a polypeptide or nucleic acid of the preferred embodiments, a physician, veterinarian, or researcher can, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Suitable dosage ranges for the active compound can vary according to these considerations, but in general, the compounds are administered in the range of about 0.1 µg/kg-5 mg/kg of body weight; preferably the range is about 1 µg/kg-300 µg/kg of body weight; more preferably about 10 µg/kg-100 µg/kg of body weight. For a typical 70-kg human subject, thus, the dosage range is from about 0.7 µg-350 mg; preferably about 700 µg-21 mg; most preferably about 700 µg-7 mg. Dosages can be higher when the compounds are administered orally or transdermally as compared to, for example, i.v. administration. The compounds can be administered as a single bolus dose, a dose over time, as in i.v. or transdermal administration, or in multiple dosages.

The amount of active compound to be administered can vary according to the discretion of the skilled artisan. The amount of active compound to be administered to the recipient is within the ranges described above for stem cell mobilization. However, the administration of such amounts will vary according to the standards set forth by clinicians in the field of stem cell enhancement therapy. Administration should generally occur daily following chemotherapy or other treatment for 1 or more days, preferably daily or intermittently for up to 200 days.

The dosage regimen for increasing white blood cell survival following chemotherapy and mobilizing hematopoietic progenitor cells from bone marrow into peripheral blood with the active compounds is based on a variety of factors, including the type of injury, the age, weight, sex, medical condition of the individual, the severity of the condition, the route of administration, and the particular compound employed. Thus, the dosage regimen can vary widely, but can be determined routinely by a physician using standard methods. Dosage levels of the order of between 0.1 ng/kg and 10 mg/kg body weight of the active compounds per body weight are useful for all methods of use disclosed herein.

The treatment regime will also vary depending on the disease being treated, based on a variety of factors, including the type of injury, the age, weight, sex, medical condition of the individual, the severity of the condition, the route of administration, and the particular compound employed. For example, the active compounds are administered to an oncology patient for up to 30 days prior to a course of chemotherapy and for up to 60 days post-chemotherapy. The therapy is administered for 1 to 6 times per day at dosages as described above.

In a preferred embodiment, the active compound is administered subcutaneously. A suitable subcutaneous dose of the active compound is preferably between about 0.1 ng/kg and about 10 mg/kg administered twice daily for a time sufficient to increase mobilization of hematopoietic stem and progenitor cells from bone marrow into peripheral blood. This dosage regimen maximizes the therapeutic benefits of the treatments while minimizing the amount of agonist needed. Such an application minimizes costs as well as possible deleterious side effects.

For subcutaneous administration, the active ingredient can comprise from 0.0001% to 10% w/w, e.g. from 1% to 2% by weight of the formulation, although it can comprise as much as 10% w/w, but preferably not more than 5% w/w, and more preferably from 0.1% to 1% of the formulation. In a most preferred embodiment, subcutaneous administration of between about 1 to 1000 mg/kg/day of the active compounds is initiated at between one week before to one week after administration of a cancer therapy (e.g., a chemotherapeutic agent).

In another preferred embodiment, a subject undergoes repeated cycles of treatment according to the method disclosed herein. Preferably, a subsequent treatment cycle commences only after the administration of the compounds disclosed herein have been terminated and the subject's blood cell counts (e.g., white blood cell count) have returned to a therapeutically acceptable level (as determined by the attending veterinarian or physician), permitting the repeated chemotherapy.

In all of these embodiments, the compounds can be administered prior to, simultaneously with, or subsequent to chemotherapeutic exposure or any other therapeutic exposure.

The active compounds can be administered by any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intraarterial, intramuscular, intrasternal, intratendinous, intraspinal, intracranial, intrathoracic, infusion techniques or intraperitoneally.

The active compounds can be made up in a solid form (including granules, powders or suppositories) or in a liquid form (e.g., solutions, suspensions, or emulsions). The compounds can be applied in a variety of solutions. Suitable solutions for use in accordance with the preferred embodiments are sterile, dissolve sufficient amounts of the peptide, and are not harmful for the proposed application. In this regard, the compounds disclosed herein are very stable but are hydrolyzed by strong acids and bases. The compounds are soluble in organic solvents and in aqueous solutions at pH 5-8.

The active compounds can be subjected to conventional pharmaceutical operations such as sterilization and/or can contain conventional adjuvants, such as preservatives, stabilizers, wetting agents, emulsifiers, buffers etc.

For administration, the active compounds are ordinarily combined with one or more adjuvants appropriate for the indicated route of administration. The compounds can be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds disclosed herein can be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent can include time delay material, such as glyceryl monostearate or glyceryl distearate alone or with a wax, or other materials well known in the art.

Screens to Identify Optimal Ratios of CXCR4 Antagonist with at Least One S1PR1 Modulator Agent for HSC Mobilization or Engraftment.

The combination of a CXCR4 antagonist and at least one S1PR1 modulator agent in either (i) a specific ratio effective to increase HSC mobilization or (ii) a specific ratio effective to increase HSC engraftment as disclosed herein can be identified in a variety of ways, such as the zebrafish genetic system as disclosed herein in the Examples. The zebrafish is an excellent genetic system for the study of vertebrate development and diseases. See e.g., Hsia & Zon, 33(9) Exp. Hematol. 1007-14 (2005); de Jong & Zon; 39 Ann Rev. Genet. 481-501 (2005); Paffett-Lugassy & Zon, 105 Meth. Mol. Med. 171-98 (2005); Haffner & Nusslein-Volhard, 40 Int'l J. Devel. Biol. 221-27 (1996). The embryo developing externally is transparent and organs can be easily visualized. Zebrafish and mammals share many of the same gene programs in development. When zebrafish mate, they give rise to large numbers (100-200 weekly) of transparent embryos. Many embryos can be placed in a relatively small space, and there is a short generation time (about 3 months). Large-scale screens have generated more than 2000 genetic mutants with specific defects that affect virtually every aspect of embryogenesis. Driever et al., 123 Devel. 37-46 (1996); Eisen, 87 Cell 969-77 (1996). Many of the blood mutants have been useful in describing key events in hematopoeisis. Dooley & Zon, 10 Curr. Op. Genet. Devel. 252-56 (2000). Zebrafish have been used to perform whole organism-based small molecule screens because large numbers of the embryos can be arrayed into microtiter plates containing compounds from a chemical library. For example, Peterson and colleagues tested 1,100 compounds for developmental defects. Peterson et al., 97 P.N.A.S. USA 12965-69 (2000). From this screen, about 2% of the compounds were lethal, and 1% caused a specific phenotype. For example, one compound suppressed formation of inner ear structures called otoliths, but caused no other defects.

It is also possible to screen for chemical suppressors of mutant phenotypes. Peterson et al., 22 Nat. Biotech. 595-99 (2004); Stern et al., 1 Nat. Chem. Biol. 366-70 (2005). In one such screen, chemicals were found to rescue the gridlock mutant, a model of congenital coarctation of the aorta. Peterson et al., 2004. The mechanism of this rescue involved the induction of VEGF which corrected the angiogenesis defect. These data demonstrate that highly potent and specific compounds can be identified using zebrafish.

Further regarding zebrafish, a high-density genetic map has been constructed that includes microsatellite markers, genes, and expressed sequence tags (ESTs). Knapuk et al., 18 Nat. Genet. 338-43 (1998); Shimoda et al., 58 Genomic 219-32 (1999); Kelly et al., 10 Genome Res. 558-67 (2000); Woods et al., 20 Genome Res. 1903-14 (2000). A full-length cDNA project has also been undertaken as an extension to the zebrafish EST project. A dense RH map has been constructed and integrated with data for the genome sequencing project at the Sanger Center. An important web resource supported by the NIH is the zebrafish information network (ZFIN), a focal point for the community A stock center and supportive laboratory called the Zebrafish International Resource Center (ZIRC) also greatly helps the field. The Sanger Center is sequencing the zebrafish genome which may be completed in 2007.

The onset of definitive hematopoiesis has been studied in a number of vertebrate species. In seminal work in the avian species, chick-quail chimeras demonstrated that definitive hematopoietic stem cells do not arise on the yolk sac, but arise within the embryo proper. Dieterien-Lievre 33 J. Embryol. Exp. Morphol. 607-19 (1975). Similar studies in the Xenopus embryo using diploid/triploid chimeras elucidated that the ventral blood island (the yolk sac equivalent) played a minor role in adult hematopoiesis compared to the dorsal lateral plate. Kau & Turpen 131 J. Immunol. 2262-66 (1983). Based on the finding that the dorsolateral plate mesoderm contained putative hematopoietic cells that gave rise to definitive hematopoiesis, several groups further investigated the developing aorta gonad mesonephros (AGM) region. Medvinsky et al., 364 Nature 64-67 (1993); Godin et al., 364 Nature 67-70 (1993). Within this region, there are clusters of cells in the ventral wall of the aorta that were originally recognized in the pig. Sabin, 9 Contrib. to Embryol. 213-62 (1920). Others have suggested that these clusters represent early hematopoietic stem cells that are derived from "hemogenic" endothelial cells.

The process of AGM hematopoiesis is evolutionarily conserved in the vertebrate. Galloway & Zon, 53 Curr. Topics Dev. Biol. 139-58 (2003). In mouse, the onset of stem cells occurs at 8.5 days to 9 days, just as circulation is beginning. Hematopoietic stem cells of the AGM region at day eleven can be transplanted, however, the cells at day ten will not lead to long term engraftment. Further studies have elucidated that the aorta is polarized, and factors from the ventral and dorsal regions will modify the behavior of cells. For instance, the dorsal region of the aorta is derived from somitic mesoderm. It is under the influence of TGF$\alpha$, BMP, and sonic hedgehog signaling. Parnanud & Dieterlen-Lievre, 126 Devel. 617-27 (1999).

Cell marking studies have demonstrated that the putative HSC in the AGM have the potential to invade the subaortic mesenchyme and also a variety of tissues. Jaffredo et al., 125 Devel. 4575-83 (1998); Jaffredo et al., 224 Devel. Biol. 204-14 (2000). These cell marking studies used India ink or cells infected by retroviruses tagged with LacZ infused into the vasculature. These fate mapping experiments showed labeling of hematopoietic cells within tissues. These studies elucidate the onset of hematopoietic stem cells within the aorta in the vertebrate embryo Several genes have been found to be required for AGM hematopoiesis. The gene, runx1 (previously AML1 oncoprotein), is expressed in the aortic wall in the ventral region where the hematopoietic cells are found; this gene function is required for AGM hematopoiesis. Cal et al., 13 Immunity 423-31 (2000). The runx1 mutant mouse lacks an AGM and has defective hematopoiesis. The defect in the runx1 mutant can be rescued by a runx1 transgene driven by the Tie2 promoter, demonstrating that endothelial and hematopoietic driven expression of runx1 is sufficient to regulate AGM hematopoiesis. Miller et al., 32 Nature Genet. 645-49 (2002). In a runx1 knock-in, there are subaortic mesenchymal cells that are labeled with LacZ, and this observation has been interpreted to mean that some of the subaortic cells may give rise to hematopoietic stem cells. North et al., 126 Devel. 2563-75 (1999). Recent studies, have demonstrated that the subaortic endothelial cells push through the endothelial layer and form hematopoietic clusters. Bertrand et al., 102 P.N.A.S. USA 134-39 (2005); Tavian & Peault, 33 Exp. Hemat. 1062-69 (2005); Tavian & Peault, 49 Int'l J. Devel. Biol. 243-50 (2005); Tavian et al., 1044 Ann NY Acad. Sci. 41-50 (2005).

Thus, it may be disputed whether the hemogenic endothelial cells or the subaortic mesodermal cells are the true precursors of HSCs. Once the hematopoietic stem cells bud off the endothelial wall, they are CD45+ and express the transcription factors runx1 and c-myb. The AGM cells are also under control by notch signaling. The notch1 knock-out mouse AGM hematopoietic stem cells and runx1 and c-myb expression are absent in the aorta region. Kumano et al., 18 Immunity 699-711 (2003); Robert-Moreno et al., 132 Devel. 1117-26 (2005). In addition, the coupTF transcription factor also lacks AGM hematopoietic stem cells, although it has not been studied as thoroughly. You et al., 435 Nature 98-104 (2005). Although runx1, cymb, notch, and coup appear to be important for AGM hematopoiesis, the interaction, temporal and spatial relation of these factors, and role of other potentially unknown factors is not known. A better understanding of the genetic program of the onset of hematopoiesis is clearly necessary.

Figure 15A:
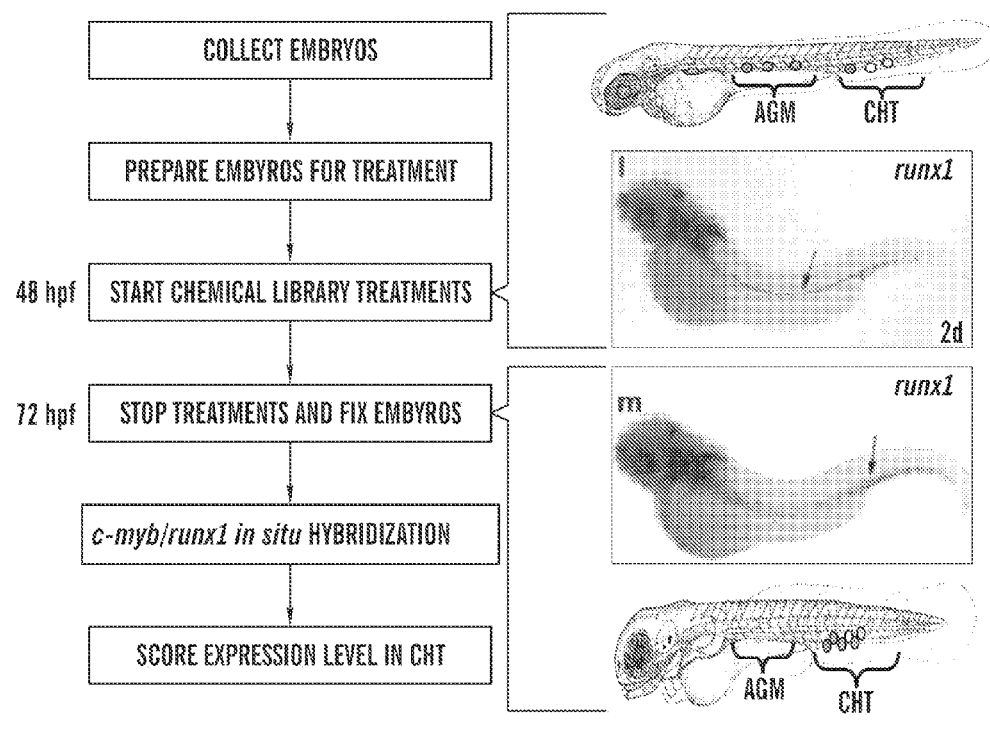
FIG. 15A-15B are schematics of the chemical screen to identify the pathways that direct homing to the CHT.
Figure 15B:
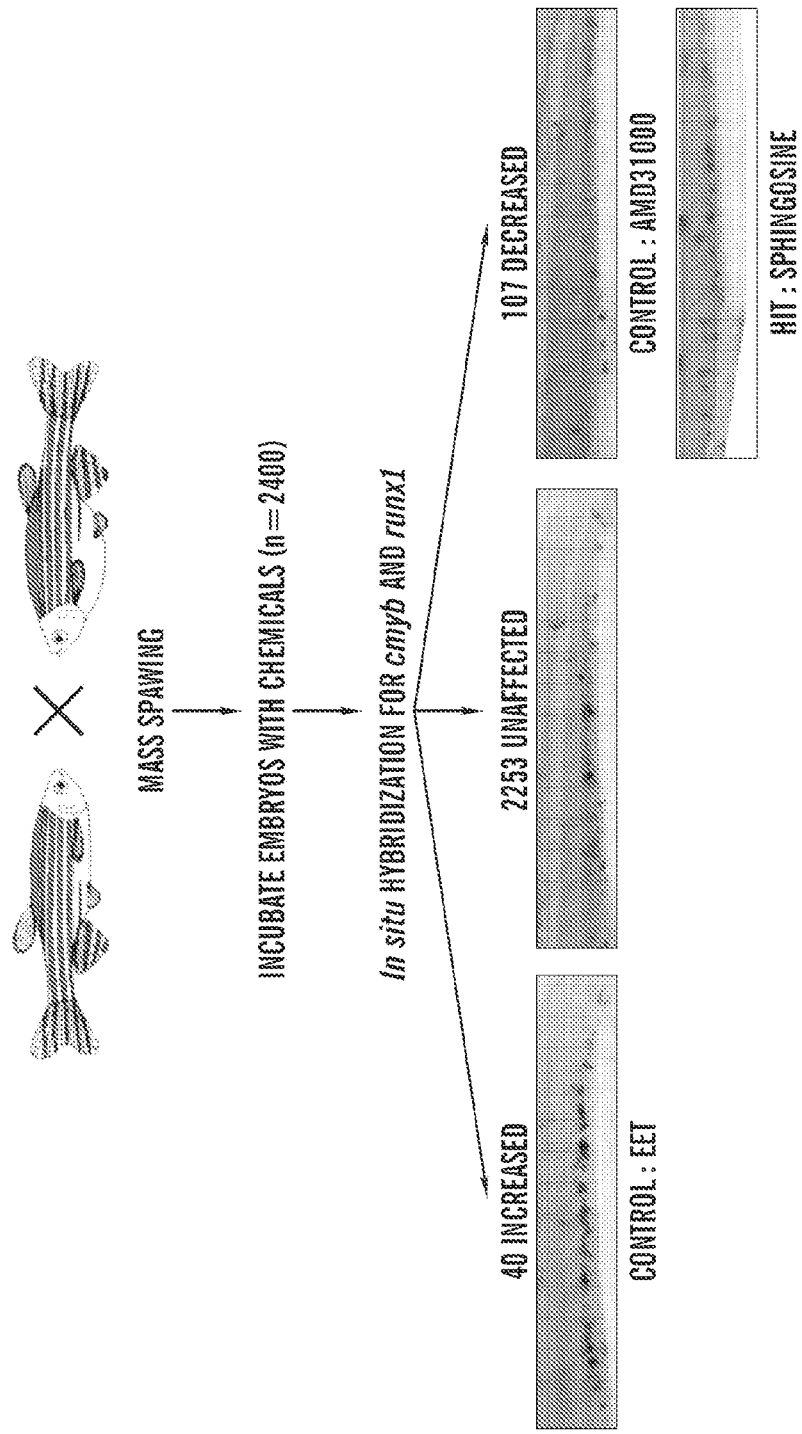
Figure 16A:
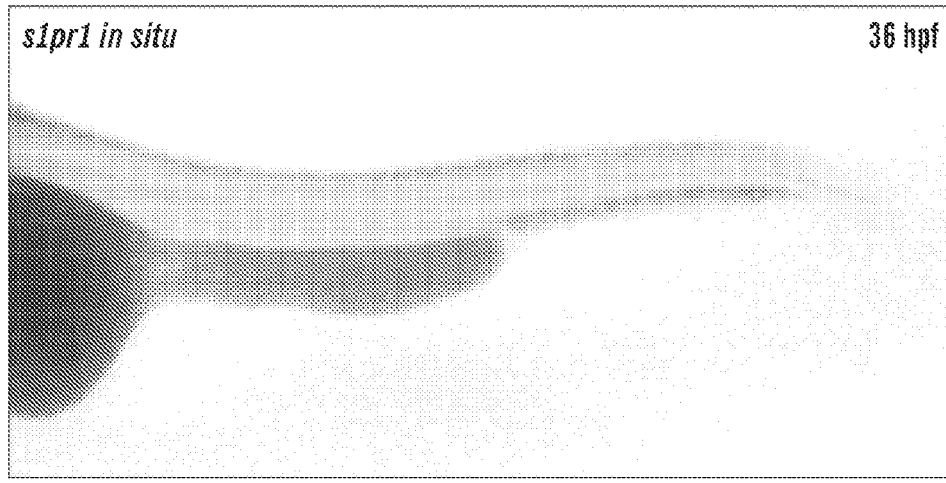
FIG. 16A-16B show expression of spingosine receptor S1PR1 in AGM and CHT.
Figure 16B:
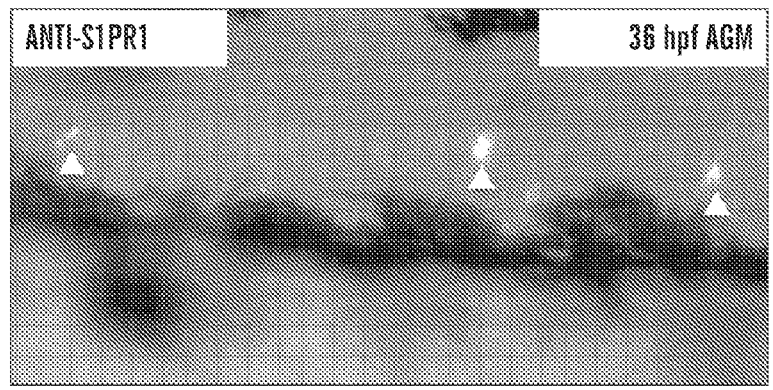
Figure 17A:
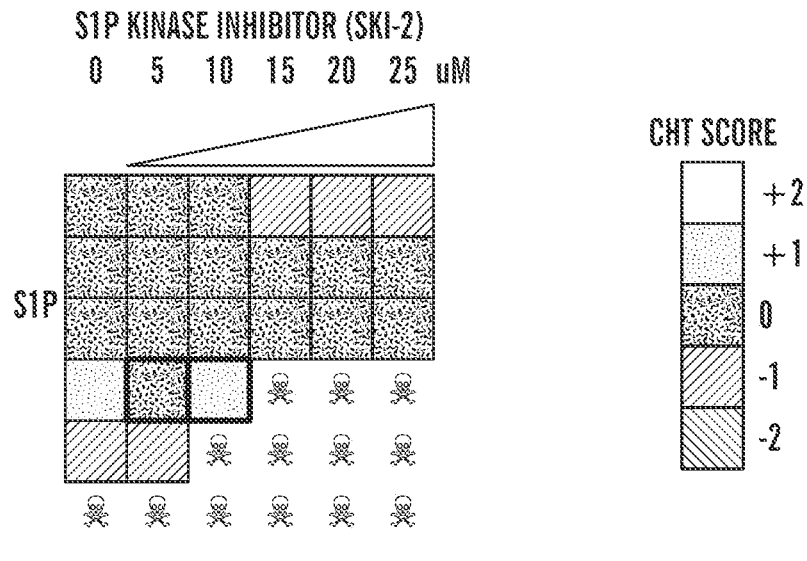
FIG. 17A-17C shows endogenous S1P and S1PR1 are required for CHT engraftment.
Figure 17B:
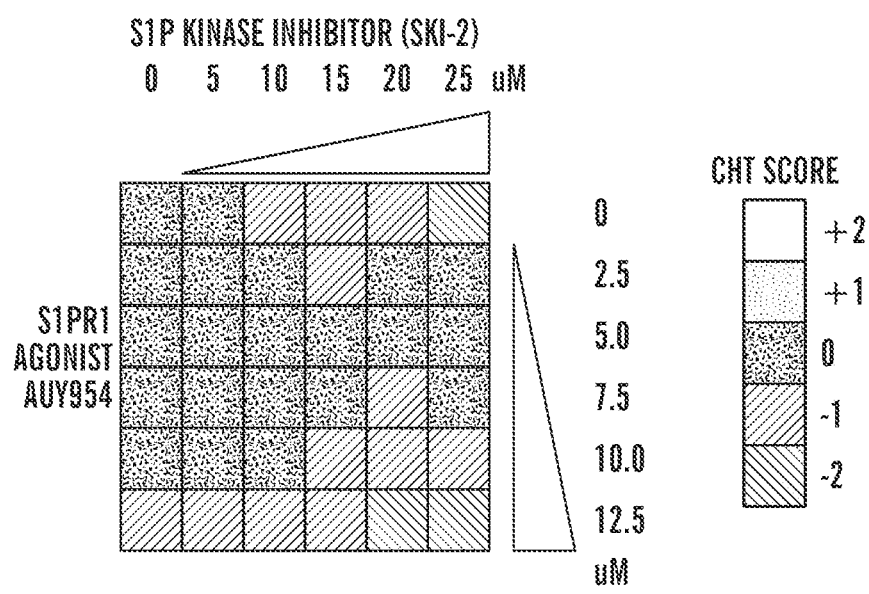
Figure 17C:
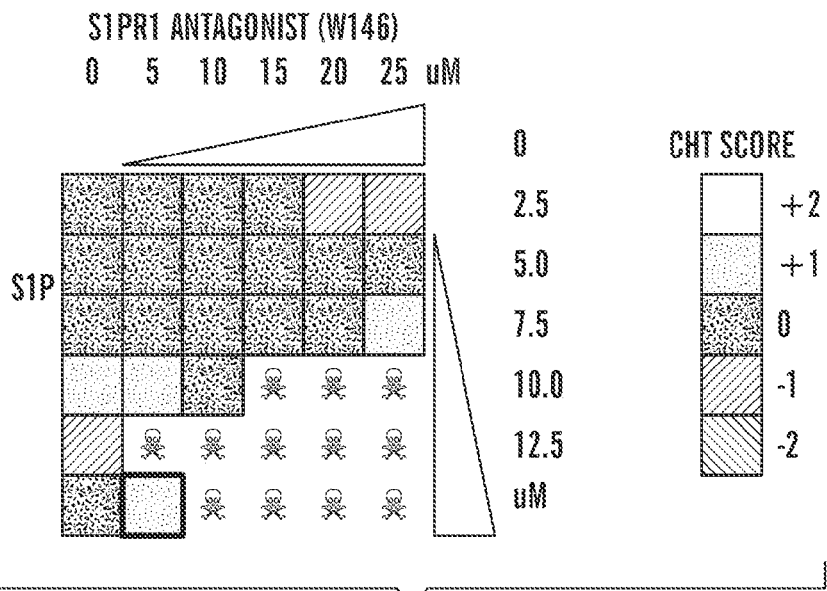
Figure 18:
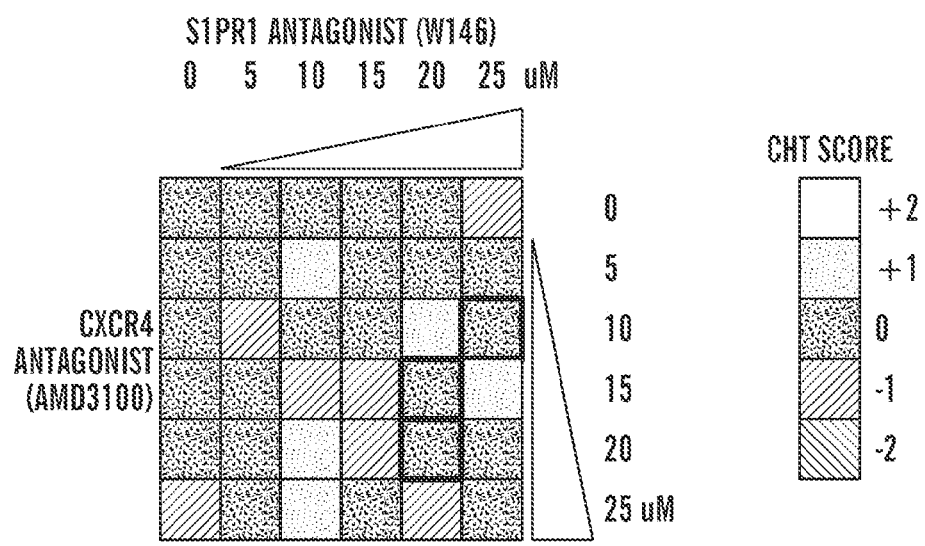
FIG. 18 shows S1PR1 antagonist chemically interacts with CXCR4 antagonist. S1P or S1PR1 agonist internalizes active S1PR1, while S1PR1 antagonist stabilizes inactive S1PR1 that recycles to surface.
Figure 19C:
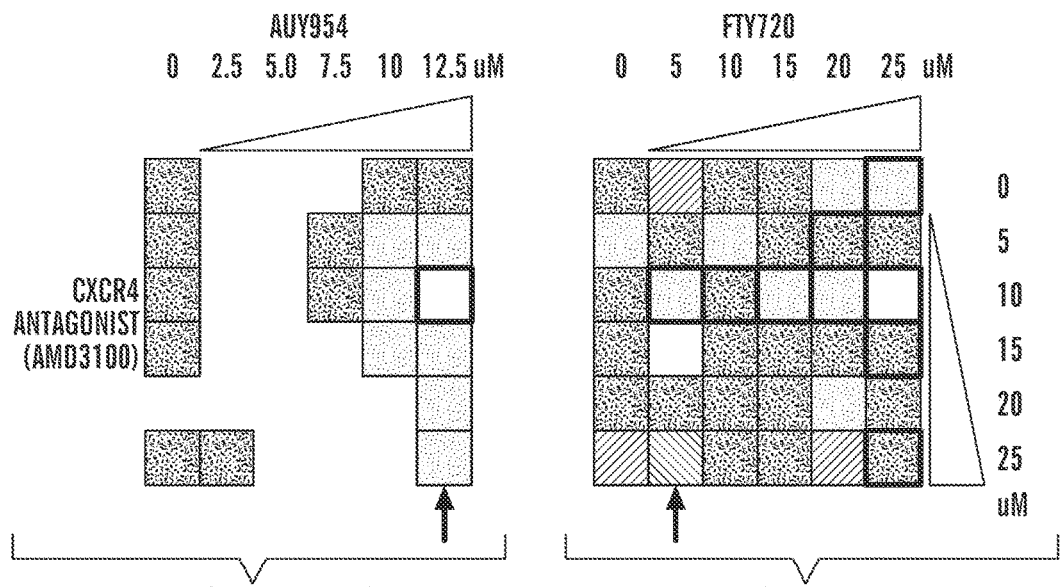
FIG. 19C shows effect of increasing dose of CXCR4 antagonist with increasing dose of SEQ2871 on HSC engraftment, showing greatest engraftment with a +2 CHT score with 10 µM AMD3100 and 10 µM SEW2871 (as shown by the arrow). The sphingosine-1-phosphate receptor agonist FTY720 supports a CXCR4-dependent migration and bone marrow homing of CD34+ progenitor cells.
Figure 19C:
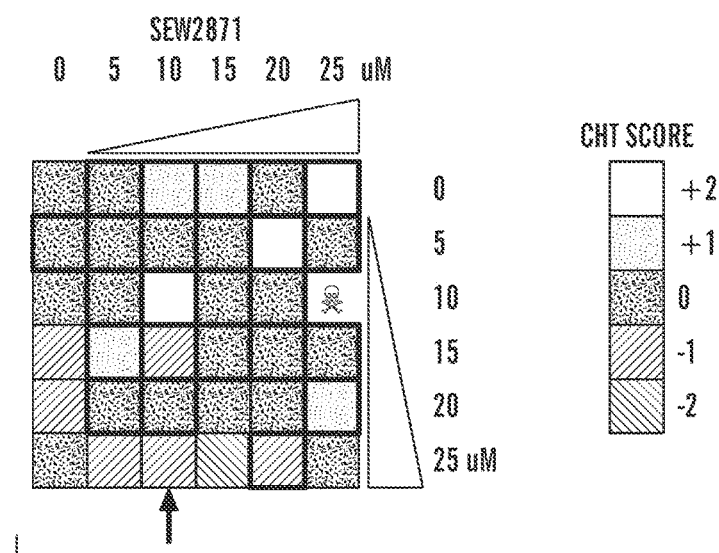
Figure 20:
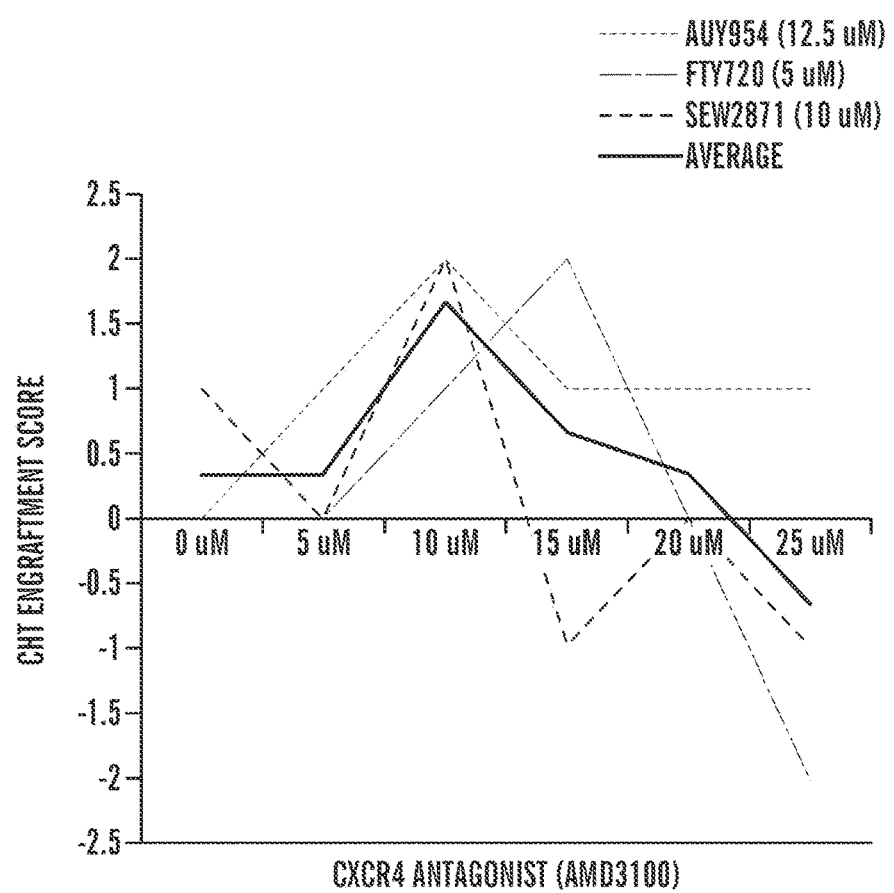
FIG. 20 shows S1PR1 agonists chemically interact with CXCR4 antagonist AMD3100.
Figure 21:
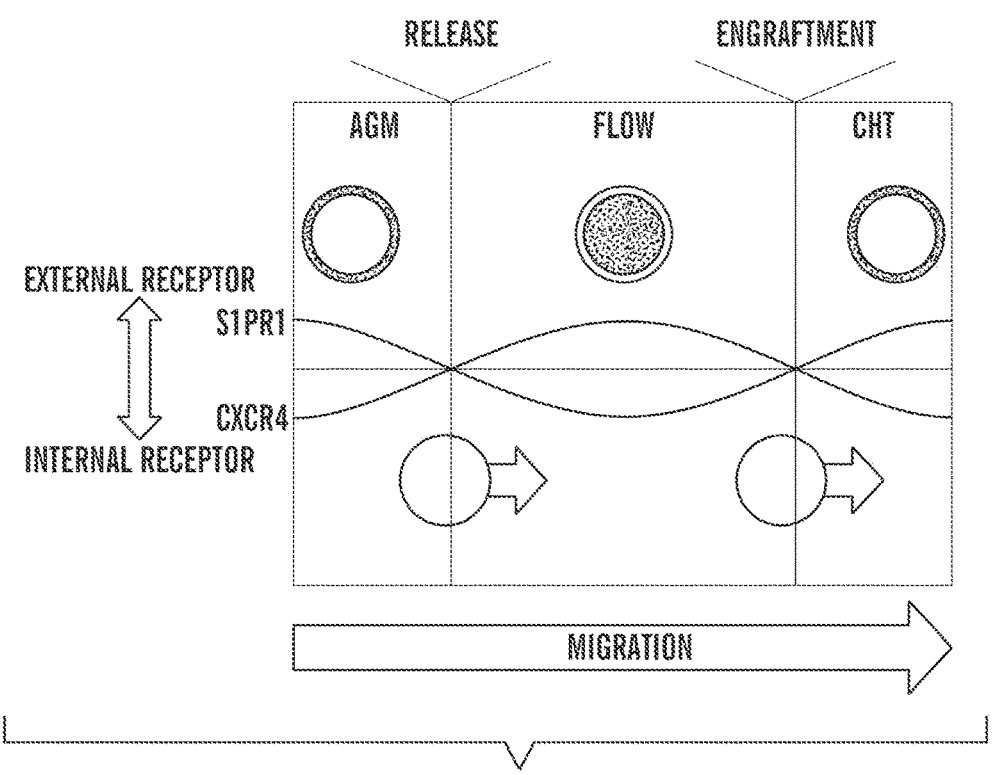
FIG. 21 is a schematic showing the dynamic localization of S1PR1 (blue) and CXCR4 (red) receptors. Before release of HSC, S1PR1 is externally localized and CXCR4 is internally located. After release during HSC flow and migration to the CHT, CXCR4 is externally localized and S1PR1 is internal. After engraftment of HSC, S1PR1 is externally localized and CXCR4 is internally located.
Figure 22:
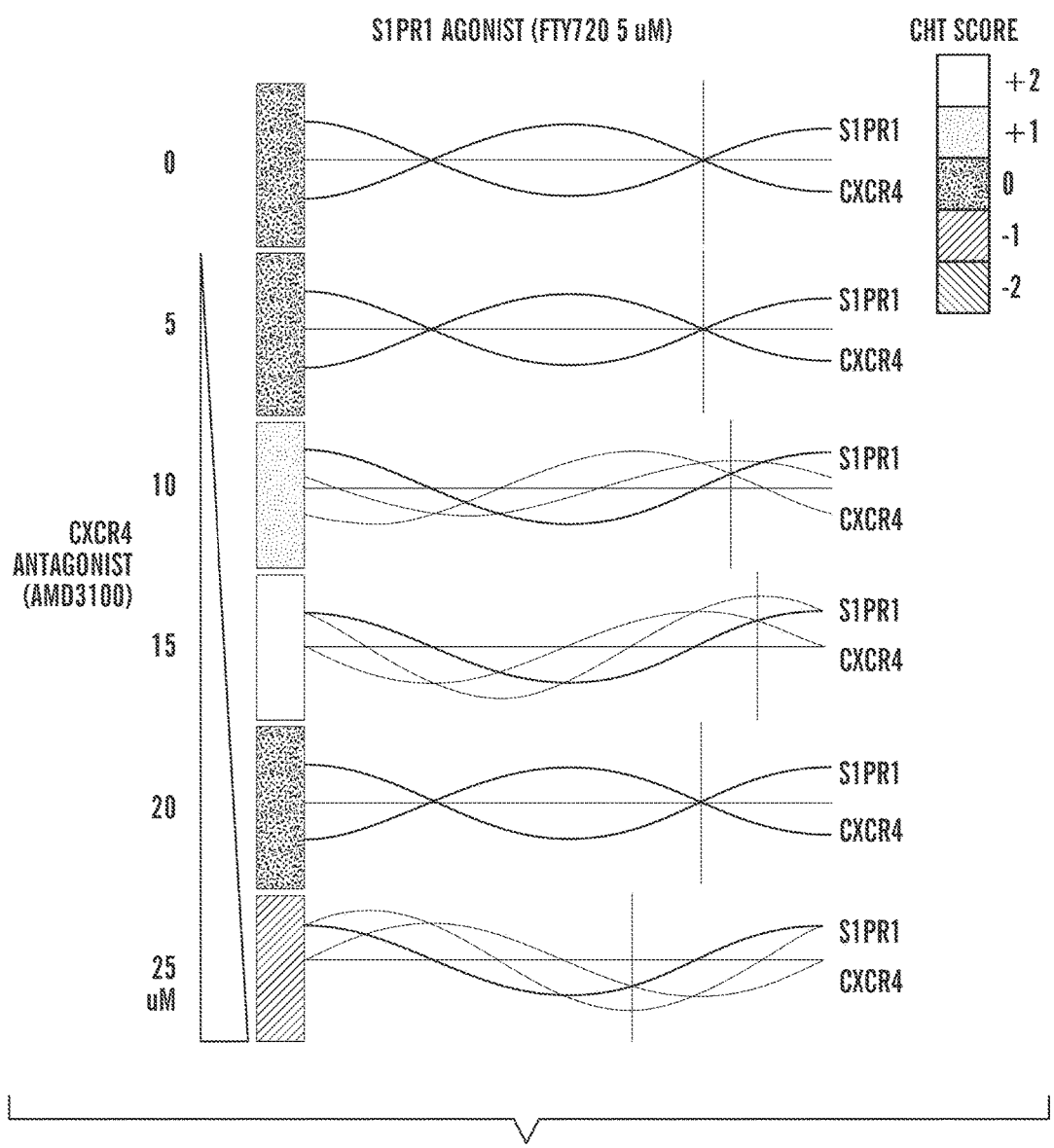
FIG. 22 shows the modulating effective levels of S1PR1 agonist FTY720 (5 µM) in the presence of CXCR4 antagonists AMD3100 at increasing concentrations.
Figure 23:
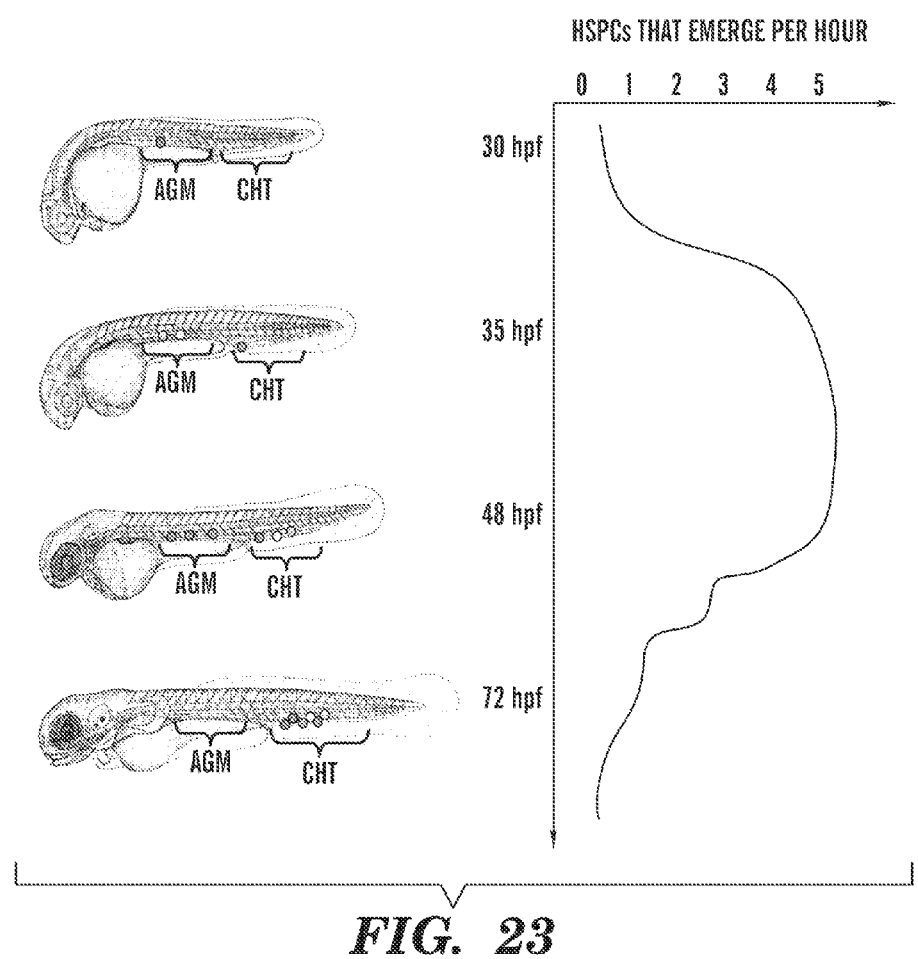
FIG. 23 shows a schematic of the emergence of definitive HSCs. The first definitive HSPCs emerge from the hemogenic endothelium of the DA at about 30 hpf. The number of stem cells produced increases until a peak at about 48 hours when still only about 5 cells per hour emerge from the aorta. Gradually, the number of stem cells produced tapers off During this period of stem cell production, cells are released into the circulation find their way to and colonize their next niche: the CHT.

A chemical genetic screen was conducted to identify novel pathways that increase HSC mobilization and engraftment during zebrafish embryogenesis. FIGS. 15A and 15B shows an embodiment of the assay used.

The study of hematopoiesis in zebrafish has previously focused on the first wave of hematopoiesis, termed primitive, and the derivation of definitive hematopoietic stem cells in the aorta, gonads and mesonephros (AGM) region of the zebrafish embryo. Little is known about the production of AGM stem cells in vertebrates, but both runx1 and notch1 have been shown to be required for AGM HSC formation.

Approaches to characterizing the signaling pathways involved in definitive hematopoietic stem cell derivation during embryogenesis, using the zebrafish as a model, include evaluating the hypothesis that prostaglandins regulate AGM stem cell production using mutants, morphants, transgenics and chemicals and examining the role of the wnt pathway in the formation of AGM HSCs and investigate potential interactions with other signaling pathways known to be active in the AGM region. Zebrafish genetics may be used to define new pathways involved in AGM HSC formation during embryogenesis and allow for large-scale mutagenesis screens for defects in definitive hematopoiesis in zebrafish. This allows for the isolation and characterization of some of the mutated genes responsible for normal AGM HSC production.

Work has also explored the zebrafish AGM stem cell production and the notch pathway. The AGM is thought to form from lateral mesoderm present during early somitogenesis. The tissue expresses flk1. As it migrates, it begins to express an artery specific marker called gridlock. Later, by eighteen somites, the cells express tie1 and tie2, and continue to migrate medially and form a solid cord. The cord becomes hollow and turns into the aorta. At thirty hours the runx1 transcription factor is initially expressed ventrally. Shortly after, the c-myb positive hematopoietic cells are found in the ventral wall of the aorta. The dorsal part of the aorta expresses a T box transcription factor, called tbx20. The process in zebrafish seems very similar to that of other vertebrates including humans, mice, chickens and frogs. Galloway & Zon, 53 Curr. Topics Devel. Biol. 139-58 (2002).

The role of runx1 in the development of the AGM was also examined. Similar to the mouse knockout, a knockdown of runx1 in zebrafish led to a decreased number of cells in the AGM that are expressing c-myb. Overexpression of runx1 led to an expansion of stem cell number in the aorta, and ectopic expression of c-myb n the vein. Primitive hematopoiesis proceeds normally in the runx1 morphant. This provides evidence of a requirement of runx1 for AGM formation, and additionally establishes runx1 as a factor that is sufficient for generating definitive stem cells. Evaluation of the role of the notch pathway in AGM formation revealed that runx1 acted downstream or parallel to notch signaling.

Kits

One aspect of the present invention relates to kits useful in the methods as disclosed herein. In a further aspect, kits are provided for increasing mobilization of hematopoietic stem and progenitor cells from bone marrow into peripheral blood, wherein the kits comprise an effective amount of the CXCR4 antagonist, e.g., AMD3100 and an effective amount of at least one S1PR1 modulator agent for increasing mobilization of hematopoietic progenitor cells from bone marrow into peripheral blood, and instructions for using the amount of the CXCR4 antagonist, e.g., AMD3100 and S1PR1 modulator agent as a therapeutic.

Another aspect of the present invention provides a kit for increasing engraftment of hematopoietic stem and progenitor cells from the peripheral blood to the bone marrow, wherein the kits comprise an effective amount of the CXCR4 antagonist, e.g., AMD3100 and an effective amount of at least one S1PR1 modulator agent for increasing engraftment of hematopoietic progenitor cells from the peripheral blood to the bone marrow in a subject, and instructions for using the amount of the CXCR4 antagonist, e.g., AMD3100 and S1PR1 modulator agent as a therapeutic.

In a preferred embodiment, the kit further comprises a pharmaceutically acceptable carrier, such as those adjuvants described above. In another preferred embodiment, the kit further comprises a means for delivery of the active compound to a subject. Such devices include, but are not limited to syringes, material or micellar solutions, bandages, wound dressings, aerosol sprays, lipid foams, transdermal patches, topical administrative agents, polyethylene glycol polymers, carboxymethyl cellulose preparations, crystalloid preparations (e.g., saline, Ringer's lactate solution, phosphate-buffered saline, etc.), viscoelastics, polyethylene glycols, and polypropylene glycols. The means for delivery can either contain the effective amount of the active compounds, or can be separate from the compounds, that are then applied to the means for delivery at the time of use.

The kits comprising the compositions and preparations described herein, e.g., at least one CXCR4 antagonist, e.g., AMD3100 and at least one S1PR1 modulator agent can contain at least 0.1% of each active compound. The percentage of the compositions and preparations can, of course, be varied, and can contain between about 2% and 60% of the weight of the amount administered. The amount of active compounds in such pharmaceutically useful compositions and preparations is such that a suitable dosage will be obtained.

One embodiment also pertains to kits useful in the methods. Such a kit contains an appropriate quantity of active compound, and other components useful for the methods.

For example, a kit used to facilitate in vivo expansion of hematopoietic stem cells contains an appropriate amount of the active compound to facilitate mobilization, as well as an amount of the active compound to enhance the expansion of the stem cells by growth factors. Such a kit can also contain an appropriate amount of a growth factor.

A further embodiment of the present invention relates to kits comprising a CXCR4 antagonist and at least one S1PR1 antagonist as disclosed herein in a ratio effective to increase HSC mobilization, and/or at ratios effective to increase HSC engraftment.

The methods, kits, and pharmaceutical compositions of the present invention, by increasing white blood cell survival following chemotherapy and mobilizing hematopoietic progenitor cells from bone marrow into peripheral blood, significantly enhance the utility of presently available treatments for clinical chemotherapeutic treatments.

The following references, to the extent that they provide exemplary procedural or other details supplementary to those set forth herein, are specifically incorporated herein by reference in their entirety where permitted: U.S. Pat. Nos. 6,410,323; 6,191,147; 6,184,203; 5,863,532; 5,574,025; 5,470,832; 5,244,916; 5,043,268, 60/527,589 (Methods of Enhancing Stem Cell Engraftment), filed Dec. 5, 2003; 61/069,073 (Mobilization of Hematopoietic Stem Cells), filed Mar. 12, 2008; U.S. patent application publications 2005/0142103, filed Aug. 12, 2004; 2005/0069553, filed Mar. 31, 2005; 2005/0238666, filed Dec. 3, 2004; 2006/0004032, filed Nov. 19, 2004; 2007/0155766, filed Jul. 21, 2006; and 2006/0135532, filed Nov. 18, 2005.

Some Embodiments of the Present Invention May be Defined in any of the Following Numbered Paragraphs:

1. A method comprising administering to a subject in need of hematopoietic stem cell (HSC) engraftment a CXCR4 antagonist and (R)-3-Amino-4-(3-hexylphenylamino)-4-oxobutylphosphonic acid (W146), wherein the ratio of the concentration of the CXCR4 antagonist to the concentration of the W146 compound is (0.5-0.6):1.0.
2. The method of paragraph 1, wherein the CXCR4 antagonist is 1,1'-[1,4-Phenylenebis(methylene)]bis[1,4,8,11-tetraazacyclotetradecane] (AMD3100).
3. The method of any of paragraphs 1-2, wherein the AMD3100 is at a concentration of between 2-10 µM and the concentration of W146 is between of 4-20 µM.
4. The method of any of paragraphs 1-3, wherein the AMD3100 is at a concentration of 5 µM and the concentration of W146 is 10 µM.
5. The method of any of paragraphs 1-4, wherein AMD3100 is at a concentration of between 0.4 mg/kg to 2 mg/kg.
6. The method any of paragraphs 1-5, wherein AMD3100 is at a concentration of 1 mg/kg and the concentration of W146 is 2 mg/kg.
7. The method of any of paragraphs 1-6, wherein the CXCR4 antagonist is administered at substantially the same time as the W146, or before or after the administration of W146.
8. The method of any of paragraphs 1-7, wherein the subject is administered a population of HSCs prior to, during or after administration of the CXCR4 antagonist and W146.
9. The method of any of paragraphs 1-8, wherein the population of HSCs is obtained from peripheral blood, cord blood, bone marrow, amniotic fluid, or placental blood.
10. A method comprising administering to a subject in need of hematopoietic stem cell (HSC) engraftment a CXCR4 antagonist and 3-[[2-[4-phenyl-3-(trifluoromethyl)phenyl]-1-benzothiophen-5-yl]methylamino]propanoic acid (AUY954), wherein the ratio of the concentration of the CXCR4 antagonist to the concentration of the AUY954 compound is (0.4-2.5):1.0.
11. The method of paragraph 10, wherein the CXCR4 antagonist is 1,1'-[1,4-Phenylenebis(methylene)]bis[1,4,8,11-tetraazacyclotetradecane] (AMD3100).
12. The method of any of paragraphs 10-11, wherein the AMD3100 is at a concentration of between 5-20 µM and the concentration of AUY954 is between of 5-25 µM.
13. The method of any of paragraphs 10-12, wherein the AMD3100 is at a concentration of 10 µM and the concentration of AUY954 is 12.5 µM.
14. The method of any of paragraphs 10-13, wherein the AMD3100 is at a concentration of between 1 mg/kg to 4 mg/kg and the concentration of AUY954 is between 1.25 mg/kg and 5 mg/kg.
15. The method of any of paragraphs 10-14, wherein the AMD3100 is at a concentration of 1 mg/kg and the concentration of AUY954 is 2.5 mg/kg.
16. The method of any of paragraphs 10-15, wherein the CXCR4 antagonist is administered at substantially the same time as the AUY954, or before or after the administration of AUY954.
17. The method of any of paragraphs 10-16, wherein the subject is administered a population of HSCs prior to, during or after administration of the CXCR4 antagonist and AUY954.
18. The method of any of paragraphs 10-17, wherein the population of HSCs is obtained from peripheral blood, cord blood, bone marrow, amniotic fluid, or placental blood.
19. A method comprising administering to a subject in need of hematopoietic stem cell (HSC) engraftment a CXCR4 antagonist and 2-amino-2-[2-(4-octylphenyl)ethyl]propane-1,3-diol (FTY720), wherein the ratio of the concentration of the CXCR4 antagonist to the concentration of the 2-amino-2-[2-(4-octylphenyl)ethyl]propane-1,3-diol compound is (0.4-3.0):1.0.
20. The method of paragraph 19, wherein the CXCR4 antagonist is 1,1'-[1,4-Phenylenebis(methylene)]bis[1,4,8,11-tetraazacyclotetradecane] (AMD3100).
21. The method of any of paragraphs 19-20, wherein the concentration of AMD3100 is between 10-25 µM and the concentration of FTY720 is between of 2-10 µM.
22. The method of any of paragraphs 19-22, wherein the AMD3100 is at a concentration of 15 µM and the concentration of FTY720 is 5 µM.
23. The method of any of paragraphs 19-23, wherein the AMD3100 is at a concentration of between 1.5 mg/kg to 5 mg/kg and the concentration of FTY720 is between 0.4 mg/kg and 2 mg/kg.
24. The method of any of paragraphs 19-23, wherein the AMD3100 is at a concentration of 3 mg/kg and the concentration of FTY720 is 1 mg/kg.
25. The method of any of paragraphs 19-24, wherein the CXCR4 antagonist is administered at substantially the same time as the FTY720, or before or after the administration of FTY720.

26. The method of any of paragraphs 19-25, wherein the subject is administered a population of HSCs prior to, during or after administration of the CXCR4 antagonist and FTY720.

27. The method of any of paragraphs 19-26, wherein the population of HSCs is obtained from peripheral blood, cord blood, bone marrow, amniotic fluid, or placental blood.

28. A method comprising administering to a subject in need of hematopoietic stem cell (HSC) engraftment a CXCR4 antagonist and 5-[4-phenyl-5-(trifluoromethyl)-2-thienyl]-3-[3-(trifluoromethyl)phenyl]-1,2,4-oxadiazole (SEW2871), wherein the ratio of the concentration of the CXCR4 antagonist to the concentration of the 5-[4-phenyl-5-(trifluoromethyl)-2-thienyl]-3-[3-(trifluoromethyl)phenyl]-1,2,4-oxadiazole compound is (0.25-1.0):1.0.

29. The method of paragraph 28, wherein the CXCR4 antagonist is 1,1'-[1,4-Phenylenebis(methylene)]bis[1,4,8,11-tetraazacyclotetradecane] (AMD3100).

30. The method of any of paragraphs 28-29, wherein the AMD3100 or SEW2871 is at a concentration of between 5-20 μM.

31. The method of any of paragraphs 28-30, wherein the AMD3100 is at a concentration of 10 μM and the SEW2871 is at a concentration of 10 μM.

32. The method of any of paragraphs 28-31, wherein the AMD3100 and SEW2871 is at a concentration of between 1 mg/kg to 4 mg/kg.

33. The method of any of paragraphs 28-32, wherein the AMD3100 is at a concentration of 2 mg/kg and the concentration of SEW2871 is 2 mg/kg.

34. The method of any of paragraphs 28-33, wherein the CXCR4 antagonist is administered at substantially the same time as the SEW2871, or before or after the administration of SEW2871.

35. The method of any of paragraphs 28-34, wherein the subject is administered a population of HSCs prior to, during or after administration of the CXCR4 antagonist and SEW2871.

36. The method of any of paragraphs 28-35, wherein the population of HSCs is obtained from peripheral blood, cord blood, bone marrow, amniotic fluid, or placental blood.

37. The method of any of paragraphs 1 to 36, wherein the CXCR4 antagonist T-140.

38. The method of any of paragraphs 1 to 37, wherein the population of cells is cryopreserved.

39. The method of any of paragraphs 1 to 38, wherein the subject is a candidate for bone marrow or stem cell transplantation, or a subject that has received bone marrow ablating chemotherapy or irradiation therapy.

40. A method comprising administering to a subject in need of hematopoietic stem cell (HSC) mobilization a CXCR4 antagonist and (R)-3-Amino-4-(3-hexylphenylamino)-4-oxobutylphosphonic acid (W146), wherein the ratio of the concentration of the CXCR4 antagonist to the concentration of the W146 compound is (1.25-2.0):1.

41. The method of paragraph 40, wherein the CXCR4 antagonist is 1,1'-[1,4-Phenylenebis(methylene)]bis[1,4,8,11-tetraazacyclotetradecane] (AMD3100).

42. The method of any of paragraphs 40-41, wherein the AMD3100 is at a concentration of between 5-20 μM and the concentration of W146 is between of 2-10 μM.

43. The method of any of paragraphs 40-42, wherein the AMD3100 is at a concentration of 10 μM and the concentration of W146 is 5 μM.

44. The method of any of paragraphs 40-43, wherein the AMD3100 is at a concentration of between 1 mg/kg to 4 mg/kg and the concentration of W146 is between 0.4 mg/kg and 2 mg/kg.

45. The method of any of paragraphs 40-44, wherein the AMD3100 is at a concentration of 2 mg/kg and the concentration of W146 is 1 mg/kg.

46. The method of any of paragraphs 40-45, wherein the CXCR4 antagonist is administered at substantially the same time as the W146, or before or after the administration of W146.

47. The method of any of paragraphs 40-46, wherein a population of HSCs are obtained from the subject during or after administration of the CXCR4 antagonist and W146.

48. The method of any of paragraphs 40-47, wherein the population of HSCs is obtained from peripheral blood, cord blood, bone marrow, amniotic fluid, or placental blood.

49. A method comprising administering to a subject in need of hematopoietic stem cell (HSC) mobilization a CXCR4 antagonist and 2-amino-2-[2-(4-octylphenyl)ethyl]propane-1,3-diol (FTY720), wherein the ratio of the concentration of the CXCR4 antagonist to the concentration of the 2-amino-2-[2-(4-octylphenyl)ethyl]propane-1,3-diol compound is 5:1.

50. The method of paragraph 49, wherein the CXCR4 antagonist is 1,1'-[1,4-Phenylenebis(methylene)]bis[1,4,8,11-tetraazacyclotetradecane] (AMD3100).

51. The method of any of paragraphs 49-50, wherein the AMD3100 is at a concentration of between 10-50 μM and the concentration of FTY720 is between of 2-10 μM.

52. The method of any of paragraphs 49-51, wherein the AMD3100 is at a concentration of 25 μM and the concentration of FTY720 is 5 μM.

53. The method of any of paragraphs 49-52, wherein the AMD3100 is at a concentration of between 2 mg/kg to 10 mg/kg and the concentration of FTY720 is between 0.4 mg/kg and 2 mg/kg.

54. The method of any of paragraphs 49-53, wherein the AMD3100 is at a concentration of 5 mg/kg and the concentration of FTY720 is 1 mg/kg.

55. The method of any of paragraphs 49-54, wherein the CXCR4 antagonist is administered at substantially the same time as the FTY720, or before or after the administration of FTY720.

56. The method of any of paragraphs 49-55, wherein a population of HSCs are obtained from the subject during or after administration of the CXCR4 antagonist and FTY720.

57. The method of any of paragraphs 49-56, wherein the population of HSCs is obtained from peripheral blood, cord blood, bone marrow, amniotic fluid, or placental blood 58. A method comprising administering to a subject in need of hematopoietic stem cell (HSC) mobilization a CXCR4 antagonist and 5-[4-phenyl-5-(trifluoromethyl)-2-thienyl]-3-[3-(trifluoromethyl)phenyl]-1,2,4-oxadiazole (SEW2871), wherein the ratio of the concentration of the CXCR4 antagonist to the concentration of the 5-[4-phenyl-5-(trifluoromethyl)-2-thienyl]-3-[3-(trifluoromethyl)phenyl]-1,2,4-oxadiazole compound is (1.25-5.0):1.0.

59. The method of paragraph 58, wherein the CXCR4 antagonist is 1,1'-[1,4-Phenylenebis(methylene)]bis[1,4,8,11-tetraazacyclotetradecane] (AMD3100).
60. The method of any of paragraphs 48-59, wherein the AMD3100 is at a concentration of between 10-50 µM and the concentration of SEW2871 is between 6-30 µM
61. The method of any of paragraphs 48-60, wherein the AMD3100 is at a concentration of 25 µM and the concentration of SEW2871 is 15 µM.
62. The method of any of paragraphs 48-61, wherein the AMD3100 is at a concentration of between 2 mg/kg and 10 mg/kg SEW2871 is between 1.2 mg/kg and 6 mg/kg.
63. The method of any of paragraphs 48-62, wherein the AMD3100 is at a concentration of 5 mg/kg and the concentration of SEW2871 is 3 mg/kg.
64. The method of any of paragraphs 48-63, wherein the CXCR4 antagonist is administered at substantially the same time as the SEW2871, or before or after the administration of SEW2871.
65. The method of any of paragraphs 48-64, wherein a population of HSCs are obtained from the subject during or after administration of the CXCR4 antagonist and SEW2871.
66. The method of any of paragraphs 48-65, wherein the population of HSCs is obtained from peripheral blood, cord blood, bone marrow, amniotic fluid, or placental blood.
67. The method of any of paragraphs 40 to 66, wherein the CXCR4 antagonist T-140.
68. The method of any of paragraphs 40 to 67, wherein the population of HSCs obtained from the subject are cryopreserved.
69. The method of any of paragraphs 40-68, wherein the population of HSCs obtained from the subject are administered to a subject in a bone marrow or stem cell transplantation.
70. The method of any of paragraphs 40 to 68, wherein the subject is a bone marrow donor.
71. A pharmaceutical composition comprising at least one CXCR4 antagonist and W146 in an effective amount to promote HSC engraftment in a subject.
72. A pharmaceutical composition comprising at least one CXCR4 antagonist and AUY in an effective amount to promote HSC engraftment in a subject.
73. A pharmaceutical composition comprising at least one CXCR4 antagonist and FTY720 in an effective amount to promote HSC engraftment in a subject.
74. A pharmaceutical composition comprising at least one CXCR4 antagonist and SEW2781 in an effective amount to promote HSC engraftment in a subject.
75. A pharmaceutical composition comprising at least one CXCR4 antagonist and W146 in an effective amount to promote HSC migration in a subject.
76. A pharmaceutical composition comprising at least one CXCR4 antagonist and FTY720 in an effective amount to promote HSC migration in a subject.
77. A pharmaceutical composition comprising at least one CXCR4 antagonist and SEW2871 in an effective amount to promote HSC migration in a subject.
78. A kit comprising at least one CXCR4 antagonist and W146 in an effective amount to promote HSC engraftment in a subject.
79. A kit comprising at least one CXCR4 antagonist and AUY in an effective amount to promote HSC engraftment in a subject.
80. A kit comprising at least one CXCR4 antagonist and FTY720 in an effective amount to promote HSC engraftment in a subject.
81. A kit comprising at least one CXCR4 antagonist and SEW2781 in an effective amount to promote HSC engraftment in a subject.
82. A kit comprising at least one CXCR4 antagonist and W146 in an effective amount to promote HSC migration in a subject.
83. A kit comprising at least one CXCR4 antagonist and FTY720 in an effective amount to promote HSC migration in a subject.
84. A kit comprising at least one CXCR4 antagonist and SEW2871 in an effective amount to promote HSC migration in a subject.

In addition, information regarding procedural or other details supplementary to those set forth herein, are described in cited references specifically incorporated herein by reference.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Similarly, the various features and steps discussed above, as well as other known equivalents for each such feature or step, can be mixed and matched by one of ordinary skill in this art to perform methods in accordance with principles described herein.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein, but instead by reference to claims attached hereto.

Several embodiments will now be described further by non-limiting examples.

EXAMPLES

The examples presented herein relate to the methods of promoting HSC mobilization using optimal ratios of CXCR4 antagonists and at least one S1PR1 modulator agent. Examples presented herein also relate to methods of using optimal ratios of a CXCR4 antagonist and at least one S1PR1 modulator agent to promote HSC engraftment. Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

Methods and Materials.

Transgenic zebrafish embryos were intercrossed and selected using epifluorescence (e.g. Runx1+23:EGFP, cmyb:EGFP[4], cd41:EGFP[2], kdrl:DsRed2[31]). Live imaging was performed using a spinning disk confocal microscope with an incubated chamber. Zebrafish embryos were mounted and imaged as previously described. Live mouse fetal liver explants were prepared as previously described for aorta-gonad-mesonephros tissue[10]. Image processing was done primarily with Fluorender[32] and ImageJ, which included the MTrackJ plugin[33] for manual cell tracking. For chemical screening and dose matrices, stage-matched AB embryos were dechorionated and arrayed 8-10/well in 96-well mesh-bottomed plates (Millipore). Embryos were treated from 48-72 hpf by placement directly in 96-well receiver plates containing small molecules diluted in E3 media+1% DMSO. Embryos were checked for circulation before fixation. Whole mount in situ hybridization was performed as previously described[34], with the addition of 0.2% glutaraldehyde to 4% formaldehyde at the post-fixation step. Morpholino (s1pr1/edg1 ATG-MO[23] obtained from Gene Tools, LLC) was injected into one-cell Tu or cmyb:EGFP; kdrl:DsRed2 transgenic embryos at a 1 ng dose (higher doses stop circulation). Lineage tracing was performed by injecting cd41:EGFP positive embryos with caged fluorescein conjugated to dextran (MW 10000). Embryos were uncaged in the DA at 28 hpf with a UV laser. Embryos were raised to 46 hpf in E3 media or E3+S1PR1 antagonist W146 (10 µM), then fixed for antibody staining to detect double positive cd41:EGFP and uncaged FITC HSPCs. Receptor fusion cDNAs (25 pg) were injected into one-cell embryos with Tol2 RNA (15 pg). Flow cytometry was performed using a LSR II and cells were sorted using a FACSAria (BD Biosciences). Flow cytometry data was analyzed using FACSDiva and FlowJo software.

Animal husbandry. Zebrafish and mice were maintained in accordance with Animal Research Guidelines at Children's Hospital Boston.

Vectors and transgenesis. All PCR was performed using the High Fidelity Advantage 2 PCR Kit (Clontech). The Runx1+23 enhancer[1] was PCR amplified from C57/BL6 mouse genomic DNA using the following primers: Forward (underlined XhoI and BamHI sites added) 5'-GG CTCGAGGGATCCGGGGTGGGAGGTGTAAGTTC-3' (SEQ ID NO: 3); 5'-GGGGTGGGAGGTGTAAGTTC-3' (SEQ ID NO: 4) and Reverse (underlined BglII and NotI sites added) 5'-GG GCGGCCGCAGATCTCAGGTGTCAGCAACCCATC-3' (SEQ ID NO: 5). The PCR fragment was gel purified, XhoI/BglII digested, ligated into XhoI/BamHI digested Tol2kit[37] #228 p5E-MCS vector and sequence verified. The mouse 13-globin minimal promoter was PCR amplified from C57/BL6 mouse genomic DNA using the following primers: Forward (underlined SpeI site added) 5'-GG ACTAGTCCAATCTGCTCAGAGAGGACA-3' (SEQ ID NO: 6) and Reverse (underlined SacII site added) 5'-GG CCGCGGGATGTCTGTTTCTGAGGTTGC-3' (SEQ ID NO: 7). The 13-globin minimal promoter and Runx1+23 5' entry vector were SpeI/SacII digested and ligated together. Multisite Gateway reactions were performed according to the Invitrogen protocol. The Runx1+23 5' entry enhancer/minimal promoter construct was assembled with middle entry vectors Tol2kit #383 pME-EGFP or Tol2kit #233 pME-NLS-mCherry, 3' entry vector Tol2kit #302 p3E-polyA, and destination vector Tol2kit #394 pDestTol2pA2. Transgenic lines were established as previously described[38]. At least two independent lines with 50% transmission from the F2 generation were established for each construct (Runx1+23:EGFP and Runx1+23:NLS-mCherry).

S1PR1-mCherry fusion constructs were created as follows. A full-length cDNA clone of human S1PR1 was used as PCR template. S1PR1 was amplified using the following primers: Forward 5'-ATGGGGCCCACCAGCGTCCC-3' (SEQ ID NO: 8) and Reverse (without stop codon) 5'-GGAAGAAGAGTTGACGTTTCCAGAAGA-CATAATGGTCTCTGG-3' (SEQ ID NO: 9). The PCR product was directly cloned into pENTR/D-TOPO (Invitrogen) and sequence verified. The multisite gateway clone was assembled using: 1) 5' entry clone Runx1+23 enhancer/minimal promoter; 2) middle entry clone S1PR1 (no stop); 3) 3' entry vector Tol2kit #388 p3E-mCherrypA; 4) destination vector Tol2kit #394 pDestTol2pA2. Expression constructs were tested by transient injection, as previously described[37]. Site-directed mutagenesis was performed using the QuikChange II Kit (Agilent). The primer for point mutation (a706g) was 5'-GCCGCCGCCTGGCGTTCCG-CAAG-3' (SEQ ID NO: 10) and the clone was sequence verified after mutagenesis. This produced a dominant negative mutation in S1PR1 at the Akt phosphorylation site (T236A), which sequesters Akt and inhibits S1P-induced Rac activation[24].

Time-lapse live imaging. Staged transgenic zebrafish embryos were selected and mounted for imaging in 1% LMP agarose with E3 media and tricaine as described. Pregnant C57/BL6 mice were dissected at E11 (vaginal plug observation was E0). Embryos were removed from the uterus in PBS with 10% FCS and penicillin-streptomycin. Embryos were staged as E11 by counting ~42 somite pairs. Fetal livers were removed from the embryo and treated as described by Boisset and colleagues ("protocol b")[10]. Zebrafish embryos and fetal liver explants were imaged in MatTek glass bottom dishes (No. 1.5 cover slip). Live imaging was performed in an incubated chamber at 28° C. for zebrafish and 37° C.+humidified $CO_2$ for mouse tissue explants, which were also given culture media (DMEM, 20% FCS, glutamine, sodium pyruvate, 2-mercaptoethanol, 1% penicillin-streptomycin, recombinant mouse IL-3 (R&D Systems; final concentration 50 ng/ml)). Confocal microscopy was performed using a Yokogawa spinning disk and Nikon inverted Ti microscope. Objectives lenses were: 20× Plan-Apo DIC NA0.75; 40× Plan-Apo phase NA0.95 dry; 40× Apo LWD WI NA 1.15. Image acquisition was done with an Andor iXon DU-897 EM-CCD camera and Andor iQ computer software. Image processing and rendering was done using Fluorender[32], Imaris (Bitplane), Volocity (PerkinElmer) and ImageJ, which used the MTrackJ plugin[33] for manual cell tracking. Quantification of 12 hours of CHT tracking data per time-lapse movie allowed us to define engrafted cells as stationary (i.e. a speed of <0.31 microns/minute) and resident in the CHT for at least 3 hours, otherwise they were scored as migratory and transient.

Chemicals. Chemicals used in the study were as follows: AMD3100 (Sigma, A5602; soluble in $dH_2O$). W146 (Avanti Polar Lipids, 857390P; dissolve to 20 mM in DMSO:1 N HCl (95:5, v/v); immediately dilute 1:20 into 3% aqueous fatty acid-free BSA; final stock will be 1 mM (95 parts aqueous BSA, 5 parts acidified DMSO)). FTY720 (Cayman Chemical, 10006292; soluble in DMSO). AUY954[21] (Gift of N. Gray; soluble in DMSO). SEW2871 (Cayman Chemical, 10006440; soluble in DMSO). S1P (Sigma, S9666; soluble in MeOH). SKI-2 (Cayman Chemical, 10009222; soluble in DMSO).

Lineage tracing. Lineage tracing was performed by injection of 1 nl of a 1:5 dilution of caged fluorescein dextran (MW 10000). At 28 hpf embryos were mounted in 1% LMP agarose with E3 media and tricaine. The DA region was targeted and uncaged with the 405 nm laser line of a Leica SP5X laser scanning confocal microscope. Embryos were recovered from agarose and raised to 46 hpf either in E3 or E3+W146 (10 μM). Embryos were fixed for one hour in 4% formaldehyde (Polysciences, 04018)/1×PBS. Blocking was done in PBS/0.1% Triton X-100 (PBT)+5% FCS and 0.1% BSA. Mouse anti-GFP (1:500) and rabbit anti-fluorescein (1:1000) primary antibodies were added to block and incubated overnight at 4° C. Washes were in PBT at 4° C. Alexa Fluor 488 goat anti-mouse and Alexa Fluor 546 goat anti-rabbit secondary antibodies (Invitrogen) were added to PBT (1:400), incubated for 2 hours at RT, and washed with PBT. Embryo tails were removed with needles and mounted under a No. 1.5 coverslip in SlowFade antifade reagent (Invitrogen).

Embryo-to-embryo transplantation. Runx1+23:NLS-mCherry 3 dpf embryos were collected and chopped finely with a razor blade. Embryos were dissociated in a 1:65 dilution of Liberase TM (Roche) in PBS, incubated at 37° C. for 20 minutes before addition of PBS/5% FCS to stop the reaction. Dissociated cells were passed through a 45 μM filter, spun, and resuspended in 0.9% PBS/5% FCS. mCherry positive cells were collected using a FACSAria cell sorter (BD Biosciences). Collected cells were resuspended in 0.9% PBS/5% FCS/Heparin/DNAse, loaded into a micro-injection needle (no filament), and injected into the sinus venosus/Duct of Cuvier of a 48 hpf embryo recipient. Embryos were raised to adulthood (10 weeks) and whole kidney marrow was analyzed for percentage of engrafted mCherry positive cells using a LSR II flow cytometer (BD Biosciences).

Example 1

Hematopoietic stem and progenitor cells (HSPCs) first arise from the hemogenic endothelium of the dorsal aorta (DA), are released into circulation, and then seed the fetal liver (FL) as an intermediate tissue before colonizing the adult bone marrow. Despite extensive characterization of hematopoietic sites during ontogeny, the engraftment has not been directly visualized and the mechanism is poorly understood. Here, the inventors demonstrate that arrival of an HSPC in a hematopoietic tissue triggers endothelial cells to remodel into a supportive stem cell niche. Using live imaging of zebrafish embryos, the inventors demonstrate sequential steps of engraftment including adherence to the endothelial wall, extravasation, and endothelial cell cuddling of the stem cells, followed by quiescence or cell division. Live imaging of mouse FL explants demonstrates that endothelial cells (CD31+) adhere to and form a rosette around a single HSPC (c-kit+), similar to the process in zebrafish. A chemical genetic screen using zebrafish embryos found an important role for sphingosine-1-phosphate (S1P) and its interaction with CXCR4-CXCL12 signaling for engraftment. The S1P receptor acts in a cell autonomous manner during the seeding. Herein, the inventors demonstrate a hierarchy of steps of HSPC seeding of hematopoietic organs and suggest that modulation of each critical step could have impact on stem cell mobilization and engraftment.

Figure 7A:
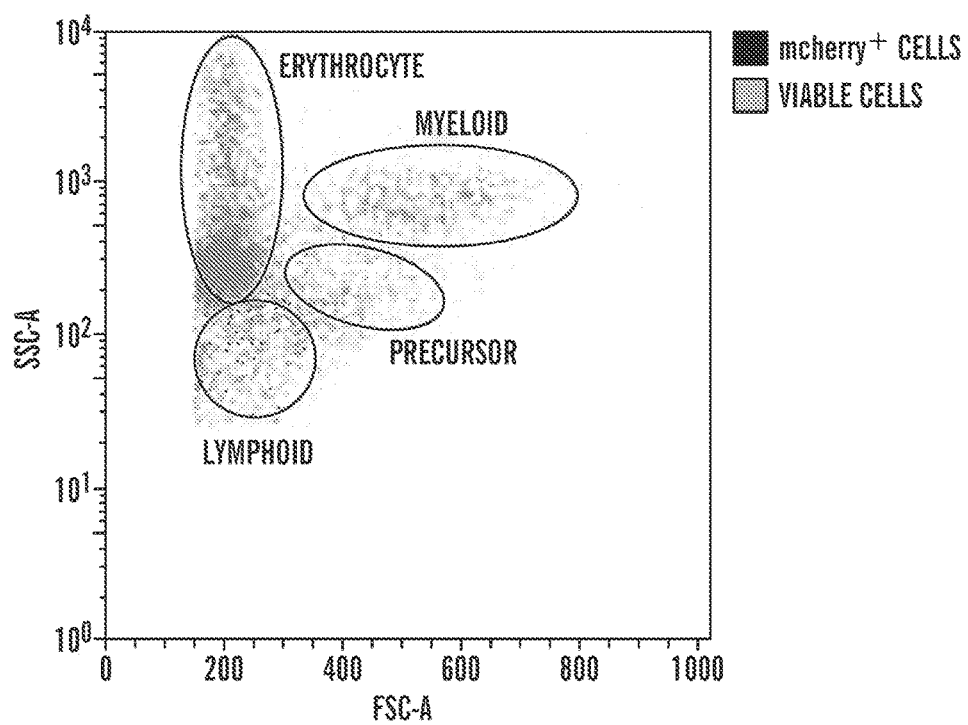
FIGS. 7A-7B show whole kidney marrow (WKM) sorted from Runx1+23:NLS-mCherry transgenics and embryo-to-embryo transplant recipients.
Figure 7B:
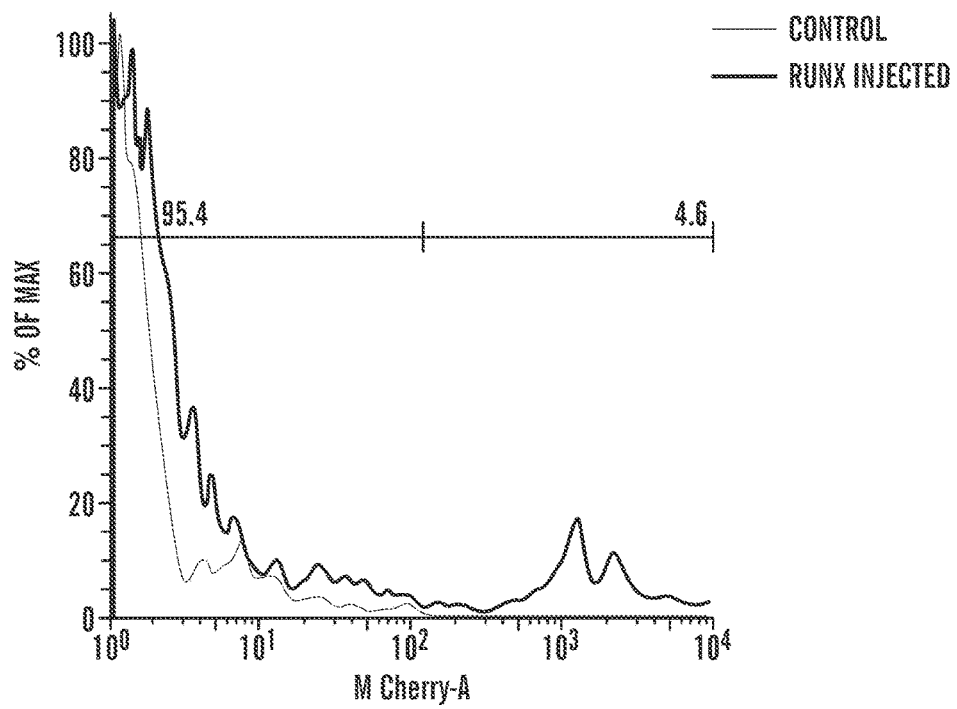
Figure 9A:
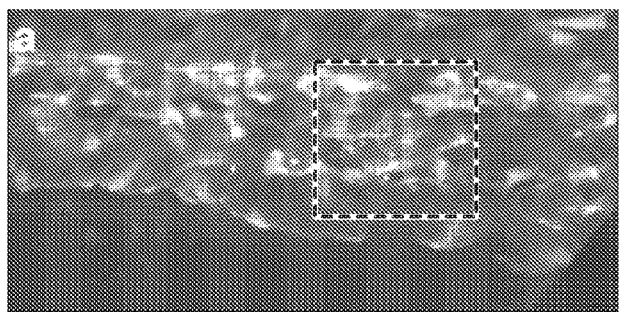
FIGS. 9A-9F show the CHT of a double transgenic 40 hpf embryo expressing cxcl12a:DsRed2 and kdrl:EGFP. cxcl12a:DsRed2 positive stromal cells are distinct but closely associated with kdrl:EGFP[36] positive endothelial cells.
Figure 9B:
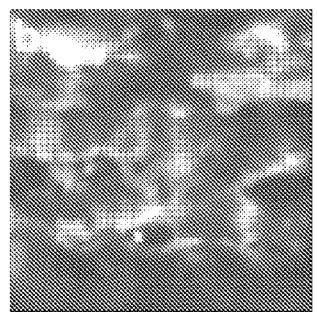
Figure 9C:
Figure 9D:
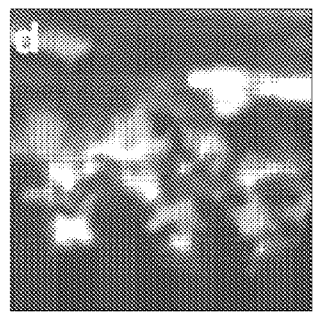
Figure 9E:
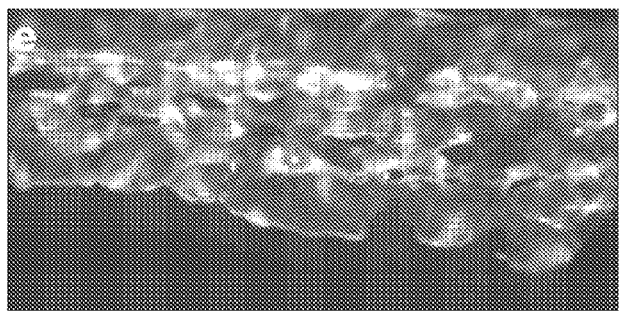
Figure 9F:
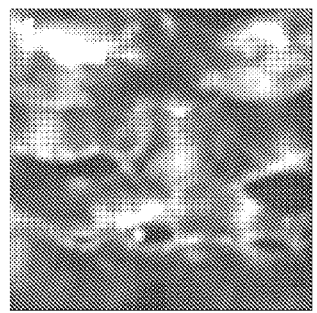

Live imaging was used to describe the conserved events that unfold after HSPC migration and arrival in the intermediate hematopoietic tissue—the caudal hematopoietic tissue (CHT) in zebrafish and FL in mammals. To precisely track HSPCs in the zebrafish embryo, the inventors created a novel transgenic line using the previously characterized Runx1+23 kb intronic enhancer that delineates this population in the mouse embryo[1]. The Runx1+23 zebrafish reporter is specifically expressed in sites of definitive hematopoiesis from embryo to adult. Runx1+23 positive cells were confirmed as definitive HSPCs by co-expression with previously characterized reporter lines (e.g. cd41:EGFP[2,3] and cmyb:EGFP[4]), lineage tracing from their origin in the DA, expression in the adult kidney marrow, and embryo-to-embryo transplantation of sorted positive cells to show adult engraftment at 10 weeks (FIGS. 5-7).

Figure 1C:
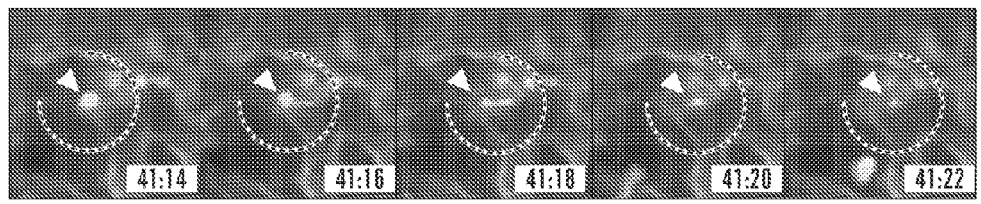
Figure 1D:
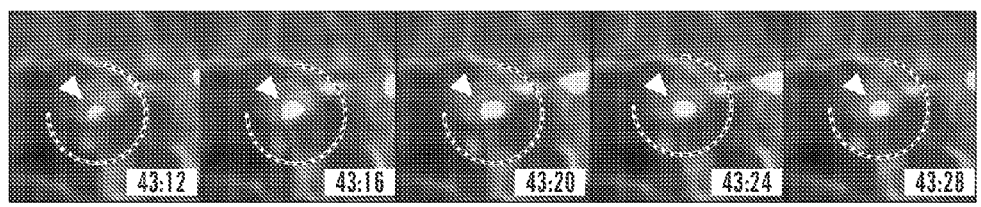
Figure 1E:
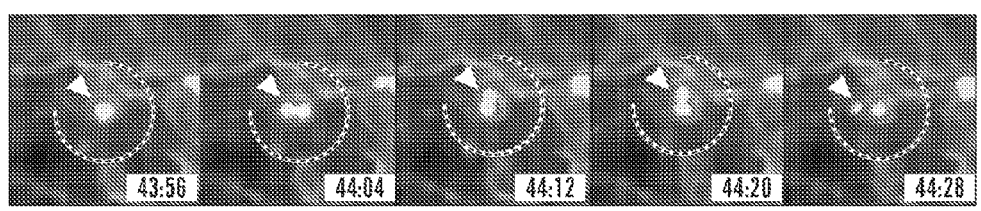
Figure 2A:
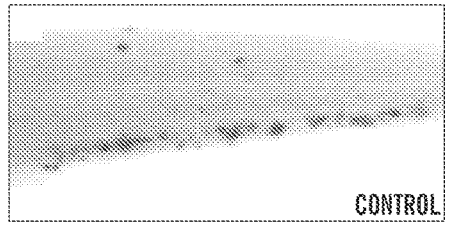
FIGS. 2A-2R show S1P and CXCR4-CXCL12 signaling axes interact in CHT hematopoiesis and shows S1P and S1PR1 agonists have a dynamic interaction in combination with CXCR4 antagonist AMD3100.
Figure 2B:
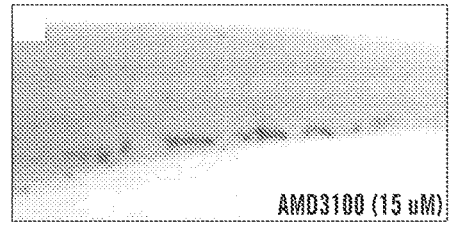
Figure 2C:
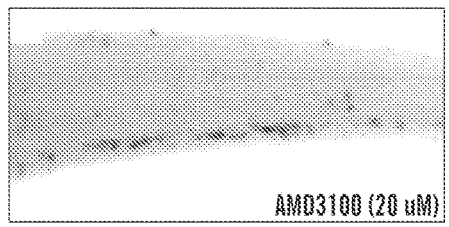
Figure 2D:
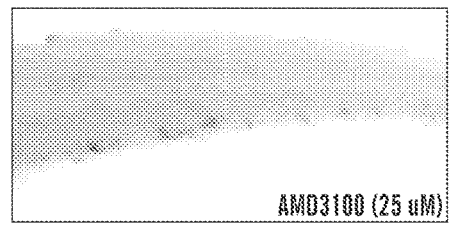
Figure 2E:
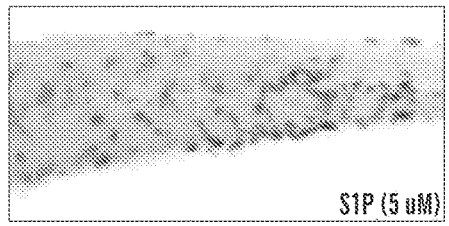
Figure 2F:
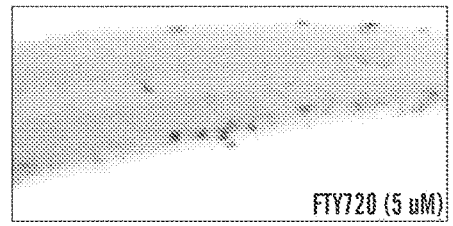
Figure 2G:
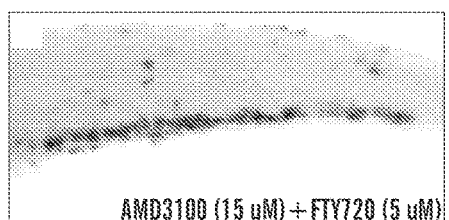
Figure 2H:
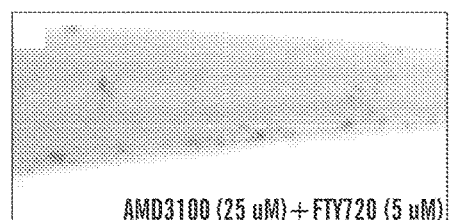
Figure 2I:
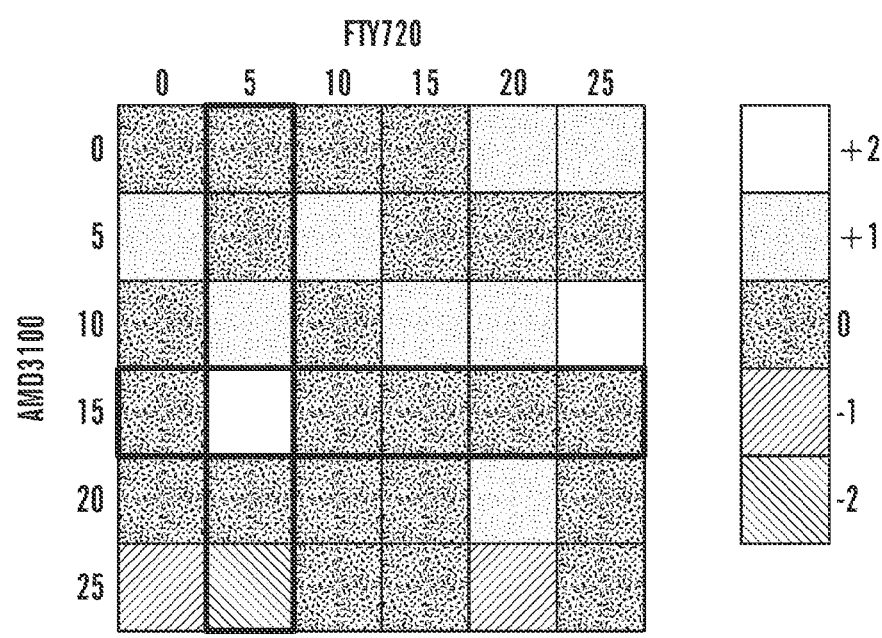
FIG. 2I shows a representative dose matrix of FTY720 compound to determine effects of combinatorial drug treatment on CHT hematopoiesis, with the effect of increasing dose of CXCR4 antagonist AMD3100 with increasing dose of FTY720 on HSC engraftment, showing greatest engraftment with a +2 CHT score with 15 µM AMD3100 and 5 µM FTY720 (as shown by the centered box) In particular, the box indicates an observation of an increased migratory phenotype of myeloid progenitor cells (e.g. neutrophils and macrophages) as shown by whole mount in situ hybridization of cmyb/runx1 probes. We interpret this not necessarily as an indicator of mobilization or engraftment, but instead as a general activation of hematopoietic progenitors within the embryo. The box indicates the column (or fixed dose) of S1PR1 agonist in the zebrafish assay that is optimal for titration against AMD3100 for maximal engraftment.
Figure 2J:
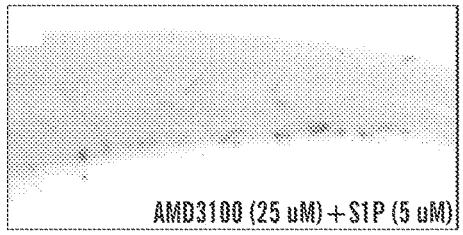
FIG. 2J, 2K shows S1P and AMD3100, FIGS. 2L,2M and N show S1PR1 agonists AUY954 alone or with AMD3100 at 15µM or 25µM
Figure 2K:
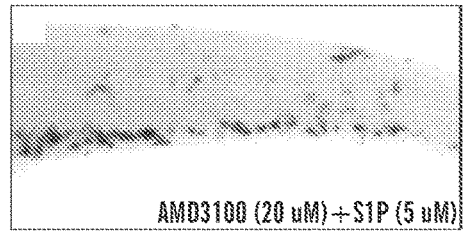
Figure 2L:
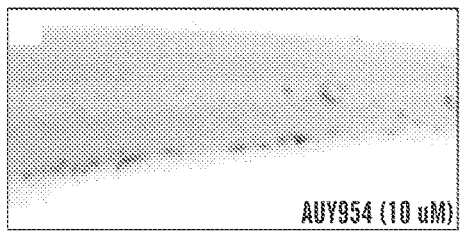
Figure 2M:
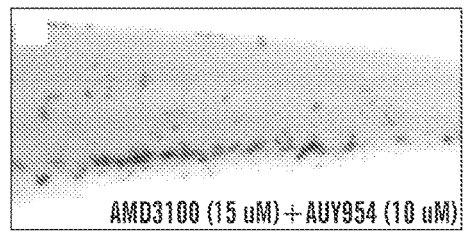
Figure 2N:
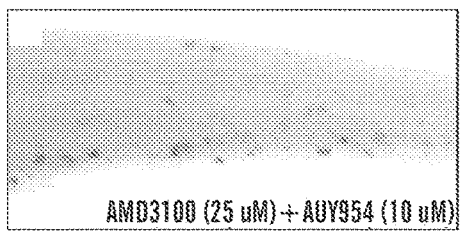
Figure 2O:
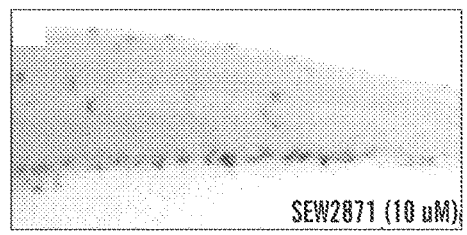
FIGS. 2O, 2P and 2Q show SEW2871 alone or with AMD 3100 at 15µM or 25µM have dynamic interactions in combination with AMD100.
Figure 2P:
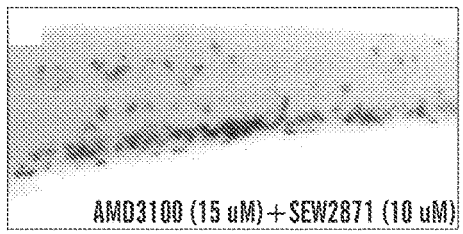
Figure 2Q:
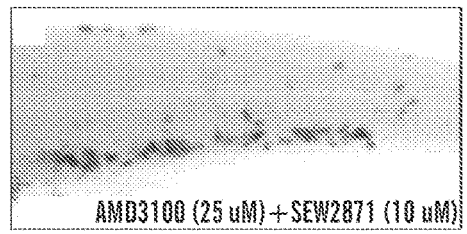
Figure 2R:
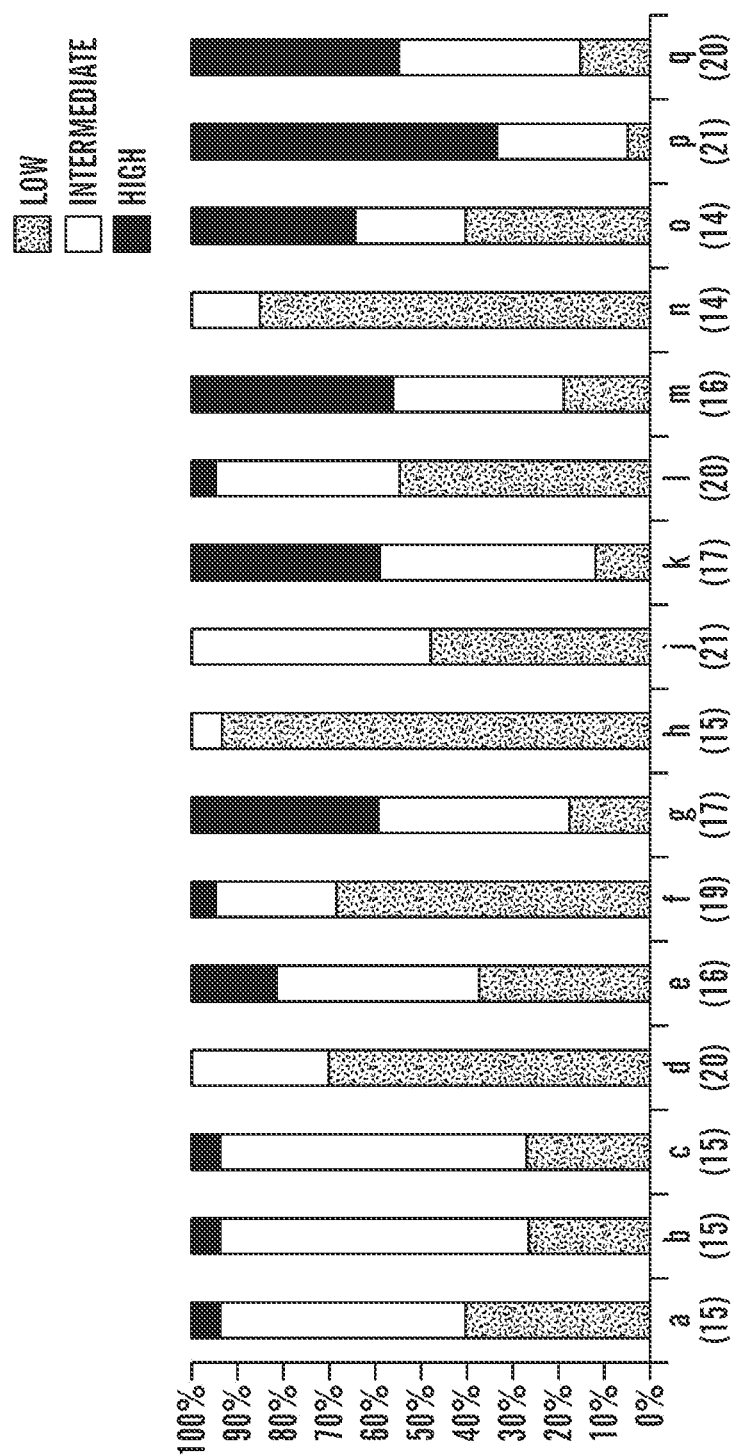
Figure 3A:
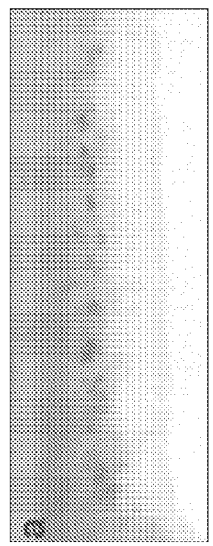
FIGS. 3A-3L shows S1PR1 is required for proper seeding of the CHT.
Figure 3B:
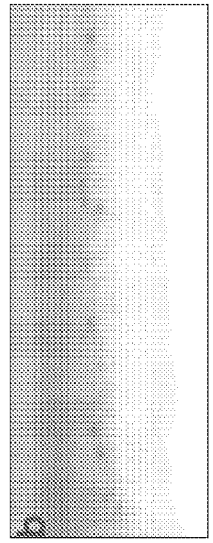
Figure 3C:
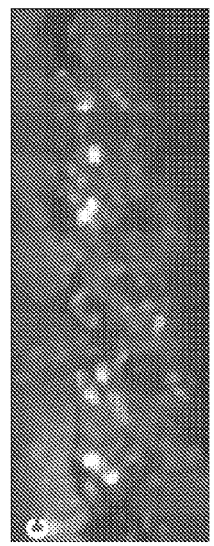
Figure 3D:
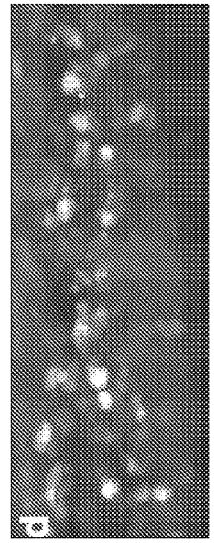
Figure 3E:
Figure 3F:
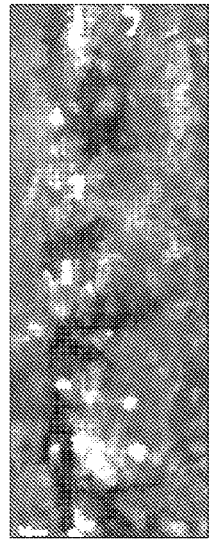
Figure 3H:
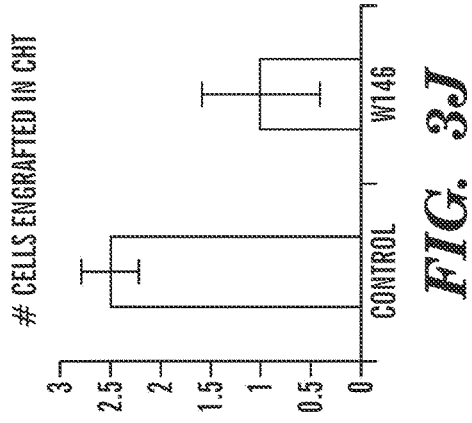
Figure 3J:
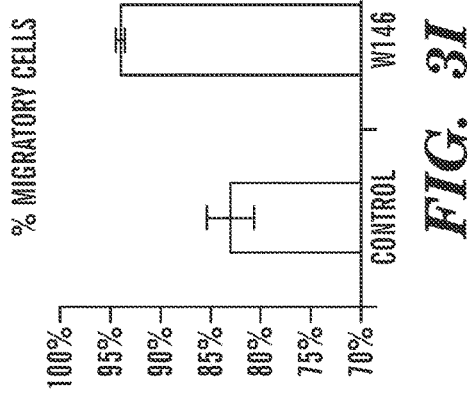

HSPCs in the CHT originate in the hemogenic endothelium of the DA and arrive via circulation. By imaging double transgenic embryos (Runx1+23:EGFP; kdrl:DsRed2), the inventors could observe HSPCs in relation to endothelial cells. HSPC migration from the DA to the CHT begins at ~30 hours post fertilization (hpf), increases until 48 hpf, then wanes by 72 hpf[5-8]. The CHT was imaged between ~38 and 54 hpf to capture the peak window of migration events, which are still rare. During these stages, the CHT is a vascular plexus between the caudal artery and vein in the ventral tail of the embryo. It undergoes remodeling to become distinct from circulation and create a hematopoietic microenvironment, complete with stromal-like fibroblast cells'. Using time-lapse live imaging, the inventors observed HSPC arrival in the CHT and adherence to endothelial walls (FIG. 1C and data not shown). Next, cells underwent rapid extravasation to the abluminal side of the endothelial wall (FIG. 1C). Once HSPCs arrived in the CHT, we made a striking and novel observation: endothelial cells remodeled around the stem cell to form a closely associated niche—an event referred to herein as "endothelial cuddling" (FIG. 1D). The events were quantified by tracking Runx1+23:EGFP cells in the CHT from ~38 to 50 hpf (n=4 movies; FIG. 3J). Cells were scored as being engrafted if they were stationary and resident in the CHT for at least 3 hours (details in Methods Section). Based on these criteria, only 2-3 HSPCs engrafted in the CHT during this 12 hour period, although they expanded greatly over the next few days (FIG. 5). Occasionally, early engrafting HSPCs would undergo an asymmetric division producing a daughter cell that would migrate out of the niche (FIG. 1E); others would undergo a symmetric division or remain quiescent. Different steps of CHT seeding were also observed in other HPSC transgenic lines (data not shown). The rare engraftment events between an HSPC and its surrounding endothelial cells mark the formation of a hematopoietic niche.

Next the inventors assessed if niche formation by endothelial cells is conserved in higher vertebrates. It has been well established in mice that the first long-term repopulating HSPCs of aortic origin arrive in the FL at E11 and are a strongly c-kit+ population[9]. To observe the behavior of these c-kit+ cells in FL, the inventors applied an established live imaging protocol for mouse DA tissue[10]. A dissected non-fixed FL was treated with fluorophore-conjugated antibodies, incubated in live culture conditions and imaged by confocal microscopy. The three-dimensional microanatomy of the hepatic sinusoids[11] was well preserved in these non-fixed explants (FIG. 1F-1H). A single lobe of the FL could be imaged to a depth of ~80 microns, which allowed reconstruction of positional information from z-stack images (data not shown). Within the explant, a small number of strongly c-kit+ cells were found associated with sinusoids, either inside or outside and adjacent to the lumen. This configuration is similar to the expanded c-kit+ population observed later in E12.5 FL[12] (FIG. 1H). To follow the dynamic behavior of c-kit+ cells in E11 FL, time-lapse imaging was performed under live culture conditions (FIG. 1G and data not shown). Rare events were observed that involved a small number of endothelial cells forming a rosette around a c-kit+ cell. All time-lapse experiments (n=8) revealed 1-6 c-kit+ cells in each FL lobe, but only 0-2 events in each 7.5-hour period. There is remarkable similarity between these events and "endothelial cuddling" observed in the zebrafish CHT. During mouse and zebrafish ontogeny, arrival of an HSPC in a site of hematopoiesis sets off a conserved pattern of cellular behavior: a small group of endothelial cells creates a niche around a single stem cell.

Figure 10:
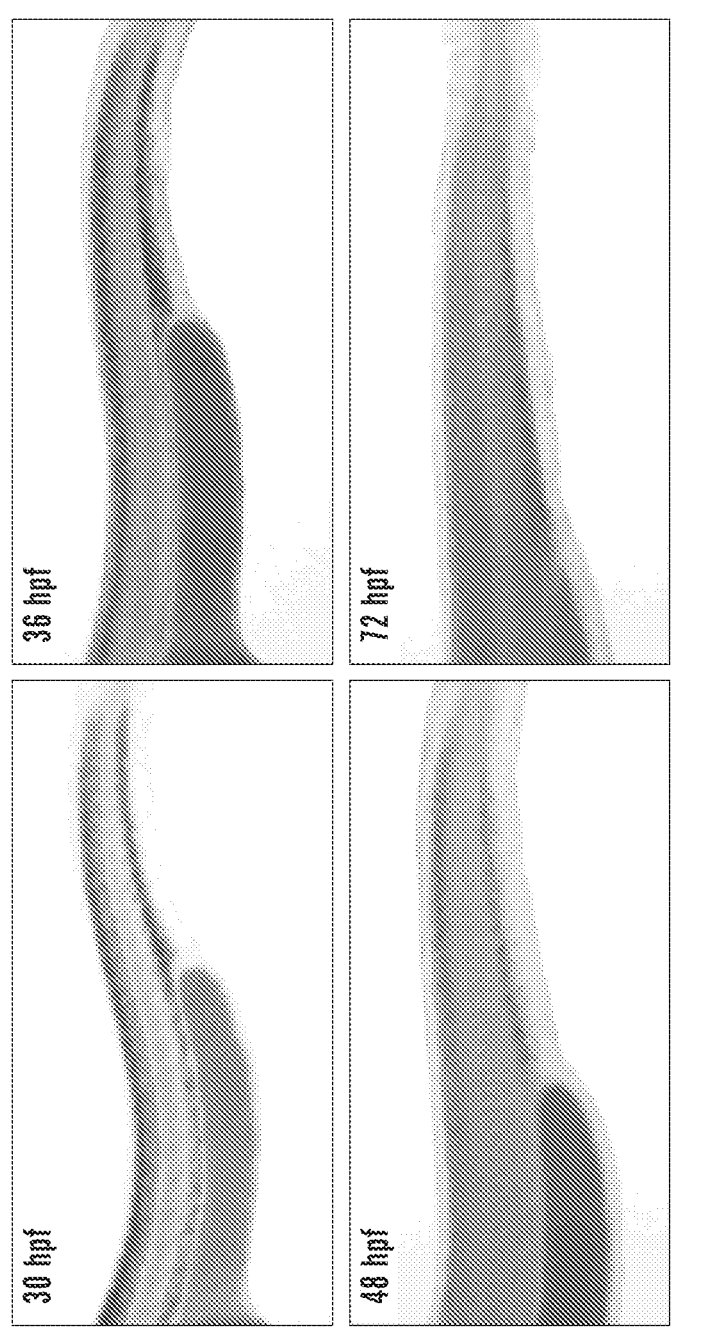
FIG. 10 shows whole mount in situ expression pattern of s1pr1. Posterior of 30, 36, 48 and 72 hpf embryos showing the DA and/or CHT region. s1pr1 is expressed in the head (not shown), the neural tube, DA and CHT. DA expression decreases over time and expression becomes restricted to the CHT. Anterior is left and ventral is below. Note: some background was allowed in the staining to detect any low level expression.
Figure 11A:
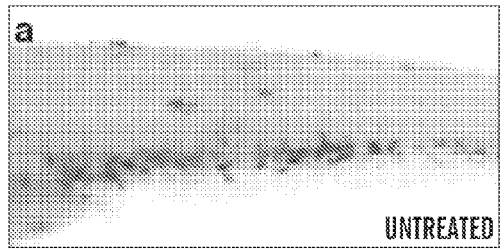
FIG. 11A-11K show combinatorial chemical genetics to address the role of S1P-S1PR1 signaling in CHT hematopoiesis.
Figure 11B:
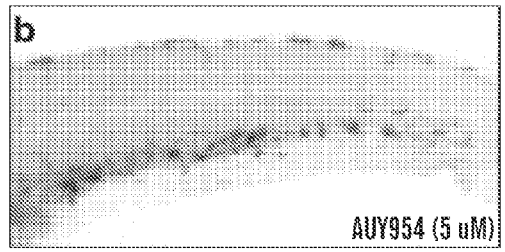
Figure 11C:
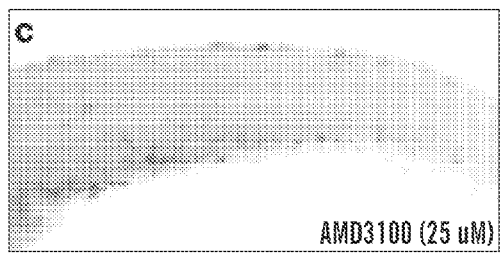
Figure 11D:
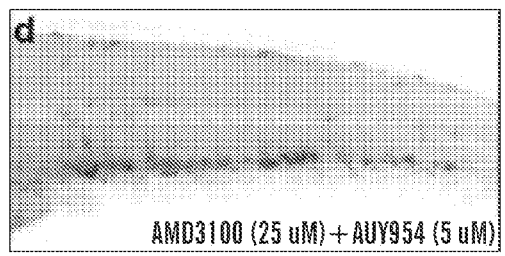
Figure 11E:
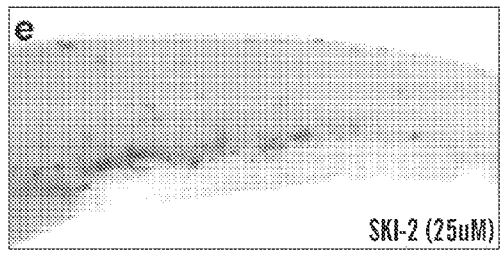
Figure 11F:
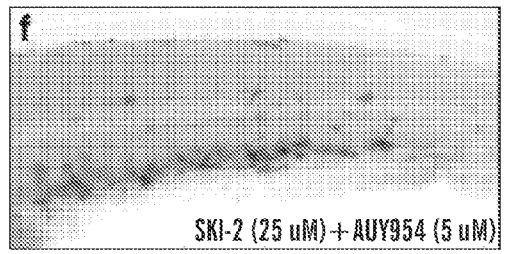
Figure 11G:
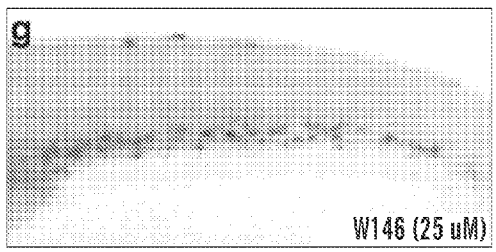
Figure 11H:
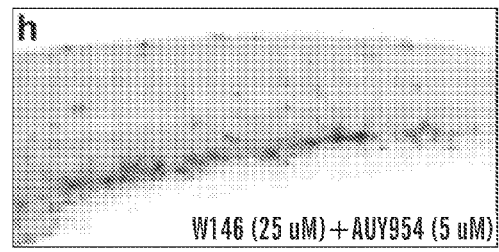
Figure 11I:
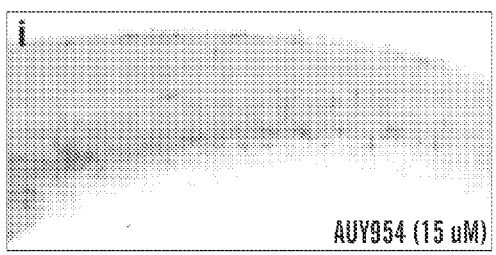
Figure 11J:
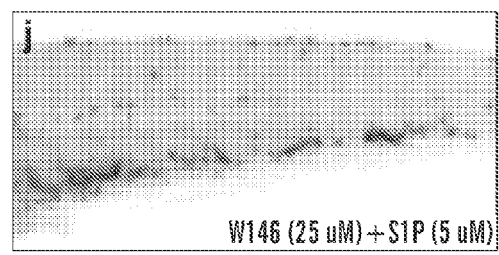
Figure 11K:
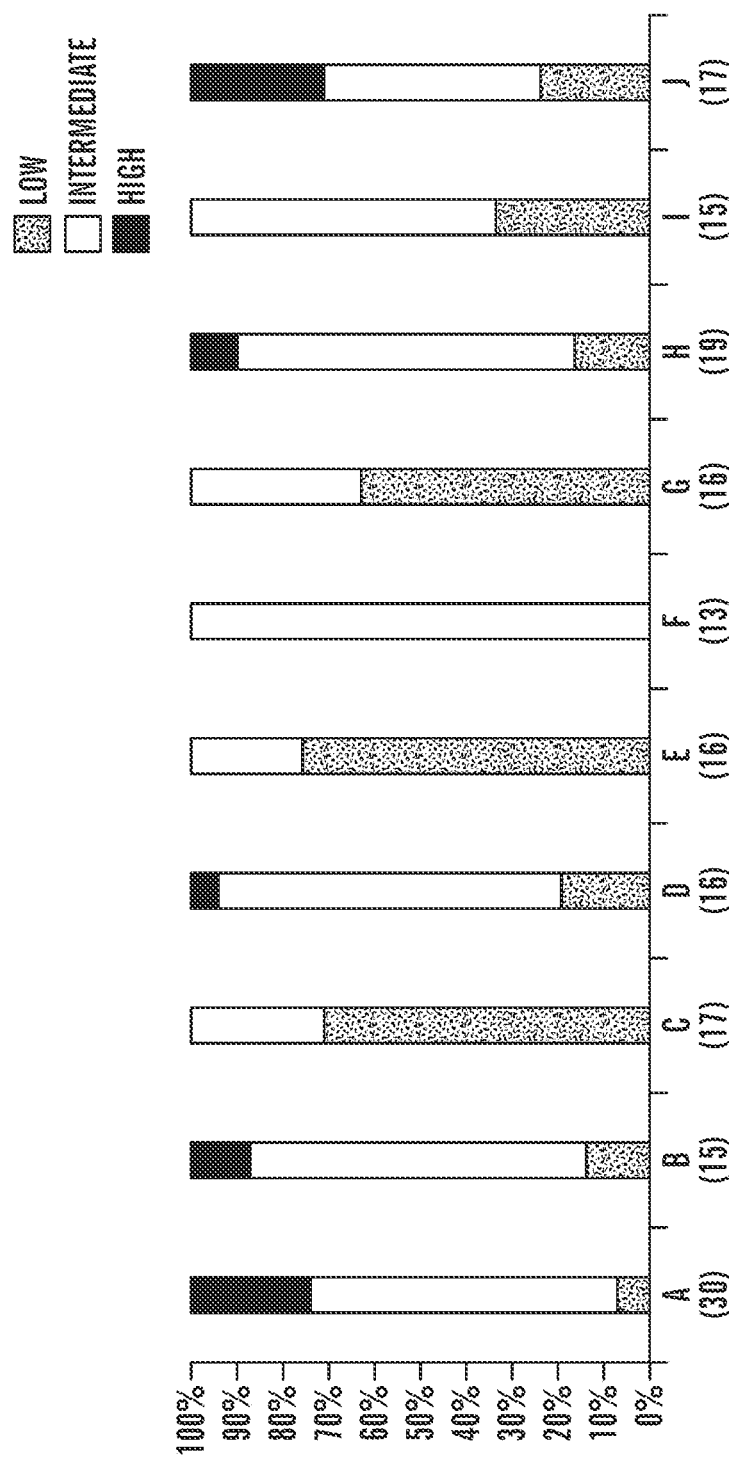

Having followed newly born aortic HSPCs to the intermediate tissue, the inventors assessed the signaling pathways involved in embryonic migration. The inventors designed a chemical genetic screen to introduce small molecules to the zebrafish embryo from the peak window of HSPC migration to the CHT (48-72 hpf). The gene homologs for CXCR4 and CXCL12 are expressed in the DA and CHT, and a cxcl12a transgenic reporter[13] is expressed in CHT stromal cells (FIGS. 8 ad 9). To control for decrease of HSPC markers cmyb and runx1 in the CHT, the embryos were treated with CXCR4 antagonist, AMD3100 (FIG. 2). After 24 hour treatment, AMD3100 dose-dependently reduced HSPC markers in the CHT at 72 hpf (FIG. 2A-2D). Screening 2400 compounds identified sphingosine-1-phosphate (S1P) as a bioactive lipid that altered the migration pattern of HSPCs in the embryo (FIG. 2E), a signal known to regulate lymphocyte and HSPC trafficking in adult mice[14,15]. Using various chemical modulators of the S1P pathway, the inventors discovered the requirement for its endogenous levels and S1P receptor 1 (s1pr1), which is expressed in the DA and CHT (FIG. 10 and FIG. 11). Furthermore, the inventors demonstrate a highly dynamic interaction between CXCR4-CXCL12 and S1P signaling pathways, an interaction that has been suggested in adult HSPC trafficking[16-19]. By creating dose matrices with chemical modulators of both pathways, the inventors demonstrate that there are synergistic increases in CHT hematopoiesis when combining AMD3100 with S1P or three independent S1PR1 agonists (e.g. FTY720[20], AUT954[21], SEW2871[22]; FIG. 2). Accordingly, the inventors have demonstrated that migration between DA and CHT is tightly regulated by signaling pathways that include S1P and CXCR4-CXCL12.

Figure 3G:
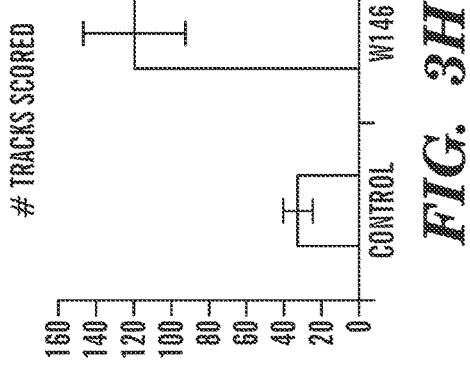
Figure 3I:
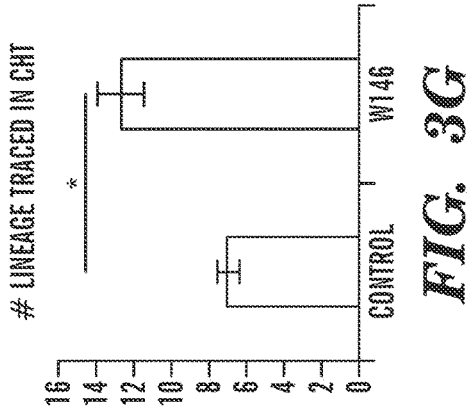
Figure 3K:
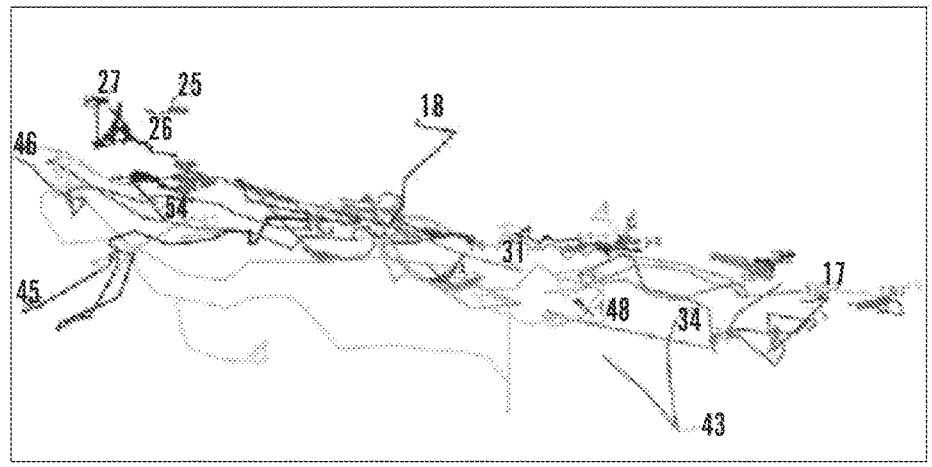
Figure 3L:
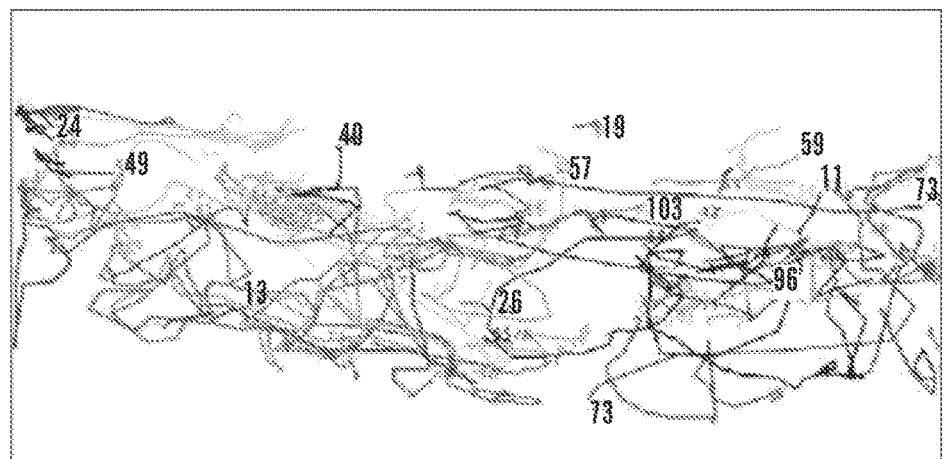
Figure 6B:
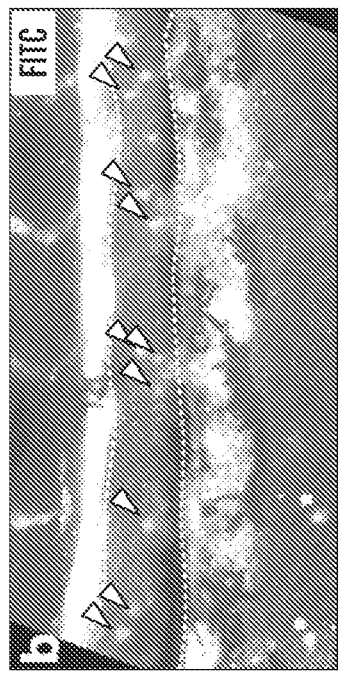
FIG. 6A-6D show the lineage tracing to confirm that Runx1+23:NLS-mCherry positive cells in the CHT originate in the DA. Runx1+23:NLS-mCherry embryos were injected with caged FITC, the DA was UV uncaged at 28 hpf, and embryos were fixed at 46 hpf. Colocalization of Runx1+23:NLS-mCherry, uncaged FITC, and DAPI+ nuclei were observed in confocal scans of the CHT (between the dotted lines) in fixed embryos.
Figure 6D:
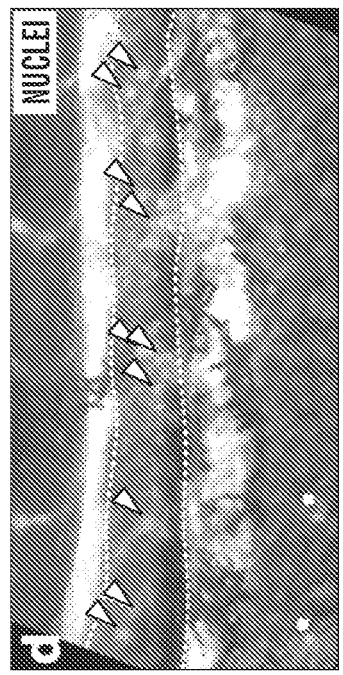
Figure 6A:
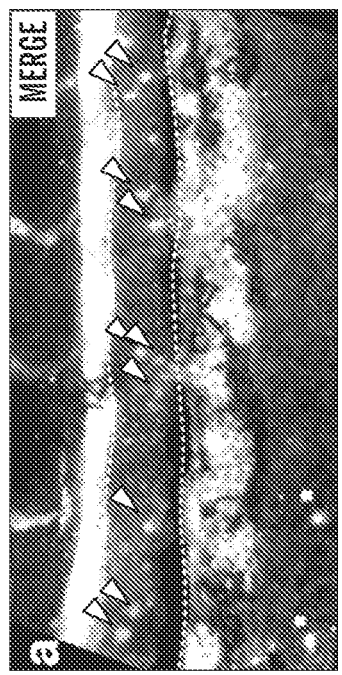
Figure 6C:
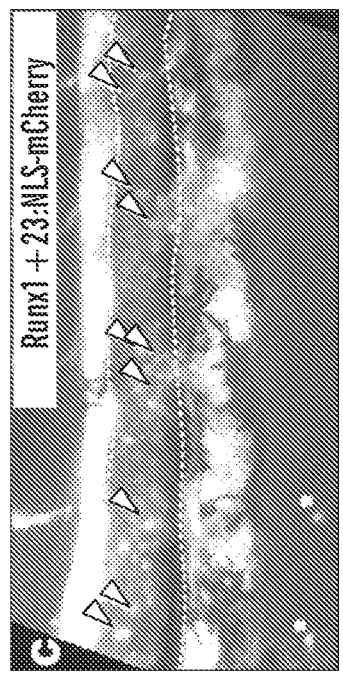
Figure 12A:
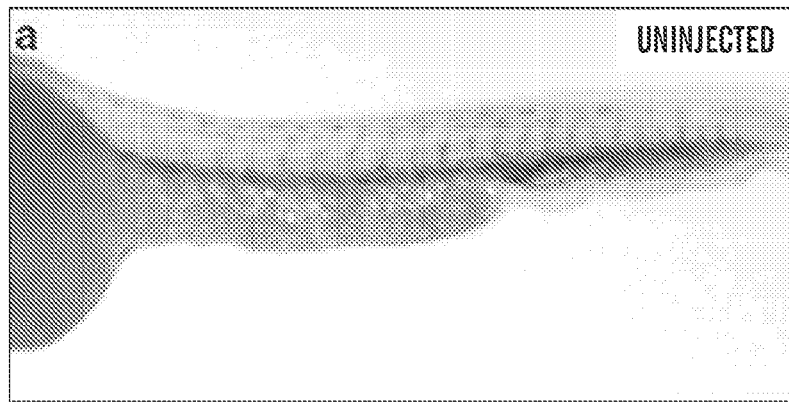
FIG. 12A-12B show the effect of s1pr1 morpholino on vascular development. Injection of s1pr1 ATG morpholino at a dose of 1 ng does not effect circulation (FIG. 3). However, injection of 2 ng or more s1pr1 morpholino stops circulation.
Figure 12B:
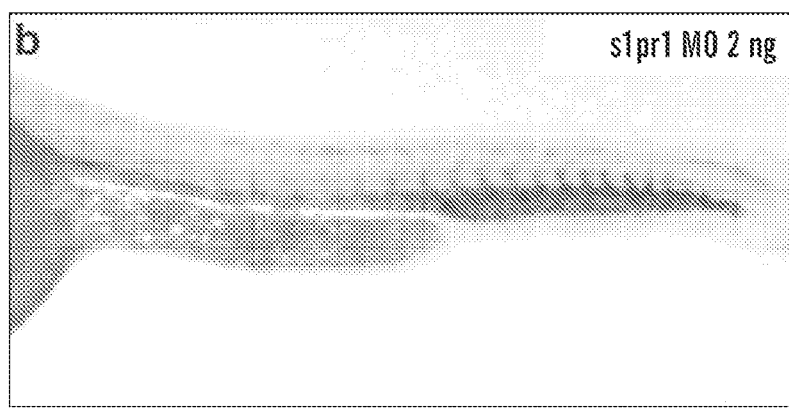
Figure 13A:
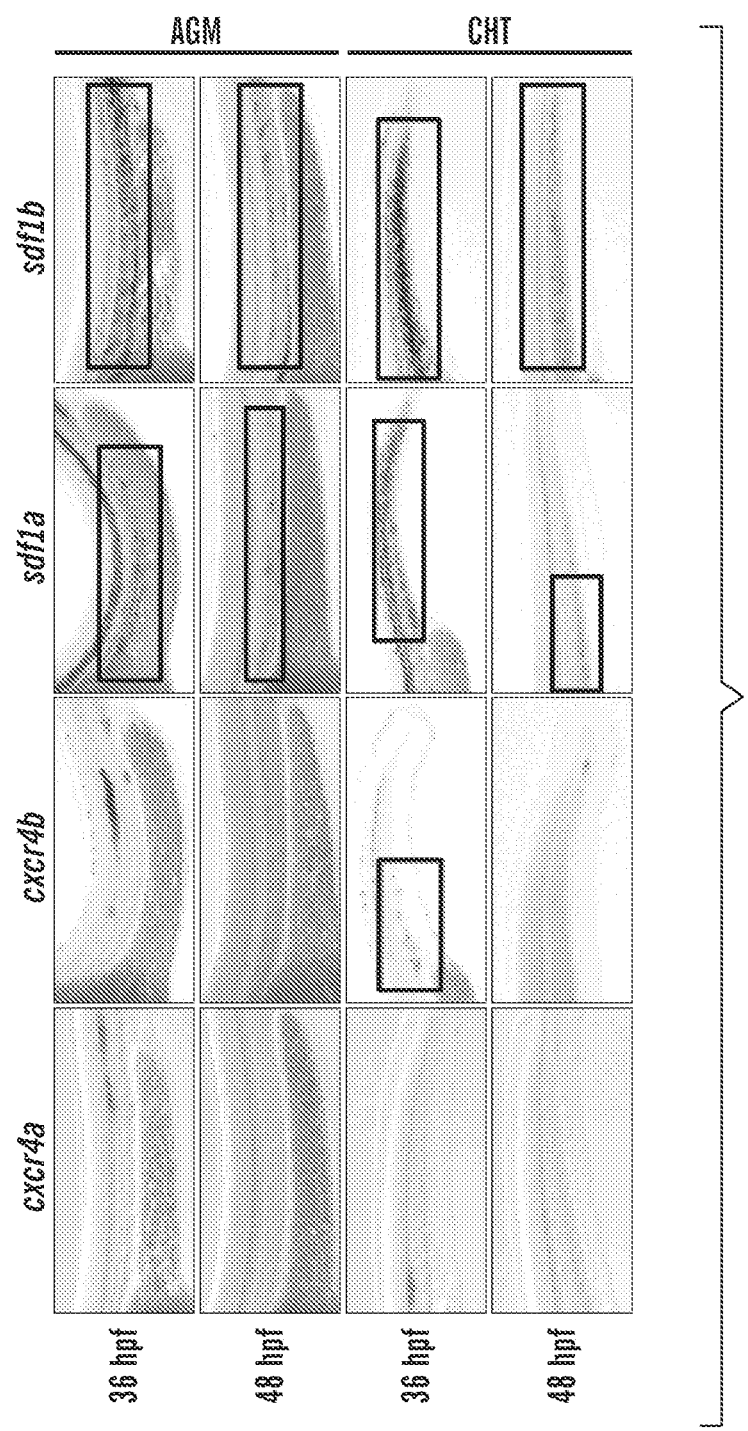
FIG. 13A-13B show whole mount expression patterns of CXCR4/SDF-1 expression in AGM and CHT.
Figure 13B:
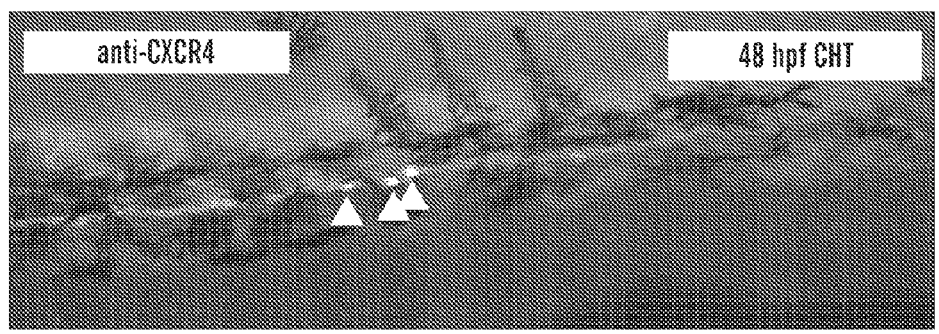
Figure 14:
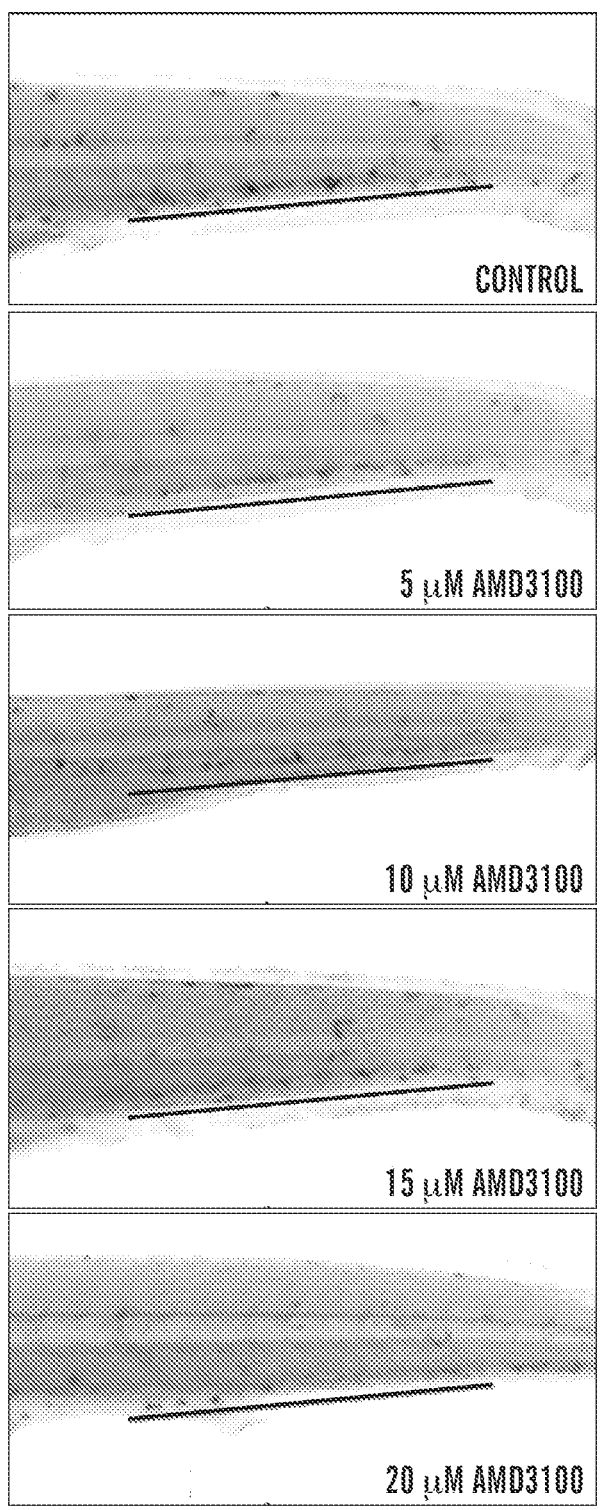
FIG. 14 show chemicals affect homing of HSCs to the CHT. CXCR4/SDF-1 axis is a candidate signal for homing to the CHT. Redundancy of genes in zebrafish makes knockdown difficult, however, the CXCR4 antagonist, AMD3100 (5 µM-20 µM), disrupts all receptor/ligand interactions.

To confirm a genetic function for s1pr1 in CHT hematopoiesis, the inventors performed morpholino knockdown using a previously validated morpholino[23]. Knockdown embryos had reduced HSPCs in the CHT, shown by runx1 expression, without disruption of circulation or vasculature (FIGS. 3A, 3B; and FIG. 12). Knockdown in a cmyb:EGFP; kdrl:DsRed2 background showed increased progenitors, shown by cmyb:EGFP+ cells (FIGS. 3C, 3D). To confirm that this expanded population was of aortic origin, lineage tracing was performed in a cd41:EGFP background in the presence of the S1PR1-specific antagonist, W146. In replicate experiments, cd41:EGFP+ aorta-derived progenitors in the CHT increased and had morphology that differed from the control (FIG. 3E-3G). Live imaging of Runx1+23:EGFP; kdrl:DsRed2 embryos was repeated with S1PR1 antagonist (data not shown). Applying the cell tracking method above, the inventors discovered that the tracked cells increased, the percentage of migratory cells increased, while the number of engrafted cells decreased (FIG. 3H-3L). Together, these data demonstrate that blockade of s1pr1 signaling does not prevent arrival of HSPCs in the CHT, but does disrupt their engraftment.

In an effort to test the cell autonomous function of s1pr1 in embryonic HSPCs, the same Runx1+23 enhancer was used to transiently express wild-type (WT) or dominant-negative[24] (DN) human S1PR1 in HSPCs. Receptor cDNAs were fused to mCherry fluorescent protein for visualization. Injection of constructs into cd41:EGFP and cmyb:EGFP backgrounds confirmed expression in the correct cell type (FIGS. 4A, 4B). Live imaging of DN-S1PR1 expressing HSPCs in the CHT of a cmyb:EGFP+ embryo revealed that cells make contact, however, they fail to engraft and lose their round progenitor-like morphology (data not shown). Using increased magnification imaging over a one-hour period, cells expressing WT-S1PR1 retained a round morphology with receptor localized primarily at the cell surface (FIG. 4C; n=6/7 total cells from 4 movies). In contrast, cells expressing DN-S1PR1 were continually remodeling and extending protrusions, with receptor largely in the cytoplasm (FIG. 4D; n=9/15 total cells from 4 movies). Together, the inventors demonstrated that HSPC extravasation in the CHT, but not adhesion to the endothelium, requires proper transduction of S1P signal for remodeling of cell shape. It is known that S1P can regulate a RhoA-dependent mechanism for tail retraction in the rear of migratory hematopoietic cells, a mechanism that is also used for transendothelial migration and invasion into stromal cell layers[25-29]. The surface localization of WT-S1PR1 in engrafted cells, and the cytoplasmic expression of DN-S1PR1 in non-engrafted cells, is consistent with cyclical modulation of S1PR1 observed in adult lymphocytes as they traffic between tissue and circulation, respectively[30]. Thus the inventors have discovered that each step of engraftment is distinct and has its own specific use of signaling pathways and surface receptors.

Accordingly, the inventors have defined the in vivo the events and mechanisms by which HSPCs migrate to and associate with a niche. The inventors have demonstrated four sequential stages of engraftment: attachment, extravasation, endothelial cuddling, and decisions during cell division. The unexpected interaction between HSPC and endothelial cells indicates a unique and dynamic interaction between the two cell types depending on whether HSC migration or engraftment is occurring. In particular, the inventors have demonstrated that the arrival of a stem cell, e.g., HSC may signal endothelial cells to react through surface receptors and binding proteins such as integrins, and this initial interaction triggers a response by the HSPC to maintain niche localization or to leave.

REFERENCES

All references cited in the Examples and Specification are incorporated herein in their entirety.

[1] Nottingham, W. T. et al. Blood 110, 4188-4197 (2007).
[2] Lin, H.-F. et al. Blood 106, 3803-3810 (2005).
[3] Ma, D. et al. Blood 118, 289-297 (2011).
[4] North, T. E. et al. Nature 447, 1007-1011 (2007).
[5] Kissa, K. & Herbomel, P. Nature 464, 112-115 (2010).
[6] Kissa, K. et al. Blood 111, 1147-1156 (2008).
[7] Murayama, E. et al. Immunity 25, 963-975 (2006).
[8] Bertrand, J. Y. et al. Nature 464, 108-111 (2010).
[9] Sánchez, M. J., Holmes, A., Miles, C., & Dzierzak, E. Immunity 5, 513-525 (1996).
[10] Boisset, J.-C. et al. Nature 464, 116-120 (2010).
[11] Motta, P. M. Arch Histol Jpn 47, 1-30 (1984).
[12] Iwasaki, H. et al. Blood 116, 544-553 (2010).
[13] Glass, T. J. et al. Blood 118, 766-774 (2011).

[14] Rivera, J., Proia, R. L., & Olivera, A. Nat Rev Immunol 8, 753-763 (2008).
[15] Massberg, S. et al. Cell 131, 994-1008 (2007).
[16] Kimura, T. et al. Blood 103, 4478-4486 (2004).
[17] Ryser, M. F. et al. Mol Immunol 46, 166-171 (2008).
[18] Ratajczak, M. Z. et al. Leukemia 24, 976-985 (2010).
[19] Juarez, J. G. et al. Blood (2011).
[20] Mandala, S. et al. Science 296, 346-349 (2002).
[21] Pan, S. et al. Chem Biol 13, 1227-1234 (2006).
[22] Jo, E. et al. Chem Biol 12, 703-715 (2005).
[23] Kai, M., Heisenberg, C.-P., & Tada, M. Development 135, 3043-3051 (2008).
[24] Lee, M. J. et al. Mol Cell 8, 693-704 (2001).
[25] Fonseca, A.-V., Freund, D., Bornhäuser, M., & Corbeil, D. J Biol Chem 285, 31661-31671 (2010).
[26] Koh, E. et al. Cell Signal 19, 1328-1338 (2007).
[27] Yanai, N. et al. Blood 96, 139-144 (2000).
[28] Worthylake, R. A. & Burridge, K. J Biol Chem 278, 13578-13584 (2003).
[29] Worthylake, R. A., Lemoine, S., Watson, J. M., & Burridge, K. J Cell Biol 154, 147-160 (2001).
[30] Lo, C. G., Xu, Y., Proia, R. L., & Cyster, J. G. J Exp Med 201, 291-301 (2005).
31 Huang, H. et al. BMC Dev Biol 5, 7 (2005).
32 Wan, Y., Otsuna, H., Chien, C. B., & Hansen, C. IEEE Trans Vis Comput Graph 15, 1489-1496 (2009).
33 Meijering, E., Dzyubachyk, O., Smal, I., Methods for Cell and Particle Tracking in Methods in Enzymology: Live Cell Imaging, edited by P. M. Conn (Elsevier, in press).
34 Thisse, C. & Thisse, B. Nat Protoc 3, 59-69 (2008).
35 Traver, D. et al. Nat Immunol 4, 1238-1246 (2003).
36 Jin, S.-W. et al. Development 132, 5199-5209 (2005).
37 Kwan, K. M. et al. Dev Dyn 236, 3088-3099 (2007).
38 Mosimann, C. et al. Development 138, 169-177 (2011).

The invention claimed is:

1. A method comprising administering to a subject in need of hematopoietic stem cell (HSC) engraftment a CXCR4 antagonist and an agent selected from the group consisting of:
   a) (R)-3-Amino-4-(3-hexylphenylamino)-4-oxobutylphosphonic acid (W146), wherein the ratio of the concentration of the CXCR4 antagonist to the concentration of the W146 compound is (0.5-0.6):1.0;
   b) 3-[[2-[4-phenyl-3-(trifluoromethyl)phenyl]-1-benzothiophen-5-yl]methylamino]propanoic acid (AUY954), wherein the ratio of the concentration of the CXCR4 antagonist to the concentration of the AUY954 compound is (0.4-2.5):1.0;
   c) 2-amino-2-[2-(4-octylpheny)ethyl]propane-1,3-diol (FTY720), wherein the ratio of the concentration of the CXCR4 antagonist to the concentration of the 2-amino-2-[2-(4-octylphenyl)ethyl]propane-1,3-diol compound is (0.4-3.0):1.0; and
   d) 5-[4-phenyl-5-(trifluoromethyl)-2-thienyl]-3-[3-(trifluoromethyl)phenyl]-1,2,4-oxadiazole (SEW2871), wherein the ratio of the concentration of the CXCR4 antagonist to the concentration of the 5[4-phenyl-5-(trifluoromethyl)-2-thienyl]-3-[3-(trifluoromethyl)phenyl]-1,2,4-oxadiazole compound is (0.25-1.0):1.0.

2. The method of claim 1, wherein the CXCR4 antagonist is 1,1'-[1,4-Phenylenebis(methylene)]bis[1,4,8,11-tetraazacyclotetradecane] (AMD3100) or T-140.

3. The method of claim 2, wherein the AMD3100 is at a concentration of between 2-10 μM and the concentration of W146 is between of 4-20 μM.

4. The method of claim 1, wherein the subject is administered a population of HSCs prior to, during or after administration of the CXCR4 antagonist and W146, AUY954, FTY720 or SEW287Y.

5. The method of claim 2, wherein the AMD3100 is at a concentration of between 5-20 μM and the concentration of AUY954 is between of 5-25 μM.

6. The method of claim 2, wherein the concentration of AMD3100 is between 10-25 μM and the concentration of FTY720 is between of 2-10 μM.

7. The method of claim 2, wherein the AMD3100 or SEW2871 is at a concentration of between 5-20 μM.

8. The method of claim 1, wherein the subject is a candidate for bone marrow or stem cell transplantation, or a subject that has received bone marrow ablating chemotherapy or irradiation therapy.

* * * * *

UNITED STATES PATENT AND TRADEMARK OFFICE
CERTIFICATE OF CORRECTION

PATENT NO. : 9,763,980 B2
APPLICATION NO. : 14/126768
DATED : September 19, 2017
INVENTOR(S) : Leonard I. Zon and Owen J. Tamplin Page 1 of 1

It is certified that error appears in the above-identified patent and that said Letters Patent is hereby corrected as shown below:

In the Specification

At Column 1, Line 20-23, please delete:
"This invention was supported by the National Institutes of Health - NIH Grant No. NIH R01 HL04880, R01 HL097794-02 and 5R01HL048801-18. The government of the United States has certain rights in this invention."

And insert the following:
-- This invention was made with government support under grant number HL048801 and HL097794 awarded by The National Institutes of Health. The government has certain rights in the invention. --

Signed and Sealed this
Thirty-first Day of March, 2020

Andrei Iancu
*Director of the United States Patent and Trademark Office*